US012404321B2

(12) United States Patent
Cashman et al.

(10) Patent No.: US 12,404,321 B2
(45) Date of Patent: Sep. 2, 2025

(54) CONFORMATION-SPECIFIC EPITOPES IN ALPHA-SYNUCLEIN, ANTIBODIES THERETO AND METHODS RELATED THEREOF

(71) Applicants: THE UNIVERSITY OF BRITISH COLUMBIA, Vancouver (CA); PROMIS NEUROSCIENCES, INC., Toronto (CA)

(72) Inventors: Neil R. Cashman, Vancouver (CA); Steven S. Plotkin, Vancouver (CA); Xubiao Peng, Beijing (CN); Johanne Kaplan, Sherborn, MA (US)

(73) Assignees: University of British Columbia, Vancouver (CA); ProMIS Neurosciences, Inc., Toronto (CA)

( * ) Notice: Subject to any disclaimer, the term of this patent is extended or adjusted under 35 U.S.C. 154(b) by 1105 days.

(21) Appl. No.: 17/283,292

(22) PCT Filed: Oct. 7, 2019

(86) PCT No.: PCT/CA2019/051434
§ 371 (c)(1),
(2) Date: Apr. 7, 2021

(87) PCT Pub. No.: WO2020/073121
PCT Pub. Date: Apr. 16, 2020

(65) Prior Publication Data
US 2023/0051538 A1    Feb. 16, 2023

Related U.S. Application Data

(60) Provisional application No. 62/864,060, filed on Jun. 20, 2019, provisional application No. 62/820,701, filed on Mar. 19, 2019, provisional application No. 62/780,599, filed on Dec. 17, 2018, provisional application No. 62/742,408, filed on Oct. 7, 2018.

(51) Int. Cl.
| | |
|---|---|
| *C07K 16/18* | (2006.01) |
| *A61P 25/00* | (2006.01) |
| *C12N 15/63* | (2006.01) |
| *G01N 33/68* | (2006.01) |
| *A61K 39/00* | (2006.01) |

(52) U.S. Cl.
CPC .............. *C07K 16/18* (2013.01); *A61P 25/00* (2018.01); *C12N 15/63* (2013.01); *G01N 33/6896* (2013.01); *A61K 39/00* (2013.01); *C07K 2317/565* (2013.01); *C07K 2317/92* (2013.01)

(58) Field of Classification Search
None
See application file for complete search history.

(56) References Cited

U.S. PATENT DOCUMENTS

2011/0319334 A1    12/2011  Shaltiel-Karyo et al.
2014/0314773 A1*  10/2014  Cashman ............... A61K 45/06
                                                          435/7.1

FOREIGN PATENT DOCUMENTS

| CN | 102504016 B | 5/2014 | |
|---|---|---|---|
| EP | 3026057 A2 * | 6/2016 | ............. C07K 14/47 |
| JP | 2008-517928 A | 5/2008 | |
| JP | 2011-512363 A | 4/2011 | |
| JP | 2016-511254 A | 4/2016 | |
| WO | 2010002251 A1 | 1/2010 | |
| WO | 2011/013034 A4 | 2/2011 | |
| WO | 2017/079832 A1 | 5/2017 | |
| WO | 2017/189959 A1 | 11/2017 | |
| WO | 2018/014126 A1 | 1/2018 | |
| WO | 2018/115225 A1 | 6/2018 | |

OTHER PUBLICATIONS

Meuleman et al., Immobilization by surface conjugation of cyclic peptides for effective mimicry of the HCV-envelope E2 protein as a strategy toward synthetic vaccines; Jan. 31, 2018, Bioconjugate Chem., 29, pp. 1091-1101. (Year: 2018).*
MacCallum et al., Antibody-antigen Interactions: contact analysis and binding site topography; 1996, J. Mol. Biol., 262: 732-745. (Year: 1996).*
Xu, Liang et al. Coupling of the Non-Amyloid-Component (NAC) Domain and the KTK(E/Q)GV Repeats Stabilize the α-Synuclein Fibrils. Eur J Med Chem. Oct. 4, 2016; 121: 841-850.
Vaikath, Nishant N. et al. Generation and characterization of novel conformation-specific monoclonal antibodies for α-Synuclein pathology. Neurobiology of Disease. Jul. 2015, vol. 79, pp. 81-99.
Masuda, Masami, Inhibition of α-Synuclein fibril assembly by small molecules: Analysis using epitope-specific antibodies. FEBS Letters 583 (2009) 787-791.
Kritzer, Joshua A. et al. Rapid selection of cyclic peptides that reduce alpha-synuclein toxicity in yeast and animal models. Nature Chemical Biology. vol. 5, No. 9, Jul. 13, 2009, pp. 655-663.
Silverman Judith M. et al. A Rational Structured Epitope Defines a Distinct Subclass of Toxic Amyloid-beta Oligomers. ACS Chemical Neuroscience. vol. 9, No. 7, Jul. 18, 2018, pp. 1591-1606.
Peng, Xubiao et al. Prediction of Misfolding-Specific Epitopes in SOD1 Using Collective Coordinates. Journal of Physical Chemistry, Part B. vol. 122, No. 49, Oct. 16, 2018, pp. 11662-11676.
Hong, D.-P. et al. The role of the C-terminus of human α-synuclein: intra-disulfide bonds between the C-terminus and other regions stabilize non-fibrillar monomeric isomers. FEBS Letters, 2011, vol. 585, pp. 561-566. Retrieved on Oct. 23, 2019 DOI:10.1016/j.febslet.2011.01.009.

(Continued)

*Primary Examiner* — Daniel E Kolker
*Assistant Examiner* — James Ryland Melchior
(74) *Attorney, Agent, or Firm* — Smart & Biggar LP; Carmela De Luca

(57) ABSTRACT

The disclosure pertains to conformational epitopes in alpha-synuclein, antibodies thereto and methods of making and using immunogens and antibodies specific thereto. In particular antibodies raised to cyclic compounds comprising at least 3 amino acids of EKTKEQ (SEQ ID NO: 1) selectively recognize misfolded oligomeric alpha-synuclein and are able to inhibit alpha-synuclein propagation and toxicity.

18 Claims, 28 Drawing Sheets

Specification includes a Sequence Listing.

(56) References Cited

OTHER PUBLICATIONS

Nuber, S. et al. Abrogating Native α-Synuclein Tetramers in Mice Causes a L-DOPA-Responsive Motor Syndrome Cloaely Resembling Parkinson's Disease. Neuron 100, 75-90, Oct. 10, 2018.

Winner, B. et al. In vivo demonstration that α-synuclein oligomers are toxic. PNAS, Mar. 8, 2011, vol. 108, No. 10, 4194-4199.

Ueda, K. et al. Molecular cloning of cDNA encoding an unrecognized component of amyloid in Alzheimer disease. Proc. Natl. Acad. Sci. USA, vol. 90, pp. 11282-11286, Dec. 1993.

Diao, J. et al. Native α-synuclein induces clustering of synaptic-vesicle mimics via binding to phospholipids and synaptobrevin-2/VAMP2. eLife, 2013; 2:e00592 DOI: 10.7554/eLife.00592.

Games, D. et al. Reducing C-Terminal-Truncated Alpha-Synuclein by Immunotherapy Attenuates Neurodegeneration and Propagation in Parkinson's Disease-Like Models, The Journal of Neuroscience, Jul. 9, 2014, vol. 34, No. 28, 9441-9454.

Kallab, M. et al. Region-Specific Effects of Immunotherapy with Antibodies Targeting α-synuclein in a Transgenic Model of Synucleinopathy, Frontiers in Neuroscience, Jul. 2018, vol. 12, Article 452, DOI: 10.3389/fnins.2018.00452.

Bartels, T. et al. α-Synuclein occurs physiologically as a helically folded tetramer that resists aggregation, Nature, Sep. 1, 2011, vol. 477, pp. 107-110; DOI: 10.1038/nature10324.

Masliah, E. et al. Passive Immunization Reduces Behavioral and Neuropathological Deficits in an Alpha-Synuclein Transgenic Model of Lewy Body Disease; Apr. 2011, PLoS ONE, vol. 6, Issue 4, e19338; DOI: 10.1371/journal.pone.0019338.

Nasstrom, T. et al. Antibodies against Alpha-Synuclein Reduce Oligomerization in Living Cells, Oct. 2011, PLoS ONE, vol. 6, Issue 10, e27230; DOI: 10.1371/journal.pone.0027230.

Cashman N. et al. Targeting of Pathogenic Aggregated Alpha-Synuclein: Refining Antibody Epitotes by Design, ADPD, Mar. 31, 2019, Poster Presentation at ADPD 2019 Conference in Lisbon, Portugal.

Cashman N. et al. Targeting of Pathogenic Aggregated Alpha-Synuclein: Refining Antibody Epitotes by Design, ADPD, Mar. 31, 2019, Abstract of Oral Presentation at ADPD 2019 Conference in Lisbon, Portugal.

Anonymous: "UPI000B434811; UniParc; UniProt" Nov. 22, 2017. Retrieved from the internet: URL:https://uniprot.org/uniparc/UPI000B4E4811/entry—Retrieved on Oct. 14, 2022.

Anonymous: "UPI0001F8F992; UniParc; UniProt", Sep. 12, 2018. Retrieved from the internet: URL:https://www.uniprot.org/uniparc/UPI0001F8F992/entry—Retrieved on Oct. 14, 2022.

* cited by examiner

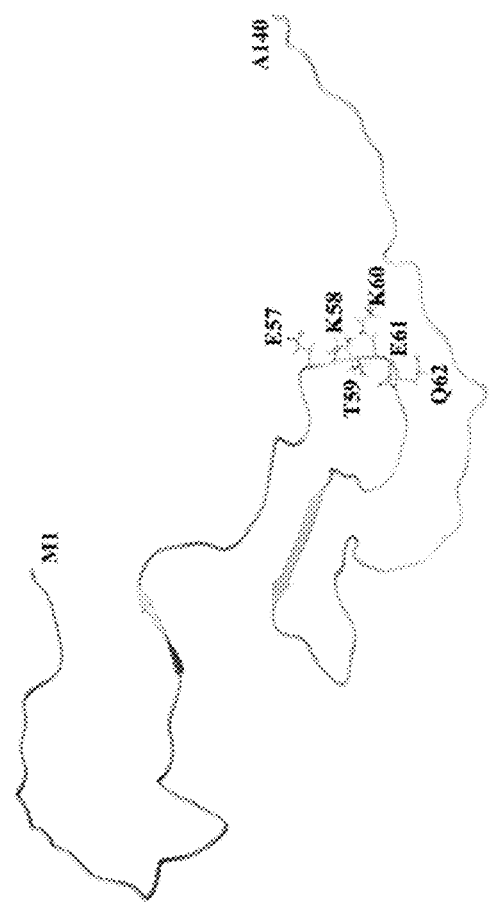
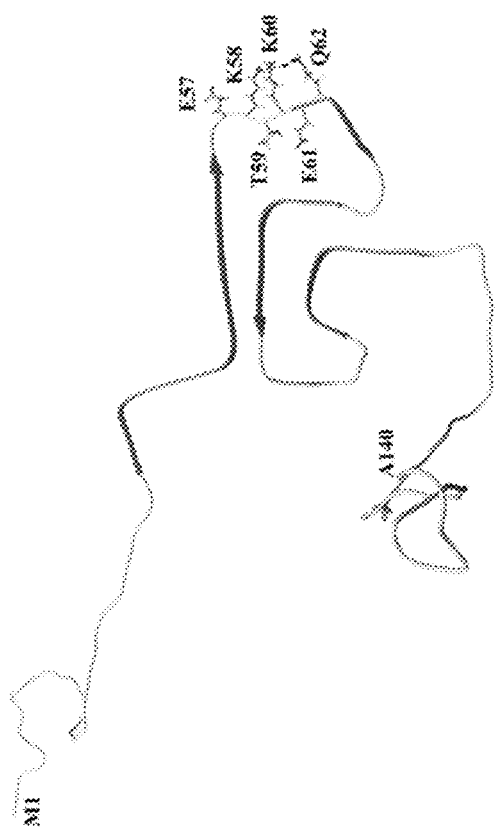
Fig. 2A
Fig. 2B

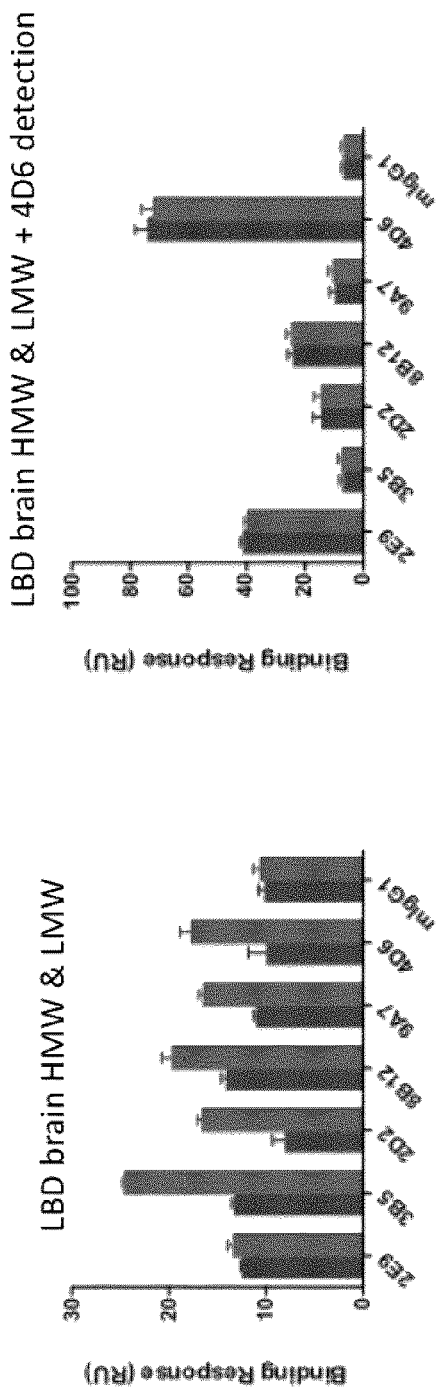
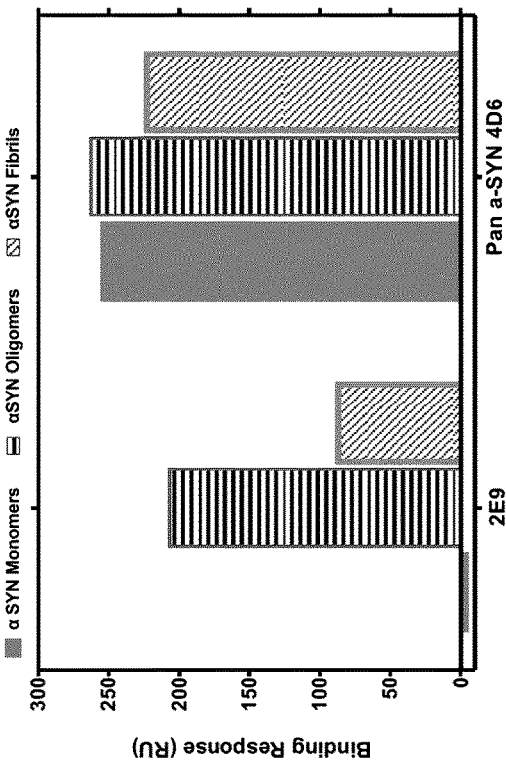
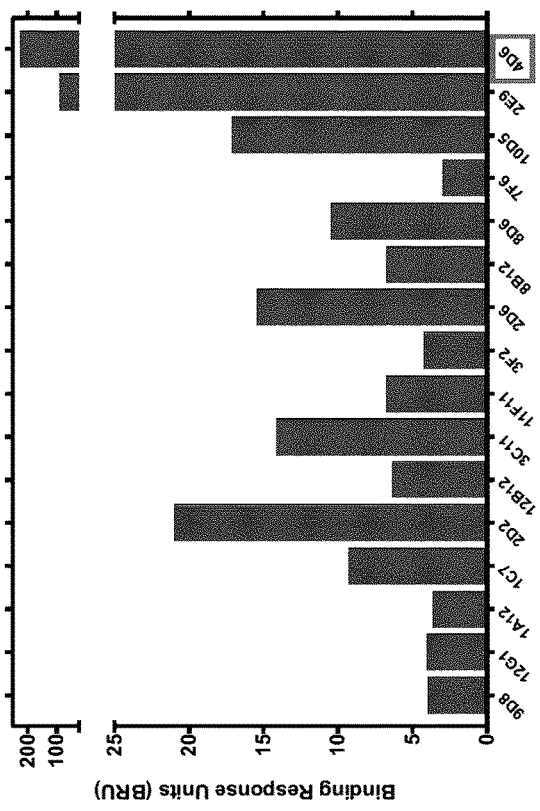
Fig. 6F
Fig. 6G
Fig. 6H

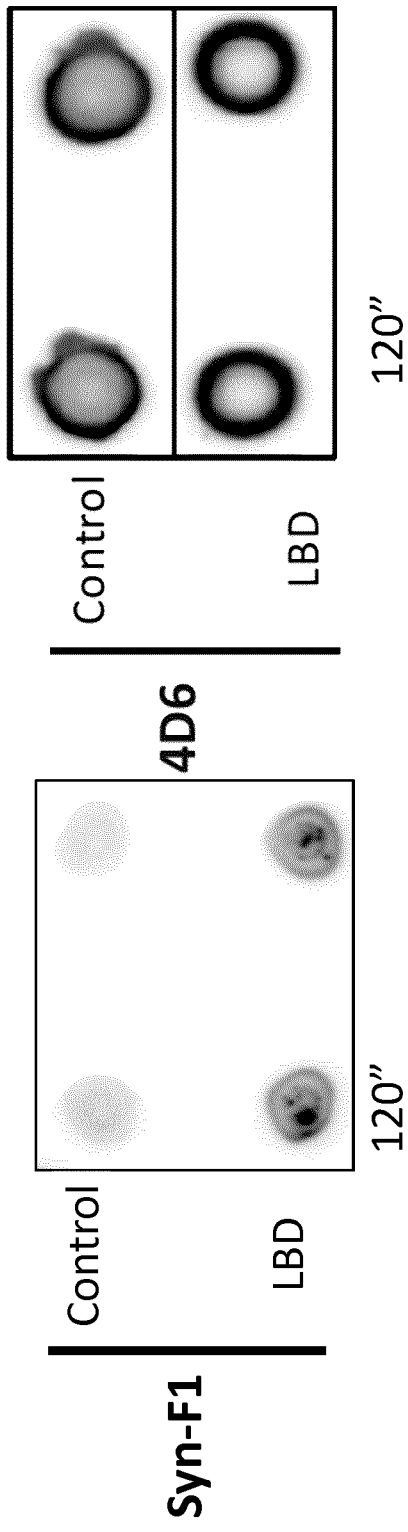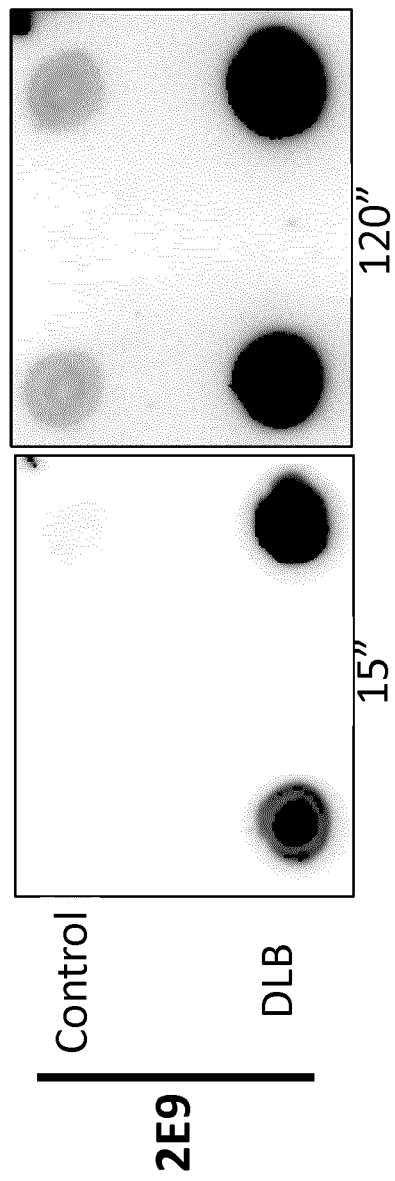
Fig. 7A
Fig. 7B

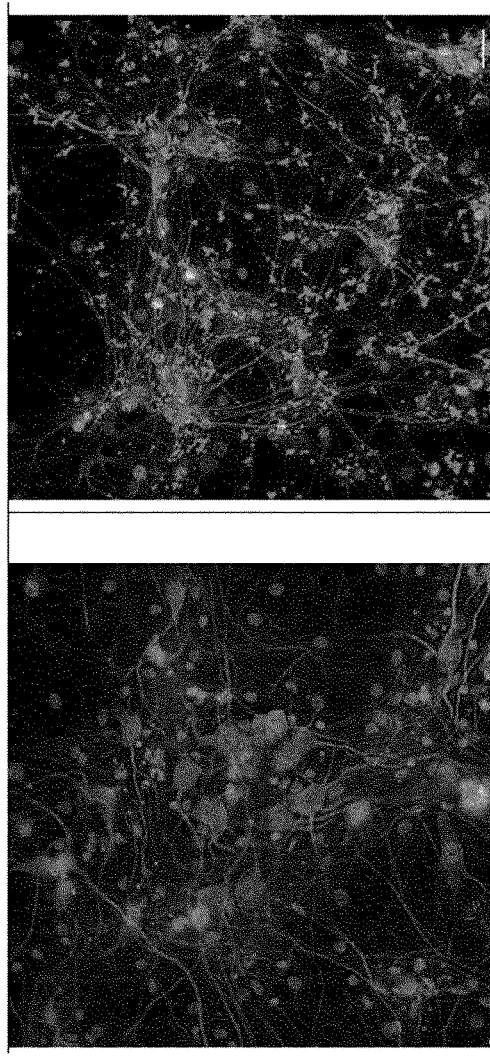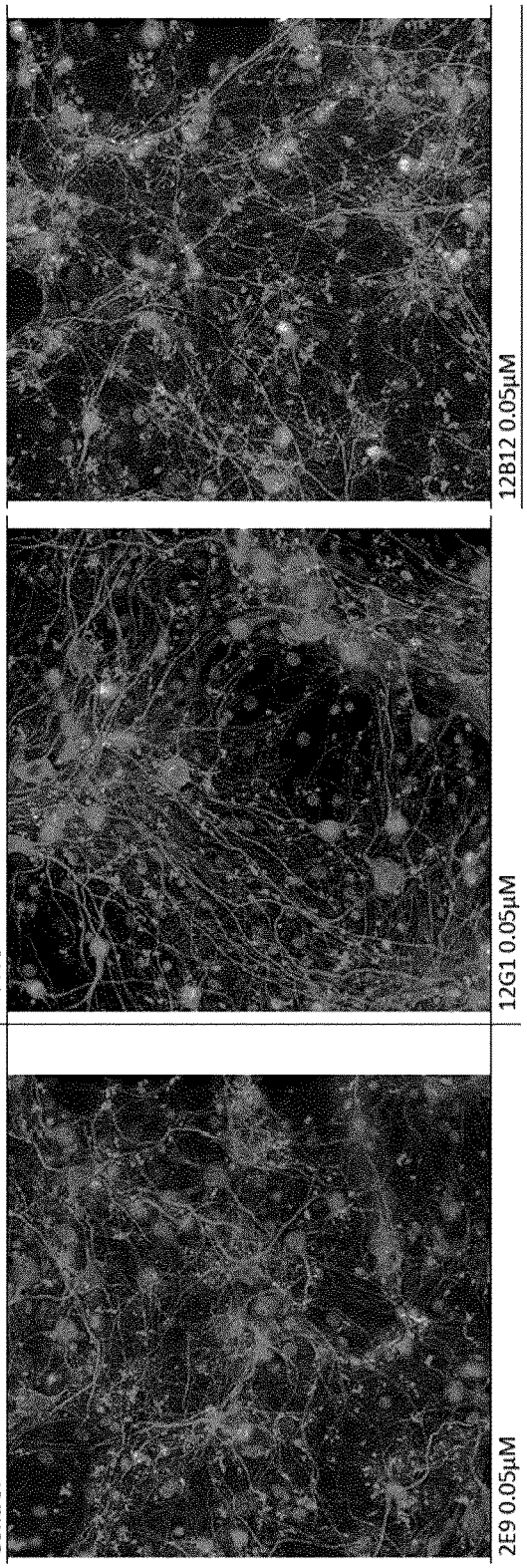

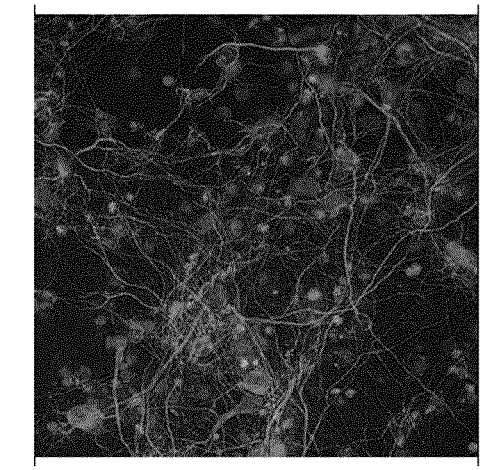
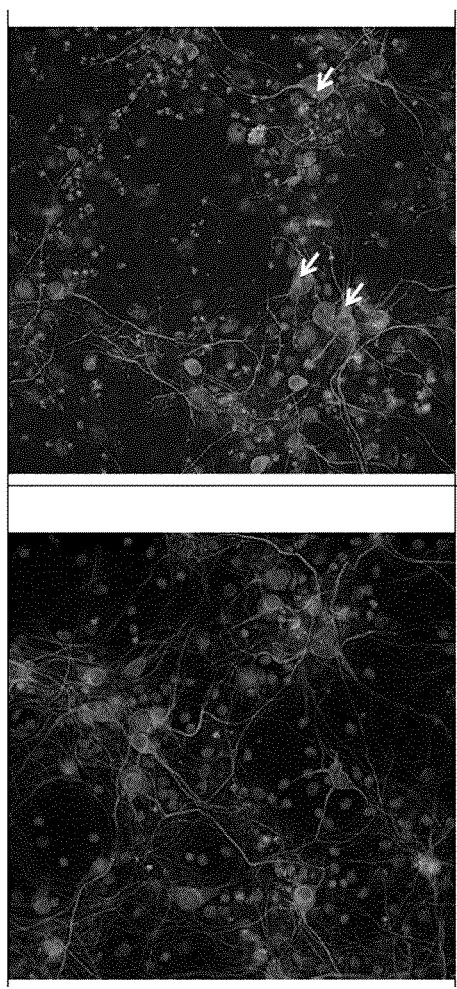
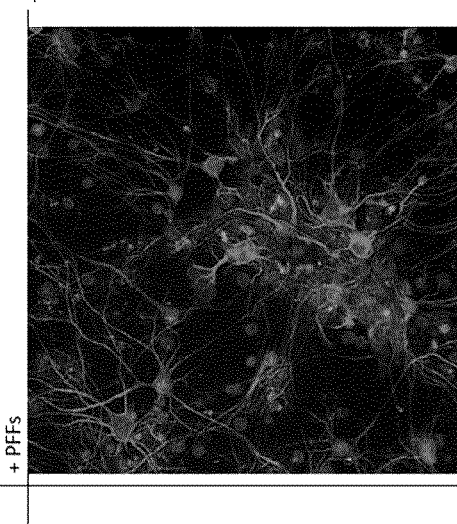
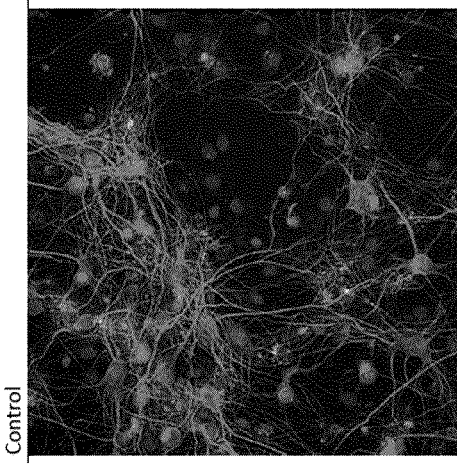
Fig. 14C Fig. 14D Fig. 14E Fig. 14F Fig. 14G

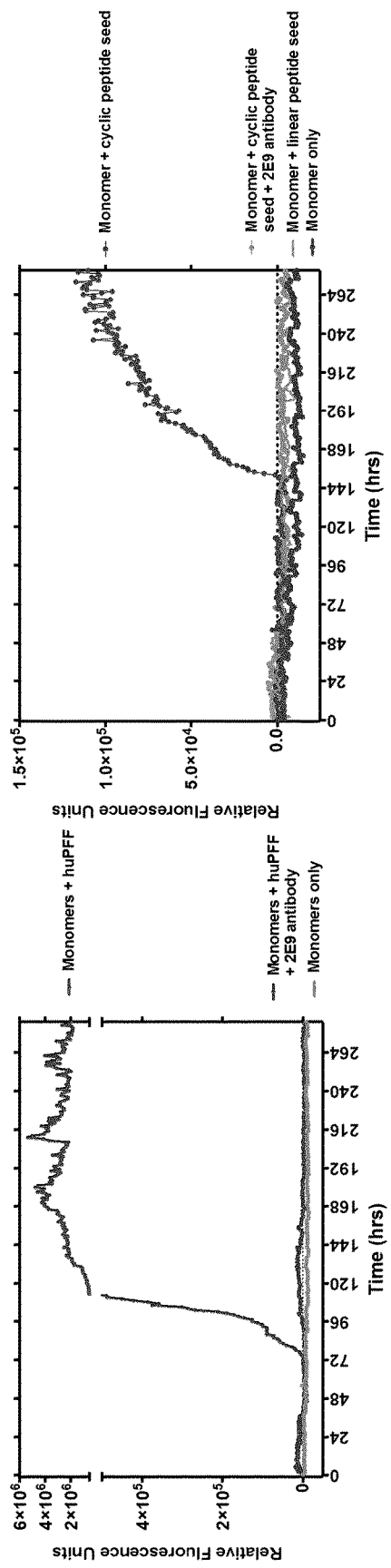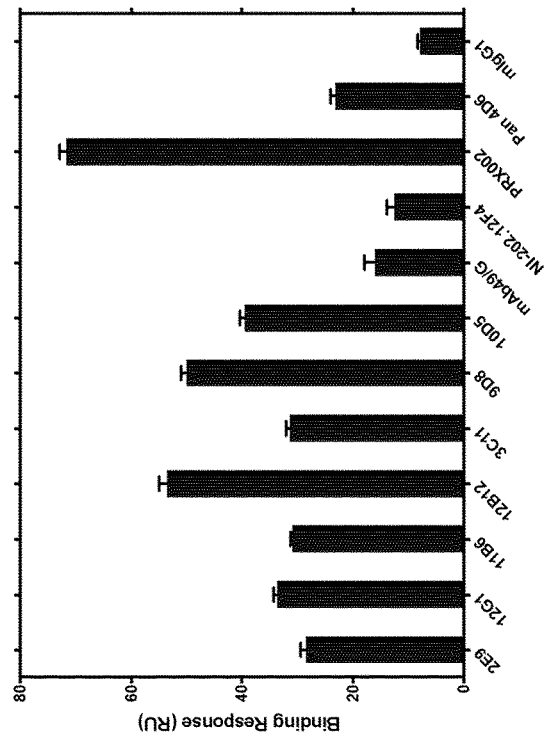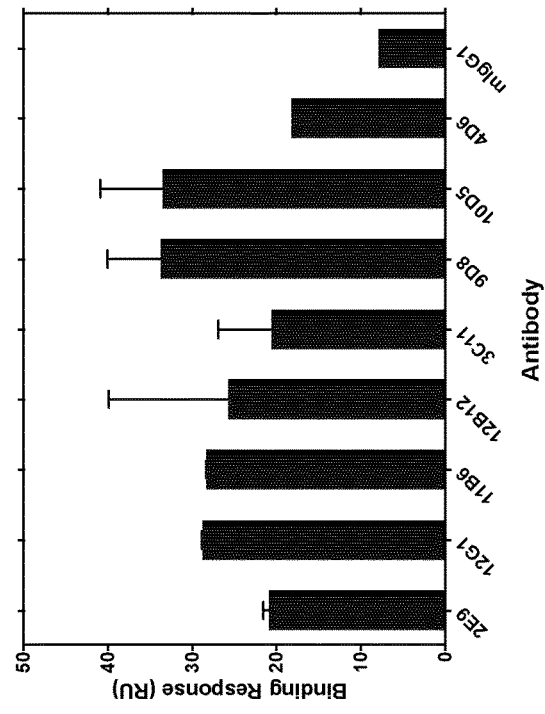
Fig. 15A
Fig. 15B
Fig. 16A
Fig. 16B

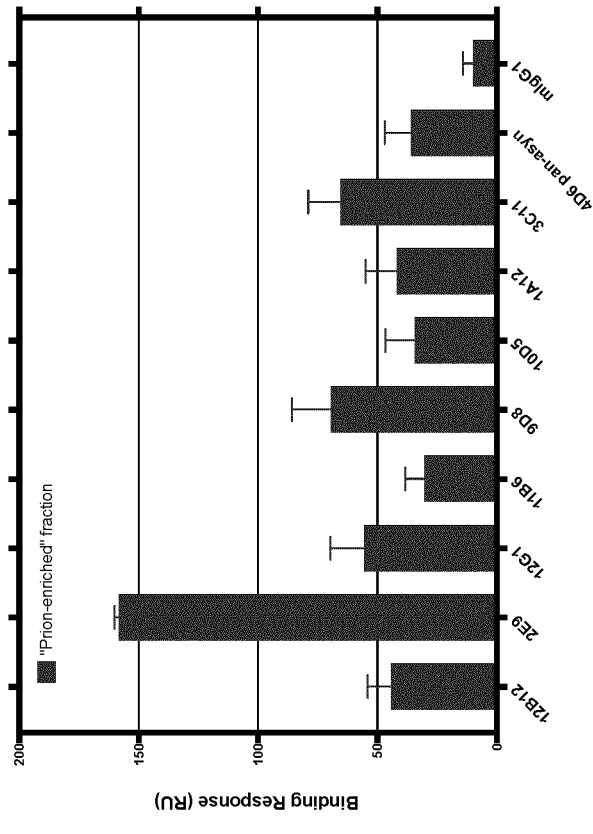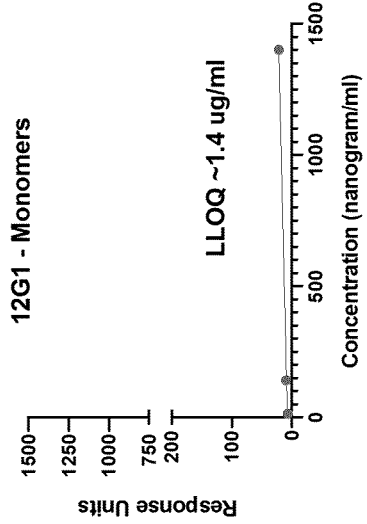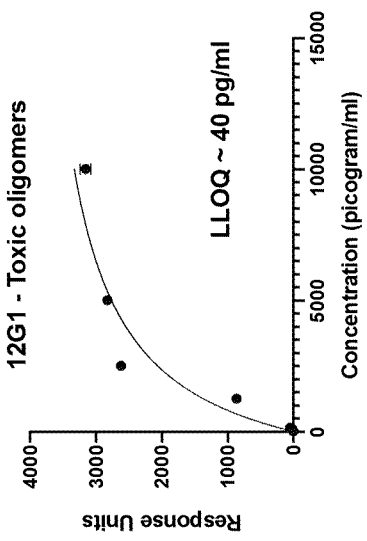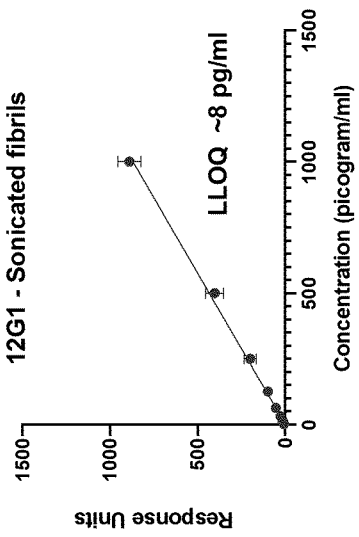

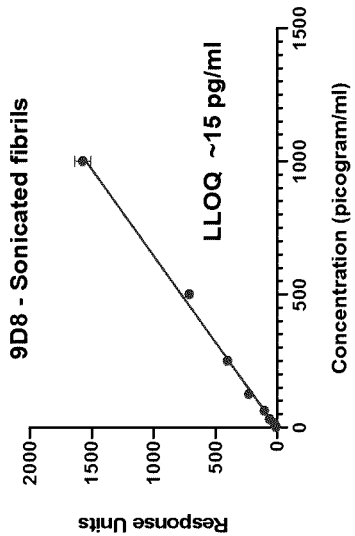
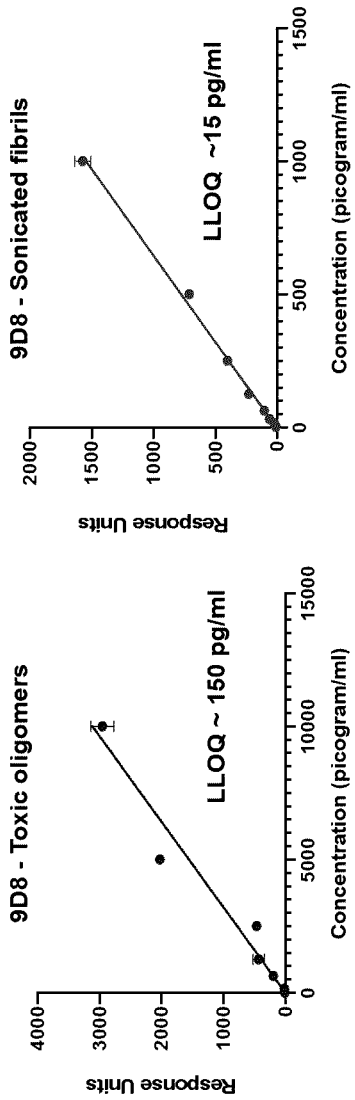
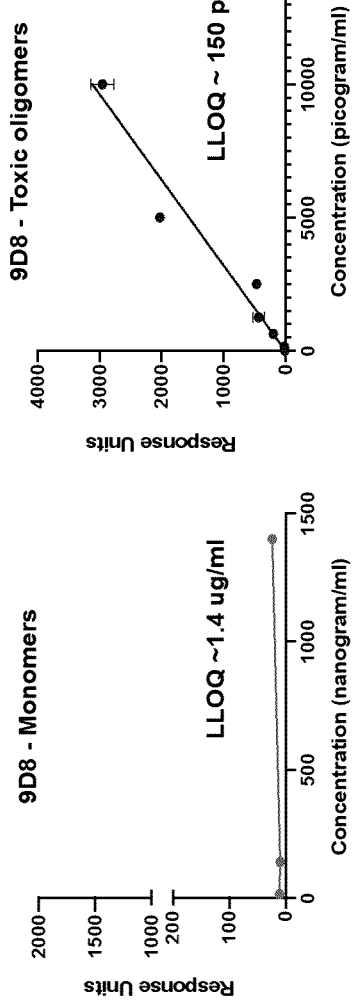
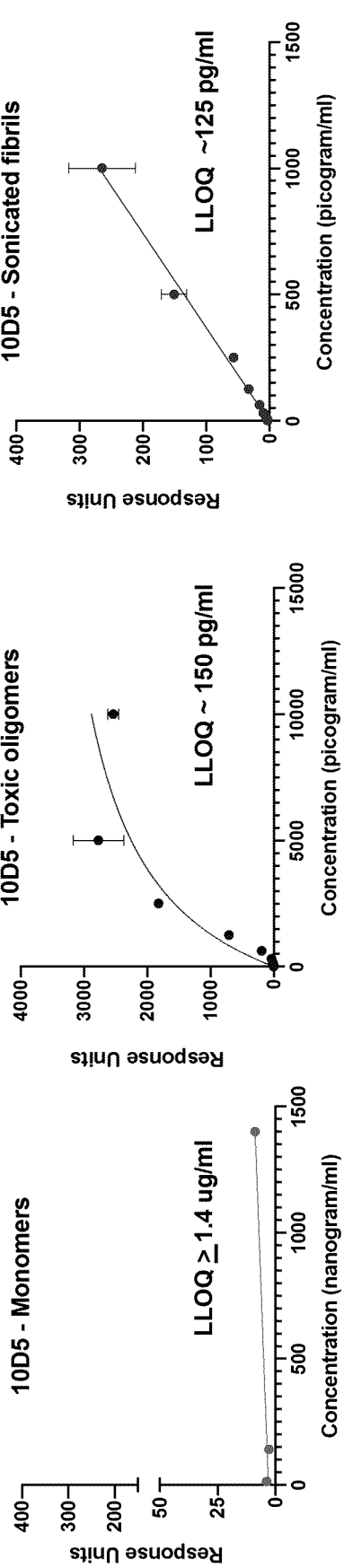

SEQUENCE LISTING

```
<160> NUMBER OF SEQ ID NOS: 193

<210> SEQ ID NO 1
<211> LENGTH: 6
<212> TYPE: PRT
<213> ORGANISM: Homo Sapiens

<400> SEQUENCE: 1

Glu Lys Thr Lys Glu Gln
1               5

<210> SEQ ID NO 2
<211> LENGTH: 4
<212> TYPE: PRT
```

```
<213> ORGANISM: Homo Sapiens

<400> SEQUENCE: 2

Glu Lys Thr Lys
1

<210> SEQ ID NO 3
<211> LENGTH: 4
<212> TYPE: PRT
<213> ORGANISM: Homo Sapiens

<400> SEQUENCE: 3

Lys Thr Lys Glu
1

<210> SEQ ID NO 4
<211> LENGTH: 4
<212> TYPE: PRT
<213> ORGANISM: Homo Sapiens

<400> SEQUENCE: 4

Thr Lys Glu Gln
1

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

Cys Gly Gly Gly Gly Glu Lys Thr Lys Gly Gly
1               5                   10

<210> SEQ ID NO 6
<211> LENGTH: 6
<212> TYPE: PRT
<213> ORGANISM: Homo Sapiens

<400> SEQUENCE: 6

Lys Thr Lys Glu Gly Val
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic Construct

<400> SEQUENCE: 7

Cys Gly Thr Lys Glu Gln Gly Gly Gly Gly
1               5                   10

<210> SEQ ID NO 8
<211> LENGTH: 5
<212> TYPE: PRT
<213> ORGANISM: Homo Sapiens

<400> SEQUENCE: 8

Glu Lys Thr Lys Glu
1               5

<210> SEQ ID NO 9
```

```
<211> LENGTH: 5
<212> TYPE: PRT
<213> ORGANISM: Homo Sapiens

<400> SEQUENCE: 9

Lys Thr Lys Glu Gln
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic Construct

<400> SEQUENCE: 10

Cys Gly Gly Gly Glu Lys Thr Lys Gly Gly
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct

<400> SEQUENCE: 11

Cys Gly Gly Gly Gly Thr Lys Glu Gln Gly Gly
1               5                   10

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct

<400> SEQUENCE: 12

Gly Cys Gly Gly Gly Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Construct

<400> SEQUENCE: 13

Gly Gly Cys Gly Gly
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Construct

<400> SEQUENCE: 14

Gly Gly Cys Gly Gly Gly Gly
1               5

<210> SEQ ID NO 15
<211> LENGTH: 6
<212> TYPE: PRT
<213> ORGANISM: Artificial Sequence
```

```
<220> FEATURE:
<223> OTHER INFORMATION: Synthetic Construct

<400> SEQUENCE: 15

Gly Gly Gly Cys Gly Gly
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic Construct

<400> SEQUENCE: 16

Gly Gly Gly Gly Cys Gly Gly
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Cys Gly Gly Glu Lys Thr Lys Gly Gly Cys
1               5                   10

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Cys Gly Glu Lys Thr Lys Gly Gly Gly
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Cys Gly Glu Lys Thr Lys Gly Gly
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Cys Gly Gly Glu Lys Thr Lys Gly Gly Gly
1               5                   10

<210> SEQ ID NO 21
<211> LENGTH: 9
<212> TYPE: PRT
<213> ORGANISM: Artificial Sequence
<220> FEATURE:
```

<223> OTHER INFORMATION: Synthetic Construct

<400> SEQUENCE: 21

Cys Gly Gly Gly Glu Lys Thr Lys Gly
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic Construct

<400> SEQUENCE: 22

Cys Gly Glu Lys Thr Lys Gly
1               5

<210> SEQ ID NO 23
<211> LENGTH: 13
<212> TYPE: PRT
<213> ORGANISM: Artificial Sequence
<220> FEATURE:
<223> OTHER INFORMATION: Synthetic Construct

<400> SEQUENCE: 23

Cys Gly Gly Gly Gly Glu Lys Thr Lys Gly Gly Gly Gly
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic Construct

<400> SEQUENCE: 24

Cys Gly Gly Gly Glu Lys Thr Lys Gly Gly Gly
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic Construct

<400> SEQUENCE: 25

Cys Gly Gly Gly Gly Glu Lys Thr Lys Gly Gly Gly
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic Construct

<400> SEQUENCE: 26

Cys Gly Glu Lys Thr Lys Gly Gly Gly Gly
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Synthetic Construct

<400> SEQUENCE: 27

Cys Gly Gly Glu Lys Thr Lys Gly
1               5

<210> SEQ ID NO 28
<211> LENGTH: 12
<212> TYPE: PRT
<213> ORGANISM: Artificial Sequence
<220> FEATURE:
<223> OTHER INFORMATION: Synthetic Construct

<400> SEQUENCE: 28

Cys Gly Gly Gly Glu Lys Thr Lys Gly Gly Gly Gly
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct

<400> SEQUENCE: 29

Cys Gly Gly Glu Lys Thr Lys Gly Gly
1               5

<210> SEQ ID NO 30
<211> LENGTH: 11
<212> TYPE: PRT
<213> ORGANISM: Artificial Sequence
<220> FEATURE:
<223> OTHER INFORMATION: Synthetic Construct

<400> SEQUENCE: 30

Cys Gly Gly Glu Lys Thr Lys Gly Gly Gly Gly
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic Construct

<400> SEQUENCE: 31

Cys Gly Gly Gly Gly Glu Lys Thr Lys Gly
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

Cys Gly Gly Gly Gly Lys Thr Lys Glu Gly Gly
1               5                   10

<210> SEQ ID NO 33
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 33

Cys Gly Gly Lys Thr Lys Glu Gly Gly
1               5

<210> SEQ ID NO 34
<211> LENGTH: 10
<212> TYPE: PRT
<213> ORGANISM: Artificial Sequence
<220> FEATURE:
<223> OTHER INFORMATION: Synthetic Construct

<400> SEQUENCE: 34

Cys Gly Gly Gly Gly Lys Thr Lys Glu Gly
1               5                   10

<210> SEQ ID NO 35
<211> LENGTH: 8
<212> TYPE: PRT
<213> ORGANISM: Artificial Sequence
<220> FEATURE:
<223> OTHER INFORMATION: Synthetic Construct

<400> SEQUENCE: 35

Cys Gly Lys Thr Lys Glu Gly Gly
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic Construct

<400> SEQUENCE: 36

Cys Gly Gly Lys Thr Lys Glu Gly
1               5

<210> SEQ ID NO 37
<211> LENGTH: 12
<212> TYPE: PRT
<213> ORGANISM: Artificial Sequence
<220> FEATURE:
<223> OTHER INFORMATION: Synthetic Construct

<400> SEQUENCE: 37

Cys Gly Gly Gly Lys Thr Lys Glu Gly Gly Gly Gly
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Synthetic Construct

<400> SEQUENCE: 38

Cys Gly Gly Gly Gly Lys Thr Lys Glu Gly Gly Gly
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic Construct

<400> SEQUENCE: 39
```

```
Cys Gly Gly Gly Lys Thr Lys Glu Gly Gly Gly
1               5                   10
```

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct

<400> SEQUENCE: 40

```
Cys Gly Lys Thr Lys Glu Gly
1               5
```

<210> SEQ ID NO 41
<211> LENGTH: 13
<212> TYPE: PRT
<213> ORGANISM: Artificial Sequence
<220> FEATURE:
<223> OTHER INFORMATION: Synthetic Construct

<400> SEQUENCE: 41

```
Cys Gly Gly Gly Gly Lys Thr Lys Glu Gly Gly Gly Gly
1               5                   10
```

<210> SEQ ID NO 42
<211> LENGTH: 9
<212> TYPE: PRT
<213> ORGANISM: Artificial Sequence
<220> FEATURE:
<223> OTHER INFORMATION: Synthetic Construct

<400> SEQUENCE: 42

```
Cys Gly Gly Gly Lys Thr Lys Glu Gly
1               5
```

<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43

```
Cys Gly Gly Lys Thr Lys Glu Gly Gly Gly
1               5                   10
```

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct

<400> SEQUENCE: 44

```
Cys Gly Lys Thr Lys Glu Gly Gly Gly
1               5
```

<210> SEQ ID NO 45
<211> LENGTH: 10
<212> TYPE: PRT
<213> ORGANISM: Artificial Sequence
<220> FEATURE:
<223> OTHER INFORMATION: Synthetic Construct

<400> SEQUENCE: 45

Cys Gly Lys Thr Lys Glu Gly Gly Gly Gly
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic Construct

<400> SEQUENCE: 46

Cys Gly Gly Lys Thr Lys Glu Gly Gly Gly Gly
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Synthetic Construct

<400> SEQUENCE: 47

Cys Gly Gly Thr Lys Glu Gln Gly Gly Gly
1               5                   10

<210> SEQ ID NO 48
<211> LENGTH: 9
<212> TYPE: PRT
<213> ORGANISM: Artificial Sequence
<220> FEATURE:
<223> OTHER INFORMATION: Synthetic Construct

<400> SEQUENCE: 48

Cys Gly Gly Thr Lys Glu Gln Gly Gly
1               5

<210> SEQ ID NO 49
<211> LENGTH: 11
<212> TYPE: PRT
<213> ORGANISM: Artificial Sequence
<220> FEATURE:
<223> OTHER INFORMATION: Synthetic Construct

<400> SEQUENCE: 49

Cys Gly Gly Thr Lys Glu Gln Gly Gly Gly Gly
1               5                   10

<210> SEQ ID NO 50
<211> LENGTH: 8
<212> TYPE: PRT
<213> ORGANISM: Artificial Sequence
<220> FEATURE:
<223> OTHER INFORMATION: Synthetic Construct

<400> SEQUENCE: 50

Cys Gly Gly Thr Lys Glu Gln Gly
1               5

<210> SEQ ID NO 51
<211> LENGTH: 13
<212> TYPE: PRT
<213> ORGANISM: Artificial Sequence
<220> FEATURE:
<223> OTHER INFORMATION: Synthetic Construct

<400> SEQUENCE: 51

Cys Gly Gly Gly Gly Thr Lys Glu Gln Gly Gly Gly Gly

```
1               5                   10

<210> SEQ ID NO 52
<211> LENGTH: 12
<212> TYPE: PRT
<213> ORGANISM: Artificial Sequence
<220> FEATURE:
<223> OTHER INFORMATION: Synthetic Construct

<400> SEQUENCE: 52

Cys Gly Gly Gly Gly Thr Lys Glu Gln Gly Gly Gly
1               5                   10

<210> SEQ ID NO 53
<211> LENGTH: 8
<212> TYPE: PRT
<213> ORGANISM: Artificial Sequence
<220> FEATURE:
<223> OTHER INFORMATION: Synthetic Construct

<400> SEQUENCE: 53

Cys Gly Thr Lys Glu Gln Gly Gly
1               5

<210> SEQ ID NO 54
<211> LENGTH: 11
<212> TYPE: PRT
<213> ORGANISM: Artificial Sequence
<220> FEATURE:
<223> OTHER INFORMATION: Synthetic Construct

<400> SEQUENCE: 54

Cys Gly Gly Gly Thr Lys Glu Gln Gly Gly Gly
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic Construct

<400> SEQUENCE: 55

Cys Gly Gly Gly Thr Lys Glu Gln Gly Gly
1               5                   10

<210> SEQ ID NO 56
<211> LENGTH: 7
<212> TYPE: PRT
<213> ORGANISM: Artificial Sequence
<220> FEATURE:
<223> OTHER INFORMATION: Synthetic Construct

<400> SEQUENCE: 56

Cys Gly Thr Lys Glu Gln Gly
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic Construct

<400> SEQUENCE: 57

Cys Gly Thr Lys Glu Gln Gly Gly Gly
1               5
```

<210> SEQ ID NO 58
<211> LENGTH: 12
<212> TYPE: PRT
<213> ORGANISM: Artificial Sequence
<220> FEATURE:
<223> OTHER INFORMATION: Synthetic Construct

<400> SEQUENCE: 58

Cys Gly Gly Gly Thr Lys Glu Gln Gly Gly Gly Gly
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic Construct

<400> SEQUENCE: 59

Cys Gly Gly Gly Gly Thr Lys Glu Gln Gly
1               5                   10

<210> SEQ ID NO 60
<211> LENGTH: 9
<212> TYPE: PRT
<213> ORGANISM: Artificial Sequence
<220> FEATURE:
<223> OTHER INFORMATION: Synthetic Construct

<400> SEQUENCE: 60

Cys Gly Gly Gly Thr Lys Glu Gln Gly
1               5

<210> SEQ ID NO 61
<211> LENGTH: 8
<212> TYPE: PRT
<213> ORGANISM: Mus Musculus

<400> SEQUENCE: 61

Gly Phe Asp Phe Ser Arg Tyr Trp
1               5

<210> SEQ ID NO 62
<211> LENGTH: 8
<212> TYPE: PRT
<213> ORGANISM: Mus Musculus

<400> SEQUENCE: 62

Ile Asn Pro His Ser Ser Thr Ile
1               5

<210> SEQ ID NO 63
<211> LENGTH: 8
<212> TYPE: PRT
<213> ORGANISM: Mus Musculus

<400> SEQUENCE: 63

Gly Arg Gly Asp Tyr Val Asp Tyr
1               5

<210> SEQ ID NO 64
<211> LENGTH: 12
<212> TYPE: PRT
<213> ORGANISM: Mus Musculus

```
<400> SEQUENCE: 64

Gln Ser Leu Leu Tyr Ser Arg Asn Gln Lys Asn Tyr
1               5                   10

<210> SEQ ID NO 65
<211> LENGTH: 3
<212> TYPE: PRT
<213> ORGANISM: Mus Musculus

<400> SEQUENCE: 65

Trp Ala Ser
1

<210> SEQ ID NO 66
<211> LENGTH: 9
<212> TYPE: PRT
<213> ORGANISM: Mus Musculus

<400> SEQUENCE: 66

Gln Gln Tyr Tyr Ser Tyr Pro Arg Thr
1               5

<210> SEQ ID NO 67
<211> LENGTH: 10
<212> TYPE: PRT
<213> ORGANISM: Mus Musculus

<400> SEQUENCE: 67

Gly Phe Ser Leu Ser Thr Ser Gly Met Gly
1               5                   10

<210> SEQ ID NO 68
<211> LENGTH: 7
<212> TYPE: PRT
<213> ORGANISM: Mus Musculus

<400> SEQUENCE: 68

Ile Trp Trp Asp Gly Asp Lys
1               5

<210> SEQ ID NO 69
<211> LENGTH: 12
<212> TYPE: PRT
<213> ORGANISM: Mus Musculus

<400> SEQUENCE: 69

Thr Arg Ile Val Val Pro Asn Phe Leu Phe Thr Tyr
1               5                   10

<210> SEQ ID NO 70
<211> LENGTH: 11
<212> TYPE: PRT
<213> ORGANISM: Mus Musculus

<400> SEQUENCE: 70

Gln Ser Ile Val Gln Ser Asn Gly Asn Thr Tyr
1               5                   10

<210> SEQ ID NO 71
<211> LENGTH: 3
<212> TYPE: PRT
<213> ORGANISM: Mus Musculus

<400> SEQUENCE: 71
```

Lys Val Ser
1

<210> SEQ ID NO 72
<211> LENGTH: 9
<212> TYPE: PRT
<213> ORGANISM: Mus Musculus

<400> SEQUENCE: 72

Phe Gln Gly Ser His Val Pro Phe Thr
1               5

<210> SEQ ID NO 73
<211> LENGTH: 8
<212> TYPE: PRT
<213> ORGANISM: Mus Musculus

<400> SEQUENCE: 73

Gly Tyr Thr Phe Thr Thr Ala Gly
1               5

<210> SEQ ID NO 74
<211> LENGTH: 8
<212> TYPE: PRT
<213> ORGANISM: Mus Musculus

<400> SEQUENCE: 74

Ile Asn Thr His Ser Gly Val Pro
1               5

<210> SEQ ID NO 75
<211> LENGTH: 8
<212> TYPE: PRT
<213> ORGANISM: Mus Musculus

<400> SEQUENCE: 75

Ala Arg Thr Ser Trp Ala Pro Tyr
1               5

<210> SEQ ID NO 76
<211> LENGTH: 11
<212> TYPE: PRT
<213> ORGANISM: Mus Musculus

<400> SEQUENCE: 76

Gln Ser Leu Leu Asp Ser Asp Gly Lys Thr Tyr
1               5                   10

<210> SEQ ID NO 77
<211> LENGTH: 3
<212> TYPE: PRT
<213> ORGANISM: Mus Musculus

<400> SEQUENCE: 77

Leu Val Ser
1

<210> SEQ ID NO 78
<211> LENGTH: 9
<212> TYPE: PRT
<213> ORGANISM: Mus Musculus

<400> SEQUENCE: 78

Trp Gln Gly Thr His Phe Pro Gln Thr
1               5

<210> SEQ ID NO 79
<211> LENGTH: 8
<212> TYPE: PRT
<213> ORGANISM: Mus Musculus

<400> SEQUENCE: 79

Gly Phe Asn Ile Lys Asp Thr Tyr
1               5

<210> SEQ ID NO 80
<211> LENGTH: 8
<212> TYPE: PRT
<213> ORGANISM: Mus Musculus

<400> SEQUENCE: 80

Ile Asp Pro Ala Asn Gly Asn Thr
1               5

<210> SEQ ID NO 81
<211> LENGTH: 8
<212> TYPE: PRT
<213> ORGANISM: Mus Musculus

<400> SEQUENCE: 81

Ser Asn Trp Asp Tyr Phe Asp Tyr
1               5

<210> SEQ ID NO 82

<400> SEQUENCE: 82

000

<210> SEQ ID NO 83

<400> SEQUENCE: 83

000

<210> SEQ ID NO 84
<211> LENGTH: 9
<212> TYPE: PRT
<213> ORGANISM: Mus Musculus

<400> SEQUENCE: 84

Ser Gln Gly Thr His Phe Pro Arg Thr
1               5

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91
<211> LENGTH: 8
<212> TYPE: PRT
<213> ORGANISM: Mus Musculus

<400> SEQUENCE: 91

Gly Tyr Thr Phe Ser Ser Tyr Trp
1               5

<210> SEQ ID NO 92
<211> LENGTH: 8
<212> TYPE: PRT
<213> ORGANISM: Mus Musculus

<400> SEQUENCE: 92

Ile Phe Pro Gly Ser Gly Ser Ala
1               5

<210> SEQ ID NO 93
<211> LENGTH: 11
<212> TYPE: PRT
<213> ORGANISM: Mus Musculus

<400> SEQUENCE: 93

Thr Ser Arg Trp Tyr Pro Asp Tyr Phe Glu Tyr
1               5                   10

<210> SEQ ID NO 94
<211> LENGTH: 11
<212> TYPE: PRT
<213> ORGANISM: Mus Musculus

<400> SEQUENCE: 94

Gln Ser Leu Val His Ser Asn Gly Asn Thr Tyr
1               5                   10

<210> SEQ ID NO 95

<400> SEQUENCE: 95

000

<210> SEQ ID NO 96
<211> LENGTH: 9
<212> TYPE: PRT
<213> ORGANISM: Mus Musculus

<400> SEQUENCE: 96

Ser Gln Ser Thr His Val Pro Tyr Thr
1               5

<210> SEQ ID NO 97
<211> LENGTH: 24
<212> TYPE: DNA
<213> ORGANISM: Mus Musculus

<400> SEQUENCE: 97
ggattcgatt ttagtagata ctgg                                          24

<210> SEQ ID NO 98
<211> LENGTH: 24
<212> TYPE: DNA
<213> ORGANISM: Mus Musculus

<400> SEQUENCE: 98
attaatccac atagcagtac gata                                          24

<210> SEQ ID NO 99
<211> LENGTH: 24
<212> TYPE: DNA
<213> ORGANISM: Mus Musculus

<400> SEQUENCE: 99
ggaagaggag actacgttga ctac                                          24

<210> SEQ ID NO 100
<211> LENGTH: 36
<212> TYPE: DNA
<213> ORGANISM: Mus Musculus

<400> SEQUENCE: 100
cagagccttt tatatagtag aaatcaaaag aactac                             36

<210> SEQ ID NO 101
<211> LENGTH: 9
<212> TYPE: DNA
<213> ORGANISM: Mus Musculus

<400> SEQUENCE: 101 tgggcatcc                                                            9

<210> SEQ ID NO 102
<211> LENGTH: 27
<212> TYPE: DNA
<213> ORGANISM: Mus Musculus

<400> SEQUENCE: 102
cagcaatatt atagctatcc tcggacg                                       27

<210> SEQ ID NO 103
<211> LENGTH: 30
<212> TYPE: DNA
<213> ORGANISM: Mus Musculus

<400> SEQUENCE: 103
gggttttcac tgagcacttc tggtatgggt                                    30

<210> SEQ ID NO 104
<211> LENGTH: 21
<212> TYPE: DNA

```
<213> ORGANISM: Mus Musculus

<400> SEQUENCE: 104
atttggtggg atggtgacaa g                                     21

<210> SEQ ID NO 105
<211> LENGTH: 36
<212> TYPE: DNA
<213> ORGANISM: Mus Musculus

<400> SEQUENCE: 105
actcgaatag tagttcctaa cttcctgttt acttac                     36

<210> SEQ ID NO 106
<211> LENGTH: 33
<212> TYPE: DNA
<213> ORGANISM: Mus Musculus

<400> SEQUENCE: 106
cagagcattg tacaaagtaa tggaaacacc tat                        33

<210> SEQ ID NO 107
<211> LENGTH: 9
<212> TYPE: DNA
<213> ORGANISM: Mus Musculus

<400> SEQUENCE: 107 aaagttccc                                                   9

<210> SEQ ID NO 108
<211> LENGTH: 27
<212> TYPE: DNA
<213> ORGANISM: Mus Musculus

<400> SEQUENCE: 108
tttcaaggtt cacatgttcc attcacg                               27

<210> SEQ ID NO 109
<211> LENGTH: 24
<212> TYPE: DNA
<213> ORGANISM: Mus Musculus

<400> SEQUENCE: 109
gggtatacct tcacaactgc tgga                                  24

<210> SEQ ID NO 110
<211> LENGTH: 24
<212> TYPE: DNA
<213> ORGANISM: Mus Musculus

<400> SEQUENCE: 110
ataaataccc actctggagt gcca                                  24

<210> SEQ ID NO 111
<211> LENGTH: 24
<212> TYPE: DNA
<213> ORGANISM: Mus Musculus

<400> SEQUENCE: 111
gcgagaactt cctgggctcc ttac                                  24

<210> SEQ ID NO 112
<211> LENGTH: 33
```

```
<212> TYPE: DNA
<213> ORGANISM: Mus Musculus

<400> SEQUENCE: 112
cagagcctct tagatagtga tggaaagaca tat                           33

<210> SEQ ID NO 113
<211> LENGTH: 9
<212> TYPE: DNA
<213> ORGANISM: Mus Musculus

<400> SEQUENCE: 113 ctggtgtct                                                      9

<210> SEQ ID NO 114
<211> LENGTH: 27
<212> TYPE: DNA
<213> ORGANISM: Mus Musculus

<400> SEQUENCE: 114
tggcaaggta cactttccc tcagacg                                   27

<210> SEQ ID NO 115
<211> LENGTH: 24
<212> TYPE: DNA
<213> ORGANISM: Mus Musculus

<400> SEQUENCE: 115
ggcttcaaca ttaaagacac ctat                                     24

<210> SEQ ID NO 116
<211> LENGTH: 24
<212> TYPE: DNA
<213> ORGANISM: Mus Musculus

<400> SEQUENCE: 116
attgatcctg cgaatggtaa tact                                     24

<210> SEQ ID NO 117
<211> LENGTH: 24
<212> TYPE: DNA
<213> ORGANISM: Mus Musculus

<400> SEQUENCE: 117
tctaactggg attactttga ctac                                     24

<210> SEQ ID NO 118

<400> SEQUENCE: 118

000

<210> SEQ ID NO 119

<400> SEQUENCE: 119

000

<210> SEQ ID NO 120
<211> LENGTH: 27
<212> TYPE: DNA
<213> ORGANISM: Mus Musculus

<400> SEQUENCE: 120
```

```
tcgcaaggta cacattttcc tcggacg                                    27
```

<210> SEQ ID NO 121

<400> SEQUENCE: 121

000

<210> SEQ ID NO 122

<400> SEQUENCE: 122

000

<210> SEQ ID NO 123
<211> LENGTH: 24
<212> TYPE: DNA
<213> ORGANISM: Mus Musculus

<400> SEQUENCE: 123

```
tcgaactggg attactttga ctac                                       24
```

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127
<211> LENGTH: 24
<212> TYPE: DNA
<213> ORGANISM: Mus Musculus

<400> SEQUENCE: 127

```
ggctacacat tcagtagtta ctgg                                       24
```

<210> SEQ ID NO 128
<211> LENGTH: 24
<212> TYPE: DNA
<213> ORGANISM: Mus Musculus

<400> SEQUENCE: 128

```
attttccctg gaagtggtag tgct                                       24
```

<210> SEQ ID NO 129
<211> LENGTH: 33
<212> TYPE: DNA
<213> ORGANISM: Mus Musculus

<400> SEQUENCE: 129

```
acaagtagat ggtatcctga ctactttgaa tat                             33
```

<210> SEQ ID NO 130

-continued

```
<211> LENGTH: 33
<212> TYPE: DNA
<213> ORGANISM: Mus Musculus

<400> SEQUENCE: 130
cagagccttg tacacagtaa tggaaacacc tat                                    33

<210> SEQ ID NO 131

<400> SEQUENCE: 131

000

<210> SEQ ID NO 132
<211> LENGTH: 27
<212> TYPE: DNA
<213> ORGANISM: Mus Musculus

<400> SEQUENCE: 132
tctcaaagta cacatgttcc gtacacg                                           27

<210> SEQ ID NO 133
<211> LENGTH: 115
<212> TYPE: PRT
<213> ORGANISM: Mus Musculus

<400> SEQUENCE: 133
```

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Asn Trp Val Arg Gln Ala Pro Gly Lys Gly Leu Glu Trp Ile
        35                  40                  45

Gly Glu Ile Asn Pro His Ser Ser Thr Ile Asn Tyr Ala Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Gly Arg Gly Asp Tyr Val Asp Tyr Trp Gly Leu Gly Thr Thr Leu Thr
            100                 105                 110

Val Ser Ser
        115

```
<210> SEQ ID NO 134
<211> LENGTH: 113
<212> TYPE: PRT
<213> ORGANISM: Mus Musculus

<400> SEQUENCE: 134
```

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Arg Asn Gln Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

-continued

Ile Ser Ser Val Lys Ala Asp Asp Leu Ala Val Tyr Tyr Cys Gln Gln
                85                  90                  95

Tyr Tyr Ser Tyr Pro Arg Thr Phe Gly Gly Gly Thr Lys Leu Glu Ile
            100                 105                 110

Lys

<210> SEQ ID NO 135
<211> LENGTH: 120
<212> TYPE: PRT
<213> ORGANISM: Mus Musculus

<400> SEQUENCE: 135

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Gly Asp Lys Arg Tyr Asn Pro Ala
50                  55                  60

Leu Arg Ser Arg Leu Thr Ile Ser Lys Asp Thr Ser Ser Asn Gln Val
65                  70                  75                  80

Phe Leu Lys Ile Ala Ser Val Asp Thr Ala Asp Thr Ala Thr Tyr Tyr
                85                  90                  95

Cys Thr Arg Ile Val Val Pro Asn Phe Leu Phe Thr Tyr Trp Gly Gln
            100                 105                 110

Gly Thr Leu Val Thr Val Ser Ala
            115                 120

<210> SEQ ID NO 136
<211> LENGTH: 112
<212> TYPE: PRT
<213> ORGANISM: Mus Musculus

<400> SEQUENCE: 136

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val Gln Ser
            20                  25                  30

Asn Gly Asn Thr Tyr Leu Glu Trp Tyr Leu Gln Lys Pro Gly Gln Ser
        35                  40                  45

Pro Asn Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
            100                 105                 110

<210> SEQ ID NO 137
<211> LENGTH: 115
<212> TYPE: PRT
<213> ORGANISM: Mus Musculus

<400> SEQUENCE: 137

Gln Ile Gln Leu Val Gln Ser Gly Pro Glu Leu Arg Lys Pro Gly Glu

```
            1               5                  10                 15
Thr Val Arg Ile Ser Cys Lys Ala Ser Gly Tyr Thr Phe Thr Thr Ala
                20                  25                  30
Gly Met Gln Trp Val Gln Lys Met Pro Gly Lys Gly Leu Lys Trp Ile
                35                  40                  45
Gly Trp Ile Asn Thr His Ser Gly Val Pro Lys Tyr Ala Glu Asp Phe
        50                  55                  60
Lys Gly Arg Phe Ala Phe Ser Leu Glu Thr Ser Ala Ser Thr Ala Tyr
65                  70                  75                  80
Leu Gln Ile Ser Asn Leu Lys Asn Glu Asp Thr Ala Thr Tyr Phe Cys
                85                  90                  95
Ala Arg Thr Ser Trp Ala Pro Tyr Trp Gly Gln Gly Thr Leu Val Thr
                100                 105                 110
Val Ser Ala
        115

<210> SEQ ID NO 138
<211> LENGTH: 112
<212> TYPE: PRT
<213> ORGANISM: Mus Musculus

<400> SEQUENCE: 138

Asp Val Val Met Thr Gln Thr Pro Leu Thr Leu Ser Val Thr Ile Gly
1               5                   10                  15
Gln Pro Ala Ser Ile Ser Cys Lys Ser Ser Gln Ser Leu Leu Asp Ser
                20                  25                  30
Asp Gly Lys Thr Tyr Leu Asn Trp Leu Leu Gln Arg Pro Gly Gln Ser
                35                  40                  45
Pro Lys Arg Leu Ile Tyr Leu Val Ser Lys Leu Asp Ser Gly Val Pro
        50                  55                  60
Asp Arg Phe Thr Gly Ser Gly Ser Gly Thr Asp Phe Thr Leu Lys Ile
65                  70                  75                  80
Ser Arg Val Glu Ala Glu Asp Leu Gly Val Tyr Tyr Cys Trp Gln Gly
                85                  90                  95
Thr His Phe Pro Gln Thr Phe Gly Gly Gly Thr Lys Leu Glu Ile Lys
                100                 105                 110

<210> SEQ ID NO 139
<211> LENGTH: 116
<212> TYPE: PRT
<213> ORGANISM: Mus Musculus

<400> SEQUENCE: 139

Ser Glu Val Gln Leu Gln Gln Ser Gly Ala Glu Leu Val Lys Pro Gly
1               5                   10                  15
Ala Ser Val Lys Leu Ser Cys Thr Ala Ser Gly Phe Asn Ile Lys Asp
                20                  25                  30
Thr Tyr Ile His Trp Met Lys Gln Arg Pro Glu Gln Gly Leu Glu Trp
                35                  40                  45
Ile Gly Arg Ile Asp Pro Ala Asn Gly Asn Thr Lys Tyr Asp Pro Glu
        50                  55                  60
Phe Gln Asp Lys Ala Thr Ile Ala Ala Asp Thr Ser Ser Asn Thr Ala
65                  70                  75                  80
Tyr Leu Gln Leu Ser Ser Leu Thr Ser Glu Asp Thr Ala Val Tyr Tyr
                85                  90                  95
Cys Ser Asn Trp Asp Tyr Phe Asp Tyr Trp Gly Gln Gly Thr Ala Leu
```

100                 105                 110

Thr Val Ser Ser
        115

<210> SEQ ID NO 140
<211> LENGTH: 112
<212> TYPE: PRT
<213> ORGANISM: Mus Musculus

<400> SEQUENCE: 140

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Ser Gln Gly
                85                  90                  95

Thr His Phe Pro Arg Thr Phe Gly Gly Gly Thr Lys Leu Glu Ile Lys
            100                 105                 110

<210> SEQ ID NO 141
<211> LENGTH: 115
<212> TYPE: PRT
<213> ORGANISM: Mus Musculus

<400> SEQUENCE: 141

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Thr Asn Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Phe Ser Ser Leu Thr Ser Glu Asp Thr Ala Val Tyr Tyr Cys
                85                  90                  95

Ser Asn Trp Asp Tyr Phe Asp Tyr Trp Gly Gln Gly Thr Thr Leu Thr
            100                 105                 110

Val Ser Ser
        115

<210> SEQ ID NO 142
<211> LENGTH: 112
<212> TYPE: PRT
<213> ORGANISM: Mus Musculus

<400> SEQUENCE: 142

Asp Val Val Leu Thr Gln Thr Pro Leu Thr Leu Ser Val Thr Ile Gly
1               5                   10                  15

Gln Pro Ala Ser Ile Pro Cys Lys Ser Ser Gln Ser Leu Leu Asp Ser
            20                  25                  30

```
Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Ser Gln Gly
                 85                  90                  95

Thr His Phe Pro Arg Thr Phe Gly Gly Gly Thr Lys Leu Glu Ile Lys
                100                 105                 110

<210> SEQ ID NO 143
<211> LENGTH: 118
<212> TYPE: PRT
<213> ORGANISM: Mus Musculus

<400> SEQUENCE: 143

Gln Val Gln Leu Gln Gln Ser Gly Ala Glu Leu Met Lys Pro Gly Ala
 1               5                  10                  15

Ser Val Lys Ile Ser Cys Lys Ala Thr Gly Tyr Thr Phe Ser Ser Tyr
                 20                  25                  30

Trp Val Glu Trp Val Lys Leu Arg Pro Gly His Gly Leu Glu Trp Ile
            35                  40                  45

Gly Glu Ile Phe Pro Gly Ser Gly Ser Ala Asn Tyr Asn Glu Lys Phe
 50                  55                  60

Lys Gly Lys Ala Thr Phe Thr Ala Asp Thr Ser Ser Asn Thr Ala Tyr
 65                  70                  75                  80

Met Gln Leu Ser Ser Leu Thr Ser Glu Asp Ser Ala Val Tyr Tyr Cys
                 85                  90                  95

Thr Ser Arg Trp Tyr Pro Asp Tyr Phe Glu Tyr Trp Gly Gln Gly Thr
                100                 105                 110

Thr Leu Thr Val Ser Ser
            115

<210> SEQ ID NO 144
<211> LENGTH: 112
<212> TYPE: PRT
<213> ORGANISM: Mus Musculus

<400> SEQUENCE: 144

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
                 20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Tyr Thr Phe Gly Gly Gly Thr Lys Leu Glu Ile Arg
                100                 105                 110

<210> SEQ ID NO 145
```

```
<211> LENGTH: 345
<212> TYPE: DNA
<213> ORGANISM: Mus Musculus

<400> SEQUENCE: 145
gaggtgaagc ttctcgagtc tggaggtggc ctggtgcagc ctggaggatc cctgaaactc      60
tcctgtgcag cctcaggatt cgattttagt agatactgga tgaattgggt ccggcaggct     120
ccagggaaag gctagaatg gattggagaa attaatccac atagcagtac gataaactat      180
gcgccatctc taaaggataa attcatcatc tccagagaca acgccaaaaa tacgctgtac     240
ctgcaaatga gcaaagtgag atctgaggac acagcccttt attactgtgg aagaggagac     300
tacgttgact actggggcct aggcaccact ctcacagtct cctca                     345

<210> SEQ ID NO 146
<211> LENGTH: 339
<212> TYPE: DNA
<213> ORGANISM: Mus Musculus

<400> SEQUENCE: 146
gacattgtga tgtcacagtc tccatcctcc ctagctgtgt cagttggaga gaaggttact      60
atgagctgca gtccagtca gagccttta tatagtagaa atcaaaagaa ctacttggcc      120
tggtaccagc agaaaccagg gcagtctcct aaactgctga tttactgggc atccactagg     180
gaatctgggg tccctgatcg cttcacaggc agtggatctg gacagatttt cactctcacc     240
atcagcagtg tgaaggctga tgacctggca gtttattact gtcagcaata ttatagctat     300
cctcggacgt tcggtggagg caccaagctg gaaatcaaa                            339

<210> SEQ ID NO 147
<211> LENGTH: 360
<212> TYPE: DNA
<213> ORGANISM: Mus Musculus

<400> SEQUENCE: 147
caggttactc tgaaagagtc tggccctggg atattgcagc cctcccagac cctcagtctg      60
acttgttctt tctctgggtt ttcactgagc acttctggta tgggtgtagg ctggattcgt     120
cagccttcag ggaagggtct ggagtggctg gcacacattt ggtgggatgg tgacaagcgc     180
tataacccag ccctgaggag ccgactgaca atctccaagg atacctccag caaccaggtt     240
ttcctcaaga tcgccagtgt ggacactgca gatactgcca catactactg tactcgaata     300
gtagttccta acttcctgtt tacttactgg ggccaaggga ctctggtcac tgtctctgca     360

<210> SEQ ID NO 148
<211> LENGTH: 336
<212> TYPE: DNA
<213> ORGANISM: Mus Musculus

<400> SEQUENCE: 148
gatgttttga tgacccaaac tccactctcc ctgcctgtca gtcttggaga tcaagcctcc      60
atctcttgca gatctagtca gagcattgta caaagtaatg gaaacaccta tttagaatgg     120
tacttgcaga aaccaggcca gtctccaaac ctcctgatct caaagtttc caaccgattt      180 tctggggtcc cagacaggtt cagtggcagt ggatcaggga cagatttcac actcaagatc     240
agcagagtgg aggctgagga tctgggagtt tattactgct ttcaaggttc acatgttcca     300
ttcacgttcg gctcggggac aaagttggaa ataaaa                               336
```

```
<210> SEQ ID NO 149
<211> LENGTH: 345
<212> TYPE: DNA
<213> ORGANISM: Mus Musculus

<400> SEQUENCE: 149
cagatccagt tggtgcagtc tggacctgag ctgaggaagc tggagagac  agtcaggatc      60
tcctgcaagg cttctgggta taccttcaca actgctggaa tgcagtgggt gcaaaagatg     120
ccaggaaagg gtttgaagtg gattggctgg ataaataccc actctggagt gccaaaatat     180
gcagaagact tcaagggacg gtttgccttc tctttggaaa cctccgccag cactgcatat     240
ttacagataa gcaacctcaa aaatgaggac acggctacgt atttctgtgc gagaacttcc     300
tgggctcctt actggggcca aggactctg  gtcactgtct ctgca                     345

<210> SEQ ID NO 150
<211> LENGTH: 336
<212> TYPE: DNA
<213> ORGANISM: Mus Musculus

<400> SEQUENCE: 150
gatgttgtga tgacccagac tccactcact ttgtcggtta ccattggaca accagcctcc      60
atctcttgca agtcaagtca gagcctctta gatagtgatg gaaagacata tttgaattgg     120
ttgttacaga ggccaggcca gtctccaaag cgcctaatct atctggtgtc taaactggac     180
tctggagtcc ctgacaggtt cactggcagt ggatcaggga cagacttcac actgaaaatc     240
agcagagtgg aggctgagga tttgggagtt tattattgct ggcaaggtac acattttcct     300
cagacgttcg gtggaggcac caagctggaa atcaaa                              336

<210> SEQ ID NO 151
<211> LENGTH: 345
<212> TYPE: DNA
<213> ORGANISM: Mus Musculus

<400> SEQUENCE: 151
gaggttcagc tgcagcagtc tggggcagaa cttgtgaagc caggggcctc agtcaagttg      60
tcctgcacag cttctggctt caacattaaa gacacctata tacactggat gaagcagagg     120
cctgaacagg gcctggagtg gattggaagg attgatcctg cgaatggtaa tactaaatat     180
gacccggagt tccaggacaa ggccactata gcagcagaca catcctccaa cacagcctac     240
ctgcagctca gcagcctgac atctgaggac actgccgtct attactgttc taactgggat     300
tactttgact actggggcca aggcaccgct ctcacagtct cctca                     345

<210> SEQ ID NO 152
<211> LENGTH: 336
<212> TYPE: DNA
<213> ORGANISM: Mus Musculus

<400> SEQUENCE: 152
gatgttgtga tgacccagac tccactcact ttgtcggtta ccattggaca gccagcctcc      60
atctcttgca agtcaagtca gagcctctta gatagtgatg gaaagacata tttgaattgg     120
ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct cgcaaggtac acattttcct     300
cggacgttcg gtggaggcac caagctggaa atcaaa                              336
```

<210> SEQ ID NO 153
<211> LENGTH: 345
<212> TYPE: DNA
<213> ORGANISM: Mus Musculus

<400> SEQUENCE: 153
gaggttcagc tgcagcagtc tggggcagaa cttgtgaagc caggggcctc agtcaagttg      60
tcctgcacag cttctggctt caacattaaa gacacctata tacactgggt gaagcagagg     120
cctgaacagg gcctggagtg gattggaagg attgatcctg cgaatggtaa tactaattat     180
gacccgaagt tccaggacaa ggccactata acagcagaca catcctccaa cacagcctac     240
ctgcagttca gcagcctgac atctgaggac actgccgtct attactgttc gaactgggat     300
tactttgact actggggcca aggcaccact ctcacagtct cctca                     345

<210> SEQ ID NO 154
<211> LENGTH: 336
<212> TYPE: DNA
<213> ORGANISM: Mus Musculus

<400> SEQUENCE: 154
gatgttgtgc tgacccagac tccactcact ttgtcggtta ccattggaca gccagcctcc      60
atcccttgca gtcaagtca gagcctctta gatagtgatg aaagacata tttgaattgg       120 ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct cgcaaggtac acattttcct     300
cggacgttcg gtggaggcac caagctggaa atcaaa                              336

<210> SEQ ID NO 155
<211> LENGTH: 354
<212> TYPE: DNA
<213> ORGANISM: Mus Musculus

<400> SEQUENCE: 155
caggttcagc tgcagcagtc tggagctgag ctgatgaagc ctggggcctc agtgaagata      60
tcctgcaagg ctactggcta cacattcagt agttactggg tagagtgggt aaagctgagg     120
cctggacatg gccttgagtg gattggagag attttccctg gaagtggtag tgctaattac     180
aatgagaagt tcaagggcaa ggccacattc actgcagata catcctccaa cacagcctac     240
atgcaactca gcagcctgac atctgaggat tctgccgtct attactgtac aagtagatgg     300
tatcctgact actttgaata ttggggccaa ggcaccactc tcacagtctc ctca           354

<210> SEQ ID NO 156
<211> LENGTH: 336
<212> TYPE: DNA
<213> ORGANISM: Mus Musculus

<400> SEQUENCE: 156
gatgttgtga tgacccaaac tccactctcc ctgcctgtca gtcttggaga tcaagcctcc      60
atctcttgca gatctagtca gagccttgta cacagtaatg aaacaccta tttacattgg     120 tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttccg     300
tacacgttcg gagggggac caagctggaa ataaga                               336

<210> SEQ ID NO 157
<211> LENGTH: 19
<212> TYPE: PRT
<213> ORGANISM: Mus Musculus

<400> SEQUENCE: 157

Met Glu Trp Thr Trp Val Phe Leu Phe Leu Leu Ser Val Thr Ala Gly
1               5                   10                  15

Gly His Ser

<210> SEQ ID NO 158
<211> LENGTH: 20
<212> TYPE: PRT
<213> ORGANISM: Mus Musculus

<400> SEQUENCE: 158

Met Asp Ser Gln Ala Gln Val Leu Met Leu Leu Leu Leu Trp Val Ser
1               5                   10                  15

Gly Thr Cys Gly
            20

<210> SEQ ID NO 159
<211> LENGTH: 19
<212> TYPE: PRT
<213> ORGANISM: Mus Musculus

<400> SEQUENCE: 159

Met Gly Arg Leu Thr Ser Ser Phe Leu Leu Leu Ile Val Pro Ala Tyr
1               5                   10                  15

Val Leu Ser

<210> SEQ ID NO 160
<211> LENGTH: 19
<212> TYPE: PRT
<213> ORGANISM: Mus Musculus

<400> SEQUENCE: 160

Met Lys Leu Pro Val Arg Leu Leu Val Leu Met Phe Trp Ile Pro Ala
1               5                   10                  15

Ser Ser Ser

<210> SEQ ID NO 161
<211> LENGTH: 19
<212> TYPE: PRT
<213> ORGANISM: Mus Musculus

<400> SEQUENCE: 161

Met Glu Trp Leu Trp Asn Leu Leu Phe Leu Met Ala Ala Ala Gln Ser
1               5                   10                  15

Ile Gln Ala

<210> SEQ ID NO 162
<211> LENGTH: 19
<212> TYPE: PRT
<213> ORGANISM: Mus Musculus

<400> SEQUENCE: 162

Met Ser Pro Ala Gln Phe Leu Phe Leu Leu Val Phe Trp Ile Arg Glu
1               5                   10                  15

Thr Asn Gly

<210> SEQ ID NO 163
<211> LENGTH: 18
<212> TYPE: PRT
<213> ORGANISM: Mus Musculus

<400> SEQUENCE: 163

Met Lys Cys Ser Trp Val Ile Phe Phe Leu Met Ala Val Val Thr Gly
1               5                   10                  15

Val Asn

<210> SEQ ID NO 164
<211> LENGTH: 19
<212> TYPE: PRT
<213> ORGANISM: Mus Musculus

<400> SEQUENCE: 164

Met Ser Pro Ala Gln Phe Leu Phe Leu Leu Val Leu Trp Ile Arg Glu
1               5                   10                  15

Thr Asn Gly

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169
<211> LENGTH: 54
<212> TYPE: DNA
<213> ORGANISM: Mus Musculus

<400> SEQUENCE: 169
atggattttg ggctgatttt ttttattgtt gctcttttaa aagggtccca gtgt          54

<210> SEQ ID NO 170
<211> LENGTH: 60
<212> TYPE: DNA
<213> ORGANISM: Mus Musculus

<400> SEQUENCE: 170
atggattcac aggcccaggt tcttatgtta ctgctgctat gggtatctgg tacctgtggg    60

<210> SEQ ID NO 171
<211> LENGTH: 57
<212> TYPE: DNA

<213> ORGANISM: Mus Musculus

<400> SEQUENCE: 171
atgggcaggc ttacttcttc attcttgcta ctgattgtcc ctgcatatgt cctgtcc          57

<210> SEQ ID NO 172
<211> LENGTH: 57
<212> TYPE: DNA
<213> ORGANISM: Mus Musculus

<400> SEQUENCE: 172
atgaagttgc ctgttaggct gttggtgctg atgttctgga ttcctgcttc cagcagt          57

<210> SEQ ID NO 173
<211> LENGTH: 57
<212> TYPE: DNA
<213> ORGANISM: Mus Musculus

<400> SEQUENCE: 173
atggaatggc tgtggaactt gctatttctc atggcagcag ctcaaagtat ccaagca          57

<210> SEQ ID NO 174
<211> LENGTH: 57
<212> TYPE: DNA
<213> ORGANISM: Mus Musculus

<400> SEQUENCE: 174
atgagtcctg cccagttcct gtttctgtta gtgttctgga ttcgggaaac caacggt          57

<210> SEQ ID NO 175
<211> LENGTH: 57
<212> TYPE: DNA
<213> ORGANISM: Mus Musculus

<400> SEQUENCE: 175
atgaaatgca gctgggttat cttcttcctg atggcagtgg ttacaggggt caattca          57

<210> SEQ ID NO 176
<211> LENGTH: 57
<212> TYPE: DNA
<213> ORGANISM: Mus Musculus

<400> SEQUENCE: 176
atgagtcctg cccagttcct gtttctgtta gtgctctgga ttcgggaaac caacggt          57

<210> SEQ ID NO 177
<211> LENGTH: 57
<212> TYPE: DNA
<213> ORGANISM: Mus Musculus

<400> SEQUENCE: 177
atgaaatgca gctgggttat cttcttcctg atggcagtgg ttacaggggt caattcg          57

<210> SEQ ID NO 178
<211> LENGTH: 57
<212> TYPE: DNA
<213> ORGANISM: Mus Musculus

<400> SEQUENCE: 178
atgagtcctg cccagttcct gtttctgtta gtgctctgga ttcgggaaac caacggt          57

<210> SEQ ID NO 179
<211> LENGTH: 57

```
<212> TYPE: DNA
<213> ORGANISM: Mus Musculus

<400> SEQUENCE: 179
atggaatgga cctgggtctt tctcttcctc ctgtcagtaa ctgcaggtgg ccactcc      57

<210> SEQ ID NO 180
<211> LENGTH: 8
<212> TYPE: PRT
<213> ORGANISM: Mus Musculus

<400> SEQUENCE: 180

Gly Phe Asn Ile Lys Asp Tyr Tyr
1               5

<210> SEQ ID NO 181
<211> LENGTH: 8
<212> TYPE: PRT
<213> ORGANISM: Mus Musculus

<400> SEQUENCE: 181

Ile Asp Pro Glu Asn Asp Asn Thr
1               5

<210> SEQ ID NO 182
<211> LENGTH: 7
<212> TYPE: PRT
<213> ORGANISM: Mus Musculus

<400> SEQUENCE: 182

Ala Met Gly Gly Phe Thr Tyr
1               5

<210> SEQ ID NO 183
<211> LENGTH: 11
<212> TYPE: PRT
<213> ORGANISM: Mus Musculus

<400> SEQUENCE: 183

Gln Ser Leu Leu His Ser Asp Gly Lys Thr Tyr
1               5                   10

<210> SEQ ID NO 184
<211> LENGTH: 9
<212> TYPE: PRT
<213> ORGANISM: Mus Musculus

<400> SEQUENCE: 184

Trp Gln Gly Thr His Phe Pro Arg Thr
1               5

<210> SEQ ID NO 185
<211> LENGTH: 24
<212> TYPE: DNA
<213> ORGANISM: Mus Musculus

<400> SEQUENCE: 185
ggcttcaaca ttaaagacta ctat                                          24

<210> SEQ ID NO 186
<211> LENGTH: 24
<212> TYPE: DNA
<213> ORGANISM: Mus Musculus

<400> SEQUENCE: 186
```

-continued

```
attgatcctg agaatgataa tact                                              24

<210> SEQ ID NO 187
<211> LENGTH: 21
<212> TYPE: DNA
<213> ORGANISM: Mus Musculus

<400> SEQUENCE: 187
gctatggggg gttttactta c                                                 21

<210> SEQ ID NO 188
<211> LENGTH: 33
<212> TYPE: DNA
<213> ORGANISM: Mus Musculus

<400> SEQUENCE: 188
cagagcctct tacatagtga tggaaagaca tat                                    33

<210> SEQ ID NO 189
<211> LENGTH: 27
<212> TYPE: DNA
<213> ORGANISM: Mus Musculus

<400> SEQUENCE: 189
tggcaaggta cacattttcc tcggacg                                           27

<210> SEQ ID NO 190
<211> LENGTH: 114
<212> TYPE: PRT
<213> ORGANISM: Mus Musculus

<400> SEQUENCE: 190
```

Glu Val Gln Leu Gln Gln Ser Gly Ala Glu Leu Val Arg Pro Gly Ala
1               5                   10                  15

Leu Val Lys Leu Ser Cys Lys Gly Ser Gly Phe Asn Ile Lys Asp Tyr
            20                  25                  30

Tyr Met Ser Trp Val Lys Gln Arg Pro Glu Gln Gly Leu Glu Trp Ile
        35                  40                  45

Gly Trp Ile Asp Pro Glu Asn Asp Asn Thr Ile Tyr Asp Ser Lys Phe
    50                  55                  60

Gln Gly Lys Ala Ser Ile Thr Ala Asp Thr Ser Ser Asn Thr Ala Tyr
65                  70                  75                  80

Leu Gln Phe Ser Ser Leu Thr Pro Glu Asp Thr Ala Val Tyr Tyr Cys
                85                  90                  95

Ala Met Gly Gly Phe Thr Tyr Trp Gly Gln Gly Thr Leu Val Thr Val
            100                 105                 110

Ser Ala

```
<210> SEQ ID NO 191
<211> LENGTH: 112
<212> TYPE: PRT
<213> ORGANISM: Mus Musculus

<400> SEQUENCE: 191
```

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Asn Trp Leu Leu Gln Arg Pro Gly Gln Ser

-continued

```
                35                    40                    45
Pro Lys Arg Leu Ile Tyr Leu Val Ser Lys Leu Asp Ser Gly Val Pro
    50                    55                    60

Asp Arg Phe Thr Gly Ser Gly Ser Gly Thr Asp Phe Thr Leu Lys Ile
65                  70                    75                    80

Ser Arg Val Glu Ala Glu Asp Leu Gly Val Tyr Tyr Cys Trp Gln Gly
                85                    90                    95

Thr His Phe Pro Arg Thr Phe Gly Gly Gly Thr Lys Leu Glu Ile Lys
                100                   105                   110

<210> SEQ ID NO 192
<211> LENGTH: 342
<212> TYPE: DNA
<213> ORGANISM: Mus Musculus

<400> SEQUENCE: 192
gaggttcagc tgcagcagtc tggggctgag cttgtgaggc caggggcctt agtcaagttg      60
tcctgcaaag gttctggctt caacattaaa gactactata tgagttgggt gaagcagagg     120
cctgaacagg gcctggaatg gattggatgg attgatcctg agaatgataa tactatatat     180
gactcgaagt tccagggcaa ggccagtata acagcagaca cttcctccaa cacagcctac     240
ctgcagttca gcagcctgac acctgaggac actgccgtct attactgtgc tatgggggt      300 tttacttact ggggccaagg gactctggtc actgtctctg ca                        342

<210> SEQ ID NO 193
<211> LENGTH: 336
<212> TYPE: DNA
<213> ORGANISM: Mus Musculus

<400> SEQUENCE: 193
gatgttgtga tgacccagac tccactcact ttgtcggtta ccattggaca accagcctcc      60
atctcttgca agtcaagtca gagcctctta catagtgatg gaaagacata tttgaattgg     120
ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct ggcaaggtac acatttcct     300 cggacgttcg gtggaggcac caagctggaa atcaaa                               336
```

CONFORMATION-SPECIFIC EPITOPES IN ALPHA-SYNUCLEIN, ANTIBODIES THERETO AND METHODS RELATED THEREOF

CROSS REFERENCE TO RELATED APPLICATIONS

The present application is a PCT application and claims priority from U.S. provisional application No. 62/742,408 filed on Oct. 7, 2018, U.S. provisional application No. 62/780,599 filed on Dec. 17, 2018, U.S. provisional application No. 62/820,701 filed on Mar. 19, 2019, and U.S. provisional application No. 62/864,060 filed on Jun. 20, 2019, each of which are hereby incorporated by reference in their entirety.

FIELD

The present disclosure relates to alpha-synuclein (also referred to as α-syn or α-synuclein) epitopes and antibodies thereto, and more specifically to conformational alpha-synuclein epitopes that are selectively accessible in disease related alpha-synuclein, and related antibody compositions and uses thereof.

BACKGROUND

Alpha-synuclein (α-syn or α-synuclein), is a 140 amino acid protein found mainly in the presynaptic terminals of neurons, and is thought to play functional roles in maintaining the supply of synaptic vesicles in presynaptic terminals by clustering synaptic vesicles, and in regulating the release of dopamine [eLife 2013;2:e00592 doi: 10.7554/eLife.00592]. At least three isoforms of synuclein are produced through alternative splicing. The most common form of the protein is the full-length protein of 140 amino acids. Other isoforms are α-syn-126, which lacks residues 41-54 due to loss of exon 3, and α-syn-112, which lacks residue 103-130 due to loss of exon 5.

Monomeric alpha-synuclein in solution is considered to be an intrinsically disordered protein, lacking a single stable 3D structure. N-terminal residues 1-60 of α-syn are amphipathic and contain four 11-residue repeats including the consensus sequence KTKEGV (SEQ ID NO: 6). This sequence has a structural alpha helix propensity similar to apolipoprotein-binding domains. Residues 61-95 constitute a central hydrophobic region which is referred to as the non-amyloid-β component or NAC region, and is known to be involved in protein aggregation [PNAS Dec. 1, 1993 90 (23) 11282-11286; doi.org/10.1073/pnas.90.23.11282]. Residues 96-140 constitute a highly acidic and proline-rich region with no distinct structural propensity.

The α-syn monomer in solution is intrinsically disordered. The monomer bound to membranes has partial helical structure [Ulmer, T. S., Bax, A., Cole, N. B., Nussbaum, R. L (2005) J Biol Chem 280 9595-9603; Rao, J. N., Jao, C. C., Hegde, B. G., Langen, R., Ulmer, T. S. (2010) J Am Chem Soc 132 8657-8668]. α-syn monomers bound to membranes induce curvature in the membrane [Varkey et al. J Biol Chem v285, no. 42, pp32486-32493, (2010) DOI: 10.1074/jbc.M110.139576]. α-Synuclein may exist in a stably folded tetramer that resists aggregation [doi:10.1038/nature10324] or as a monomer, at least in the CNS (Fauvet et al., 2012, DOI: 10.1074/jbc.M111.318949).

It has been recently shown that a Parkinson's-like disease develops in mice expressing a mutant alpha-syn that cannot tetramerize (Nuber et al, 2018).

Under pathological conditions associated with Parkinson's disease, dementia with Lewy bodies, and multiple system atrophy (collectively known as synucleinopathies), α-synuclein aggregates to form insoluble fibrils characteristic of Lewy bodies and Lewy neurites. Alpha-synuclein is the primary structural component of Lewy body fibrils. Alpha-synuclein pathology is also found in both sporadic and familial cases with Alzheimer's disease [doi:10.1007/s00401-002-0596-7]. Point mutations in the gene for α-Syn are associated with inherited forms of Parkinson's disease, including A53T, A30P, E46K, H50Q, and G51D. Overexpression by genomic duplication and triplication of the SNCA gene encoding α-Syn also appear to cause Parkinson's disease.

Alpha-synuclein pathological aggregates located in the presynapse are thought to be a cause of synaptic dysfunction [doi:10.1007/s00401-010-0711-0]. Small molecule compounds that inhibit aggregation of alpha-synuclein have thus been developed as a strategy for treating synucleinopathies [REF DOI: 10.1021/bi0600749].

Antibodies that specifically recognize phospho-S129 of α-synuclein immunostain Lewy bodies, indicating S129 is selectively and extensively phosphorylated in synucleinopathy lesions.

Antibodies have been raised to alpha-synuclein and immunogens related thereto described.

U.S. Patent Publication No. US20160244515A1 describes human anti-alpha-synuclein antibodies.

U.S. Patent Publication No. US20150232524A1 discloses compositions, comprising one or more immunogens having at least two regions including an alpha-synuclein B cell epitope and at least one T helper cell epitope.

U.S. Patent Publication No. US20140295465A1 describes use of an anti-alpha synuclein antibody to diagnose an elevated level of alpha synuclein in the brain.

Oligomeric alpha-synuclein may be a form of the protein that causes neuronal death [Brown DR 2010, DOI: 10.1002/iub.316]. α-Syn has been detected in the cerebrospinal fluid (CSF) of Parkinson's disease patients. Oligomers, thought to be formed as prefibrillar intermediates, may be the preferentially toxic component of α-Syn [Karpinar et al. 2009, DOI: 10.1038/emboj.2009.257]. Pre-fibrillar alpha-synuclein variants with impaired beta-structure increase neuro-toxicity in Parkinson's disease models [EMBO J. 28, 3256-3268; Outeiro . . . McLean, (2008)]. Formation of toxic oligomeric alpha-synuclein species can occur intracellularly in living cells [PLoS ONE 3, e1867; Danzer . . . Kostka, (2007)]. Different species of alpha-synuclein oligomers induce calcium influx and seeding [J. Neurosci. 27, 9220-9232].

Oligomers have no well-defined structure and are conformationally plastic, and are present at concentrations far below that of the functional monomer or tetramer. The low concentration of misfolded, oligomeric alpha-syn makes this target elusive. Antibodies or drugs targeting healthy alpha-syn could be harmful for the cell.

Attempts to raise antibodies for oligomeric alpha-synuclein have been reported. U.S. Patent Publication No. US20160199522A1 reports raising antibodies using preparations of soluble protofibril/oligomer human alpha-synuclein modified with 4-hydroxy-2-nonenal (HNE) or alpha, beta-unsaturated alkenal 4-oxo-2-nonenal (ONE). No evidence of their usefulness for human samples was provided.

The survival of neurons with intracellular Lewy bodies suggests that the presence of intracytoplasmic α-Syn aggregates is not grossly toxic to all cells [Spillantini et. al (1997) Alpha-synuclein in Lewy bodies. Nature 388, 839-840].

Fibril structures of full length human α-synuclein have been obtained by solid-state NMR (PDB 2N0A) [doi: 10.1038/nsmb.3194, Solid-state NMR structure of a pathogenic fibril of full-length human α-synuclein, Tuttle et al Nature SMB 2016].

Antibodies that preferentially or selectively bind misfolded oligomeric alpha-synuclein over monomeric α-Syn, and/or insoluble fibrillar α-Syn, are desirable.

SUMMARY

Described herein are conformational epitopes in misfolded oligomeric α-synuclein.

An aspect includes a cyclic compound comprising an α-synuclein peptide comprising and/or consisting of 3 or more residues of EKTKEQ (SEQ ID NO: 1), optionally comprising and/or consisting of residues EKTK (SEQ ID NO: 2) or a part thereof, of residues KTKE (SEQ ID NO: 3) or a part thereof, or of residues TKEQ (SEQ ID NO: 4) or a part thereof, the part thereof comprising at least 3 amino acids.

The α-synuclein peptides incorporated into the cyclic compound are conformational epitopes and can be used as immunogens. The epitopes are selectively exposed in misfolded oligomeric species of α-synuclein, and for example unavailable or less available in natively folded α-synuclein monomer and/or native tetramer.

Another aspect includes an antibody that specifically binds an epitope in the α-Syn peptide of the cyclic compound described herein and/or in misfolded oligomeric α-synuclein compared to a corresponding linear compound and/or a native α-Syn and/or insoluble fibrillar α-Syn. The antibody may be raised using an immunogen or composition comprising an immunogen described herein.

The epitope is a conformational epitope, for example, the epitope is selectively presented or accessible in misfolded oligomeric α-Syn. The α-Syn peptide can be 3 or more residues of EKTKEQ (SEQ ID NO: 1), optionally 4 or more residues, 5 or more residues or 6 residues, or can be specifically EKT, KTK, TKE, KEQ, EKTK (SEQ ID NO: 2), KTKE (SEQ ID NO: 3), TKEQ (SEQ ID NO: 4), EKTKE (SEQ ID NO: 8) or KTKEQ (SEQ ID NO: 9).

In an embodiment, the antibody comprises a heavy chain variable region and/or a light chain variable region, the heavy chain variable region comprising complementarity determining regions CDR-H1, CDR-H2 and CDR-H3, and the light chain variable region comprising complementarity determining regions CDR-L1, CDR-L2 and CDR-L3, with the amino acid sequence of one or more of said CDRs being selected from the amino acid sequences set forth below:
 CDR-H1: SEQ ID NOs: 61, 67, 73, 79, 91 or 180;
 CDR-H2: SEQ ID NOs: 62, 68, 74, 80, 92 or 181;
 CDR-H3: SEQ ID NOs: 63, 69, 75, 81, 93 or 182;
 CDR-L1: SEQ ID NOs: 64, 70, 76, 94 or 183;
 CDR-L2: SEQ ID NOs: 65, 71 or 77; or
 CDR-L3: SEQ ID NOs: 66, 72, 78, 84, 96 or 184.

In an embodiment, the CDRs are: In an embodiment, the CDRs are:
 CDR-H1: SEQ ID NO: 67; CDR-H2 SEQ ID NO: 68; CDR-H3: SEQ ID NO: 69;
 CDR-L1: SEQ ID NO: 70; CDR-L2: SEQ ID NO: 71; and CDR-L3: SEQ ID NO: 72.
In an embodiment, the CDRs are:
 CDR-H1: SEQ ID NO: 73; CDR-H2 SEQ ID NO: 74; CDR-H3: SEQ ID NO: 75;
 CDR-L1: SEQ ID NO: 76; CDR-L2: SEQ ID NO: 77; and CDR-L3: SEQ ID NO: 78.
In an embodiment, the CDRs are:
 CDR-H1: SEQ ID NO: 79; CDR-H2: SEQ ID NO: 80; CDR-H3: SEQ ID NO: 81;
 CDR-L1: SEQ ID NO: 76; CDR-L2: SEQ ID NO: 77; and CDR-L3: SEQ ID NO: 84.
In an embodiment, the CDRs are:
 CDR-H1: SEQ ID NO: 79; CDR-H2: SEQ ID NO: 80; CDR-H3: SEQ ID NO: 81;
 CDR-L1: SEQ ID NO: 76; CDR-L2: SEQ ID NO: 77; and CDR-L3: SEQ ID NO: 84.
In an embodiment, the CDRs are:
 CDR-H1: SEQ ID NO: 91; CDR-H2: SEQ ID NO: 92; CDR-H3: SEQ ID NO: 93;
 CDR-L1: SEQ ID NO: 94; CDR-L2: SEQ ID NO: 71; and CDR-L3: SEQ ID NO: 96.
In an embodiment, the CDRs are:
 CDR-H1: SEQ ID NO: 180; CDR-H2: SEQ ID NO: 181; CDR-H3: SEQ ID NO: 182;
 CDR-L1: SEQ ID NO: 183; CDR-L2: SEQ ID NO: 77; and CDR-L3: SEQ ID NO: 184.

A further aspect includes a nucleic acid described herein.

A further aspect is a vector comprising a nucleic acid described herein.

Another aspect includes a recombinant cell producing an antibody, nucleic acid or vector described herein. A further aspect includes a composition comprising a component (e.g. cyclic compound, antibody, nucleic acid, vector, recombinant cell etc and combinations thereof) described herein.

Another aspect provides an assay for detecting whether a test sample comprises misfolded oligomeric α-Syn comprising
 a. contacting the test sample with an antibody or immunoconjugate described herein under conditions permissive to produce an antibody:misfolded oligomeric α-Syn polypeptide complex; and
 b. detecting the presence or absence of any complex;
wherein the presence of detectable complex is indicative that the test sample may contain misfolded oligomeric α-Syn polypeptide.

The misfolded oligomeric α-Syn detected for example comprises a conformational epitope described herein selectively accessible in the misfolded oligomeric α-Syn polypeptide compared a native α-Syn, for example the epitope can selectively presented or accessible in misfolded oligomeric α-Syn.

A further aspect includes a method of inhibiting misfolded α-synuclein toxicity comprising administering to a cell population or a subject in need thereof an effective amount of an antibody, immunoconjugate or composition described herein.

Yet another aspect is a method of treating an α-synucleinopathy comprising administering an antibody, immunoconjugate or composition or combination of any of the foregoing described herein to a subject in need thereof. These antibodies for example as demonstrated herein, selectively bind to misfolded oligomeric α-synuclein and/or soluble α-synuclein fibrils (e.g. toxic misfolded species) compared to monomeric, tetrameric (e.g. physiological or native species) and/or insoluble fibril α-synuclein species.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

Various embodiments of the present disclosure will now be described in relation to the drawings in which:

FIG. 1A shows the predicted likelihood of exposure as a function of sequence, based on solvent accessible surface area (SASA). The graph of FIG. 1A represents the epitope predictions arising from stressed fibril structure PDB 2N0A, using the increase in SASA (ΔSASA) as a criterion to choose epitopes. The EKTK (SEQ ID NO: 2) (residues 57-60) and TKEQ (SEQ ID NO: 4) (residues 59-62) epitopes emerge as a prediction for PDB structure 2N0A (FIG. 1A). FIG. 1B shows the epitope predictions arising from structure PDB 2N0A, using the loss of native contacts as a criterion for epitope choice. The EKTK epitope (SEQ ID NO: 2) emerges as a prediction using this metric. FIG. 1C shows epitope predictions made by several metrics, including increased SASA (ΔSASA), increased root mean squared fluctuations (RMSF) of the atomic positions, which represents the increased dynamics of the epitope, and the decrease in the number of native contacts, Δcontacts. These 3 different metrics predict epitopes EKTK (SEQ ID NO: 2), KTKE (SEQ ID NO: 3), TKEQ (SEQ ID NO: 4), and their subsequences. That is, for one or more chains in the fibril structure, EKTK (SEQ ID NO: 2), KTKE (SEQ ID NO: 3), and TKEQ (SEQ ID NO: 4) satisfy all three of the above criteria, while neighboring regions do not satisfy this requirement.

FIG. 2A shows a rendering of a conformation of a monomer of α-Syn in the context of the unbiased fibril (PDB 2N0A). This structure is taken from an equilibrium simulation of 5 chains of α-Syn with 100 mM NaCl. Residues K58 and K60 are approximately parallel in this structural ensemble. There is a close contact between the Hε3 atom of K60 (which is weakly positive charged, Q=0.05) and the Nε2 of Q62 (which is negatively charged, Q=−0.64).

FIG. 2B shows a snapshot of the structure of a monomer of α-Syn in the biased fibril ensemble. Residues K58 and K60 are no longer parallel in this ensemble, and the contact between K60 and Q62 is no longer present. This suggests that K60 and Q62 may be more accessible for binding in the biased or "stressed" fibrils and oligomeric species of α-Syn compared to the unbiased fibril.

FIGS. 6A-H are a series of graphs. FIG. 6A is a series of graphs that show binding of antibodies to alpha-synuclein monomer by SPR. Strong binding is seen with pan antibody 4D6, and low level of binding is seen with Syn-F1 which favours aggregated alpha-synuclein and no binding is seen with test antibodies. FIG. 6B is a series of graphs that show binding of antibodies to alpha synuclein oligomer by SPR. FIG. 6C is a series of graphs that show binding of antibodies to alpha synuclein oligomer by sandwich SPR. FIG. 6D is a series of graphs that show binding to alpha-synuclein oligomers. FIG. 6E is a series of graphs showing antibody binding response to soluble LBD brain extract. FIG. 6F is a series of graphs showing antibody binding in HMW and LMW soluble LBD brain fractions. The first darker bar for each condition is HMW (~140-700 kDa) and the second lighter bar is LMW (~8-70 kDa). FIG. 6G is a graph that shows the degree of cross-reactive binding of the antibodies with small soluble fibrils. FIG. 6H is a graph that shows a comparison in the binding profile of a test antibody of the disclosure and pan antibody 4D6.

FIG. 7A-F are a series of dot blots.

FIG. 7G is a graph plotting the fold reactivity in dementia with Lewy Bodies (DLB) brain over normal brain.

FIGS. 8A to H are graphs and images showing alpha-syn toxicity inhibited by various test antibodies.

FIG. 9A is a graph showing antibody selective binding to synthetic alpha-syn oligomers but not to monomers or physiological tetramers by SPR. FIG. 9B is a graph that shows antibody selective binding to alpha-syn oligomers and sonicated fibrils.

FIG. 12A is a graph that shows test antibody binding to DLB soluble brain extract. FIG. 12B is a graph showing that test antibody binding to soluble DLB extract is epitope-specific.

FIGS. 13A to I are graphs and images showing that test antibodies reduce PFF induced formation of alpha-synuclein aggregates.

FIG. 14A to H are graphs and images showing that test antibodies reduce PFF induced aggregation and phosphorylation of endogenous alpha-synuclein.

FIG. 15A-B are graphs where FIG. 15A is a graph showing that test antibodies inhibit in-vitro propagation of alpha-synuclein aggregation and FIG. 15B is a graph showing that the cyclic peptide comprising an alpha-syn peptide comprising a conformational epitope is sufficient to replicate the seeding activity of pre-formed fibrils and is neutralized by test antibody 2E9.

FIGS. 16A and B are bar graphs showing binding response of test antibodies to brain extract from a multiple system atrophy (MSA) patient.

FIG. 16C is a bar graph showing binding response of test antibodies to a prion enriched fraction of brain extract.

FIGS. 17A to C are a series graphs illustrating the binding profile of test antibody 12G1.

FIGS. 18A-C are a series of graphs illustrating the binding profile of test antibody 9D8.

FIGS. 19A-C are a series of graphs depicting the binding profile of test antibody 10D5.

DETAILED DESCRIPTION OF THE DISCLOSURE

Figure 1A:
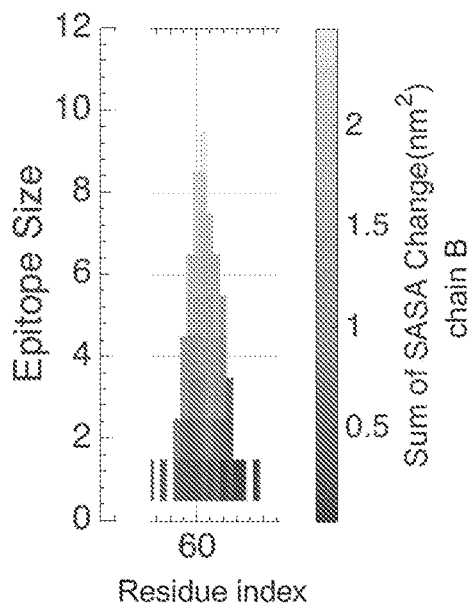
FIGS. 1A-C are graphs describing the predicted epitope.

Generation of conformation-specific antibodies was accomplished.

Antibodies raised to native protein regions tend not to be selective for misfolded protein such as non-native oligomeric species, and thus may bind to native functional protein as well as misfolded protein.

As described herein, to develop antibodies that may be selective for misfolded oligomeric forms of α-Syn, the inventors sought to identify regions of α-Syn sequence that are prone to disruption in the context of the fibril, and that may thus be exposed on the surface of the misfolded protein oligomers that could act as catalytic substrates for misfolding.

As described in the Examples, computational simulations, using molecular dynamics with standardized force-fields, were employed. An experimentally-validated structural model of the fibril structure was globally biased away from its reported conformation to be partially unfolded, using molecular dynamics, to yield regions of contiguous primary sequence that are prone to be disordered upon an external challenge in an anomalous cellular environment.

It was hypothesized that these weakly-stable regions may be selectively exposed in misfolded pathogenic species such as non-native oligomers.

As described the Examples, the inventors have identified conformational epitopes. The inventors designed cyclic compounds comprising the identified epitopes to mimic the putative selective epitope by satisfying several criteria such as a higher exposed surface area, loss of contact interactions present in the fibril, and/or conformations that did not readily align by root mean squared deviation (RMSD) to the isolated monomeric ensemble, but would align more favorably to a biased, partially disordered fibril ensemble. As further shown in the Examples, monoclonal antibodies produced using immunogens comprising these cyclic compounds produced antibodies that preferentially bound misfolded oligomeric alpha-synuclein and inhibited alpha-synuclien induced neural toxicity.

I. Definitions

As used herein, the term "α-Syn" alternately referred to as "α-synuclein", or "Alpha-Synuclein", or "alpha-syn" as used herein means all forms of α-Syn including wildtype sequence α-Syn and mutated forms, monomeric α-Syn, and aggregates thereof such as misfolded oligomers and soluble fibrillar forms of α-Syn, from all species, particularly human α-Syn (i.e. huα-Syn). Human α-Syn is a protein of typically 140 amino acid residues and the amino acid sequence (e.g. Uniprot Accession number P37840) and the nucleotide sequence (e.g. Accession number HGNC: 11138) have been previously characterized.

"Wild type" as used herein refers to the primary amino acid sequence of non-mutant or naturally occurring protein in humans.

"Native alpha-synuclein polypeptide" or "a native α-Syn" as used herein refers to the alpha-synuclein monomer whether associated with membrane or cytosolic as well as other multimers found in normal cells, such as tetramer, and for example as can be predicted when using one of the chains from the PDB fibril (2N0A) as described herein. Native alpha-synuclein polypeptide can be detected using pan antibodies in for example brains not afflicted by a synucleinopathy.

Models of the native α-Syn tetramer [pnas.orq/cqi/doi/10.1073/pnas.1113260108] show that it is stabilized by interactions that include residues in the above epitopes, specifically, inter-chain salt-bridges between K60-E57 and between K34-E57. As well, Q62 exhibited among the largest paramagnetic relaxation effects indicating that it is strongly interacting in the tetramer vs. the isolated monomer. These interactions may result in the sequestration of the epitope in the naturally occurring native tetrameric form, so that antibodies targeting the epitope would select for non-native species (e.g. misfolded oligomeric alpha-synuclein).

"Structured fibril", "un-stressed fibril", or "unbiased fibril" as used herein refers to the expected conformations that would be observed in thermal equilibrium for a fibril of alpha-synuclein, e.g. for which PDB 2N0A would be a representative example of.

"Misfolded oligomer", "non-native oligomer" as used herein refers to the secondary and tertiary structure of a multisubunit polypeptide or polypeptide aggregation, and indicates that the oligomeric polypeptide, or a subunit therein has adopted a conformation (e.g. at one or more locations) that is different from that typically adopted by the native monomer and/or tetramer. Although misfolding can be caused by mutations in a protein, such as amino acid deletion, substitution, or addition, wild-type sequence protein can also be misfolded in disease, and expose disease-specific or selective epitopes for instance, as a result of a change in microenvironmental conditions, or oligomer formation that may be on- or off-pathway to fibril formation (e.g. insoluble fibrils). Accordingly, "misfolded oligomeric α-Syn polypeptide", "misfolded alpha-Syn" or "misfolded oligomeric α-Syn" when referring to the polypeptide herein refers to α-Syn polypeptide oligomers that displays a conformation that is different from nascently folded monomeric α-Syn and/or natively folded tetrameric alpha-synuclein and includes for example non-native oligomers, soluble fibrils, protofibrils, and fibril fragments. Soluble fibrils include for example α-syn fibril species that are found in the supernatant of a sample subjected to ultracentrifugation at 100,000×g for 1 hour. Soluble fibrils can be produced by sonicating fibrils which produces fragments. For example, misfolded oligomeric α-Syn can include a conformation that is partially-ordered, containing parts of the fibril structure, and partially-disordered, containing polymer segments of amino acids that have alternate conformations than either monomer, tetramer and/or fibril α-Syn. Misfolded oligomeric alpha-synuclein as shown herein includes conformational epitopes that are selectively presented or accessible for binding wherein the epitope sequence in misfolded oligomeric alpha-synuclein can be conformationally different than the corresponding sequence in the context of the isolated monomer, as measured for example by side chain orientation or by root mean-squared deviation (RMSD). Misfolded alpha-synuclein may comprise at least one of the residues E57, K58, T59, K60, E61, or Q62 in an alternate conformation than occupied by E57, K58, T59, K60, E61, and/or Q62 in a non-misfolded proteinic conformation such as native monomer and/or tetramer or in insoluble fibrils such as those found in Lewy body deposits. Soluble α-synuclein fibrils refers to smaller fibrils or fragments for example fibrils that are sonicated as described in the Examples and which are in solution as well as disease associated smaller fibrils that are not present in Lewy bodies which comprise insoluble fibrils.

The term "mutant α-Syn" refers to forms of α-Syn, and particularly endogenous forms of α-Syn that occur as a result of genetic mutation that result for instance in amino acid substitution, such as those substitutions characteristic for instance of familial Parkinson's disease.

The term "EKTK (SEQ ID NO: 2)" means the amino acid sequence: glutamic acid, lysine, threonine, lysine, as shown in SEQ ID NO: 2. The term "TKEQ (SEQ ID NO: 4)" means the amino acid sequence: threonine, lysine, glutamic acid, glutamine, as shown in SEQ ID NO: 4. Similarly EKT, KTK, TKE, KEQ, EKTKEQ (SEQ ID NO: 1), EKTKE (SEQ ID NO: 8), KTKE (SEQ ID NO: 3), KTKEQ (SEQ ID NO: 9) refer to the amino acid sequences identified by the 1-letter amino acid code. Depending on the context, the reference of the amino acid sequence can refer to a sequence in α-Syn or an isolated peptide, such as the amino acid sequence of the epitope portion of a cyclic compound. The sequences EKTK (SEQ ID NO: 2) and TKEQ (SEQ ID NO: 4) consist of residues 57-60 and residues 59-62 in the α-Syn amino acid primary sequence, respectively (e.g. Uniprot Accession number P37840).

The term "epitope in EKTKEQ (SEQ ID NO: 1)" as used herein refers to any part thereof that is specifically bound by an antibody. For example the antibody may specifically bind the side chains and/or backbones of a combination of several residues in the epitope, including several of E57, and/or E61, and/or K58, and/or K60, and/or Q62, and/or T59, or a particular part of these residues, or a combination of any of the foregoing. The epitope can be a conformational epitope.

The term "epitope" as used herein means a sequence of amino acids in an antigen wherein the amino acids (or a subset thereof) in the sequence are specifically recognized by an antibody or binding fragment, for example an antibody or binding fragment described herein. An epitope can comprise one or more antigenic determinants. For example, an antibody generated against an isolated peptide corresponding to a conformational epitope recognizes part or all of said epitope sequence.

The term "epitope selectively presented or accessible in misfolded oligomeric α-Syn" as used herein refers to a conformational epitope that is selectively presented or accessible on misfolded oligomeric α-Syn polypeptide as present in synucleinopathies such as Parkinson's disease and Lewy Body Dementia (e.g. disease-associated misfolded α-Syn) whether in multimeric, oligomeric, or aggregated forms, but not on the molecular surface of the nascent monomeric peptide or tetrameric forms of α-Syn as found normally in vivo.

As used herein, the term "conformational epitope" refers to a sequence of amino acids or an antigenic determinant thereof that has a particular three-dimensional structure in a species of a protein wherein at least an aspect of the three-dimensional structure is present or is more accessible to antibody binding compared to in another species such as an isolated monomer (native) or other native structure. Antibodies which specifically bind a conformational epitope recognize the spatial arrangement of one or more of the amino acids of that conformation-specific epitope. For example, a conformational epitope in EKTKEQ (SEQ ID NO: 1) can refer to a conformation of one or more amino acids or parts thereof of EKTKEQ (SEQ ID NO: 1) that is recognized by antibodies selectively, for example at least 2 fold, 3 fold, 5 fold, 10 fold, 50 fold, 100 fold, 250 fold, 500 fold or 1000 fold or greater more selectivity as compared to another conformation, optionally the corresponding region in the α-Syn monomer or insoluble fibril or for example antibodies raised using a corresponding linear peptide or part thereof.

Reference to the "cyclic peptide" herein can refer to a fully proteinaceous cyclic compound (e.g. wherein the linker is 2, 3, 4, 5, 6, 7 or 8 amino acids). It is understood that properties described for the cyclic peptide determined in the examples can be incorporated in other compounds (e.g. cyclic compounds) comprising non-amino acid linker molecules.

The term "amino acid" includes all of the naturally occurring amino acids as well as modified L-amino acids. The atoms of the amino acid can for example include different isotopes. For example, the amino acids can comprise deuterium substituted for hydrogen, nitrogen-15 substituted for nitrogen-14, and carbon-13 substituted for carbon-12 and other similar changes.

The term "antibody" as used herein is intended to include monoclonal antibodies, polyclonal antibodies, single chain, single domain, humanized and other chimeric antibodies as well as binding fragments thereof. The antibody may be from recombinant sources and/or produced in transgenic animals. The antibody in an embodiment comprises a heavy chain variable region or a heavy chain comprising a heavy chain complementarity determining region 1, heavy chain complementarity determining region 2 and heavy chain complementarity determining region 3, as well as a light chain variable region or light chain comprising a light chain complementarity determining region 1, light chain complementarity determining region 2 and light chain complementarity determining region 3. Also included are human antibodies that can be produced through using biochemical techniques or isolated from a library. Humanized or chimeric antibody may include sequences from one or more than one isotype or class. Reference to antibody or antibodies of the disclosure refers to antibody or antibodies described herein that are for example raised using an immunogen described herein and/or selective for an epitope described herein for example KTKE (SEQ ID NO: 3), EKTK (SEQ ID NO: 2) or TKEQ (SEQ ID NO: 4) or a part thereof in the context for example of the epitope, misfolded oligomeric alpha-synuclein and/or a cyclic compound comprising one of said epitope sequences.

The term "heavy chain complementarity determining region" as used herein refers to regions of hypervariability within the heavy chain variable region of an antibody molecule. The heavy chain variable region has three complementarity determining regions termed heavy chain complementarity determining region 1 (CDR-H1), heavy chain complementarity determining region 2 (CDR-H2) and heavy chain complementarity determining region 3 (CDR-H3) from the amino terminus to carboxy terminus.

The term "heavy chain variable region" as used herein refers to the variable domain of the heavy chain comprising the heavy chain complementarity determining region 1, heavy chain complementarity determining region 2 and heavy chain complementarity determining region 3. One or more amino acids or nucleotides can be modified for example replaced with a conservative substitution, for example outside the CDR sequences. The variable region comprises framework region 1 (FR1), followed by CDR1, followed by framework region 2 (FR2), followed by CDR2, followed by framework region 3 (FR3), followed by CDR3, followed by framework region 4 (FR4).

The term "light chain complementarity determining region" as used herein refers to regions of hypervariability within the light chain variable region of an antibody molecule. Light chain variable regions have three complementarity determining regions termed light chain complementarity determining region 1, light chain complementarity determining region 2 and light chain complementarity determining region 3 from the amino terminus to the carboxy terminus.

The term "light chain variable region" as used herein refers to the variable domain of the light chain comprising the light chain complementarity determining region 1, light chain complementarity determining region 2 and light chain complementarity determining region 3. The variable region comprises framework region 1 (FR1), followed by CDR1, followed by framework region 2 (FR2), followed by CDR2, followed by framework region 3 (FR3), followed by CDR3, followed by framework region 4 (FR4).

The phrase "isolated antibody" refers to antibody produced in vivo or in vitro that has been removed from the source that produced the antibody, for example, an animal, hybridoma or other cell line (such as recombinant cells that produce antibody). The isolated antibody is optionally "purified", which means at least: 80%, 85%, 90%, 95%, 98% or 99% purity.

The term "binding fragment" as used herein to a part or portion of an antibody or antibody chain comprising fewer amino acid residues than an intact or complete antibody or antibody chain and which binds the antigen or competes with intact antibody. Exemplary binding fragments include without limitations Fab, Fab', F(ab')2, scFv, dsFv, ds-scFv, nanobodies, minibodies, diabodies, and multimers thereof. Fragments can be obtained via chemical or enzymatic treatment of an intact or complete antibody or antibody chain. Fragments can also be obtained by recombinant means. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be constructed by recombinant expression techniques.

When an antibody is said to bind to an epitope in, such as EKTKEQ (SEQ ID NO: 1), or TKEQ (SEQ ID NO: 4), what is meant is that the antibody specifically binds to a polypeptide or compound containing the specified residues or a part thereof for example at least 1 residue or at least 2 residues. Such an antibody does not necessarily contact every residue of EKTK (SEQ ID NO: 2) or TKEQ (SEQ ID NO: 4), and every single amino acid substitution or deletion within said epitope does not necessarily significantly affect or equally affect binding affinity.

The term "detectable label" as used herein refers to moieties such as peptide sequences, fluorescent proteins that can be appended or introduced into a peptide or compound described herein and which is capable of producing, either directly or indirectly, a detectable signal. For example, the label may be radio-opaque, positron-emitting radionuclide (for example for use in PET imaging), or a radioisotope, such as $^{3}$H, $^{13}$N, $^{14}$C, $^{18}$F, $^{32}$F, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion. The detectable label may be also detectable indirectly for example using secondary antibody.

The term "greater affinity" as used herein refers to a degree of antibody binding where an antibody X binds to target Y more strongly ($K_{on}$) and/or with a smaller dissociation constant ($K_{off}$) than to target Z, and in this context antibody X has a greater affinity for target Y than for Z. Likewise, the term "lesser affinity" herein refers to a degree of antibody binding where an antibody X binds to target Y less strongly and/or with a larger dissociation constant than to target Z, and in this context antibody X has a lesser affinity for target Y than for Z. The affinity of binding between an antibody and its target antigen, can be expressed as $K_A$ equal to $1/K_D$ where $K_D$ is equal to $k_{on}/k_{off}$. The $k_{on}$ and $k_{off}$ values can be measured using surface plasmon resonance (measurable for example using a Biacore system).

Also as used herein, the term "immunogenic" refers to substances which elicit the production of antibodies, activate lymphocytes and other reactive immune cells directed against an antigenic portion of the immunogen.

An "immunogen" as used herein means a substance which provokes an immune response and/or causes production of an antibody and can comprise for example cyclic peptides described herein, conjugated as multiantigenic peptide and/or fused to an immunogenicity enhancing agent such as Keyhole Limpet Hemocyanin (KLH). In addition to the conjugates described herein, immunogenic peptide mimetics which elicit cross-reactive antibodies to the epitopes identified, e.g. EKTKEQ (SEQ ID NO: 1), EKTK (SEQ ID NO: 2), TKEQ (SEQ ID NO: 4) or KTKE (SEQ ID NO: 3). To serve as a useful immunogen, the α-Syn peptide desirably incorporates a minimum of about 3, 4, 5, 6, or 7 α-Syn residues, comprising E57, K58, T59, K60, E61, and/or Q62.

The term "inhibiting" as used herein for example in the context of an antibody of the disclosure inhibiting alpha-syn phosphorylation means reducing the amount of alpha-syn phosphorylation in the presence of the antibody by at least 10%, at least 20%, at least 30% compared to in the absence of the antibody.

The term "corresponding linear compound" with regard to a cyclic compound refers to a compound, optionally a peptide, comprising or consisting of the same sequence or chemical moieties as the cyclic compound but in linear (non-cyclized) form.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid can be either double stranded or single stranded, and represents the sense or antisense strand. Further, the term "nucleic acid" includes the complementary nucleic acid sequences as well as codon optimized or synonymous codon equivalents. The term "isolated nucleic acid sequences" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived.

The term "vector" as used herein comprises any intermediary vehicle for a nucleic acid molecule which enables said nucleic acid molecule, for example, to be introduced into prokaryotic and/or eukaryotic cells and/or integrated into a genome, and include plasmids, phagemids, bacteriophages or viral vectors such as retroviral based vectors, Adeno Associated viral vectors and the like. The term "plasmid" as used herein generally refers to a construct of extrachromosomal genetic material, usually a circular DNA duplex, which can replicate independently of chromosomal DNA.

The term "host cell" refers to a cell into which a recombinant DNA expression vector can be introduced to produce a recombinant cell. The host cell can be a bacterial cell such as *E. coli* as well as any type of microbial, yeast, fungi, insect or mammalian host cell. Mammalian host cell can be a human cell.

The term "pharmaceutically acceptable" means that the carrier, diluent, or excipient is compatible with the other components of the formulation and not substantially deleterious to the recipient thereof.

The term "administered" as used herein means administration of a therapeutically effective dose of a compound or composition of the disclosure to a cell or subject.

As used herein, the phrase "effective amount" means an amount effective, at dosages and for periods of time necessary to achieve a desired result. Effective amounts when administered to a subject may vary according to factors such as the disease state, age, sex, weight of the subject. Dosage regime may be adjusted to provide the optimum therapeutic response.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. For example, a subject with early stage PD can be treated to prevent progression. Such a subject can be treated with a compound, antibody, immunogen, immunoconjugate or composition described herein to prevent progression.

As used herein "specifically binds" in reference to an antibody means that the antibody binds to its target antigen with greater affinity than it does to a structurally or conformationally different antigen and/or to an antigen with modified or mutated sequence. For example a multivalent antibody binds its target with $K_D$ of at least 5e-5, at least 1e-6, at least 1e-7, at least 1e-8, or at least 1e-9. Affinities greater than at least 1e-7 are preferred. An antigen binding fragment such as Fab fragment comprising one variable domain, may bind its target with for example a 10 fold or 100 fold less affinity/avidity than a multivalent interaction with a non-fragmented antibody.

The term "selective" or "selectively binds" as used herein with respect to an antibody that preferentially binds a form of α-Syn (e.g. misfolded conformations such as misfolded oligomers and small soluble fibrils relative to isolated native monomer or native tetramers and/or insoluble fibrillar alpha-synuclein) means that the binding protein binds the form with at least 2 fold, 3 fold, or at least 5 fold, at least 10 fold, at least 100 fold, at least 250 fold, at least 500 fold or at least 1000 fold or more greater affinity. Accordingly an antibody that is more selective for a particular conformation (e.g. misfolded oligomers) preferentially binds the particular form of α-Syn with at least 3 fold etc. greater affinity compared to another form.

The term "linker" as used herein means a chemical moiety, preferably poorly immunogenic or non-immunogenic, that can be covalently linked directly or indirectly to the α-Syn peptide N- and/or C-termini comprising at least 3 amino acids of EKTKEQ (SEQ ID NO: 1), optionally EKTK (SEQ ID NO: 2), KTKE (SEQ ID NO: 3) or TKEQ (SEQ ID NO: 4) epitope peptide, which is linked to the peptide N- and/or C-termini. The linker ends can for example be joined to produce a cyclic compound. The linker can comprise one or more functionalizable moieties such as one or more cysteine residues. The linker can be linked via the functionalizable moieties to a carrier protein or an immunogen enhancing agent such as keyhole limpet hemocyanin (KLH). The cyclic compound comprising the linker is of longer length than the peptide itself. That is, when cyclized the peptide with a linker (for example of 3 amino acid residues)

makes a larger closed circle than the peptide without a linker. The linker may include, but is not limited to, non-immunogenic moieties such as amino acids G and A, or PEG repeats.

The term "functionalizable moiety" as used herein refers to a chemical entity with a "functional group" which as used herein refers to a group of atoms or a single atom that will react with another group of atoms or a single atom (so called "complementary functional group") to form a chemical interaction between the two groups or atoms. In the case of cysteine, the functional group can be —SH which can be reacted to form a disulfide bond. Accordingly the linker can for example be CCC. The reaction with another group of atoms can be covalent or a strong non-covalent bond, for example as in the case as biotin-streptavidin bonds, which can have Kd~1e-14. A strong non-covalent bond as used herein means an interaction with a Kd of at least 1e-9, at least 1e-10, at least 1e-11, at least 1e-12, at least 1e-13 or at least 1e-14.

Proteins and/or other agents may be coupled to the cyclic compound, either to aid in immunogenicity, or to act as a probe in in vitro studies. For this purpose, any functionalizable moiety capable of reacting (e.g. making a covalent or non-covalent but strong bond) may be used. In one specific embodiment, the functionalizable moiety is a cysteine residue which is reacted to form a disulfide bond with an unpaired cysteine on a protein of interest, which can be, for example, an immunogenicity enhancing agent such as Keyhole limpet hemocyanin (KLH), or a carrier protein such as Bovine serum albumin (BSA) used for in vitro immunoblots or immunohistochemical assays.

The term "animal" or "subject" as used herein includes all members of the animal kingdom including mammals, including humans.

Compositions or methods "comprising" or "including" one or more recited elements may include other elements not specifically recited. For example, a composition that "comprises" or "includes" an antibody may contain the antibody alone or in combination with other ingredients.

In understanding the scope of the present disclosure, the term "consisting" and its derivatives, as used herein, are intended to be close ended terms that specify the presence of stated features, elements, components, groups, integers, and/or steps, and also exclude the presence of other unstated features, elements, components, groups, integers and/or steps.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about." Further, it is to be understood that "a," "an," and "the" include plural referents unless the content clearly dictates otherwise. The term "about" means plus or minus 0.1 to 50%, 5-50%, or 10-40%, preferably 10-20%, more preferably 10% or 15%, of the number to which reference is being made.

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The singular forms of the articles "a," "an," and "the" include plural references unless the context clearly dictates otherwise. For example, the term "a compound" or "at least one compound" can include a plurality of compounds, including mixtures thereof.

II. Epitopes and Epitope Compounds

The inventors have identified sequences in α-Syn protein including EKTK (SEQ ID NO: 2), KTKE (SEQ ID NO: 3) and TKEQ (SEQ ID NO: 4) at amino acids 57-60, 58-61 and 59-62 respectively that may be conformational epitopes, such that for example that EKTK (SEQ ID NO: 2) and TKEQ (SEQ ID NO: 4) or a part of each of thereof may be selectively accessible to antibody binding in misfolded oligomeric species of α-Syn.

Based on one or more conformational differences identified between the epitopes identified in monomeric, fibril and/or biased α-Syn fibril ensembles, the inventors have designed conformationally restricted compounds and immunogens for producing antibodies.

As shown in the Examples antibodies raised using said immunogens are useful for detecting or targeting misfolded oligomeric α-Syn.

As described in the Examples, cyclic compounds such as cyclic peptides cyclo(CGGGGEKTKGG) (SEQ ID NO: 5), cyclo(CGTKEQGGGG) (SEQ ID NO: 7), cyclo (CGGGEKTKGG) (SEQ ID NO: 10) and cyclo (CGGGGTKEQGG) (SEQ ID NO: 11) were identified to capture the conformational differences of the corresponding epitope in misfolded oligomeric species of α-Syn relative to monomeric and/or insoluble fibril species. For example, RMSD structural alignment for amino acids in the cyclic 10-mer cyclo(CGTKEQGGGG) (SEQ ID NO: 7) were found to be significantly different than the corresponding quantities in the monomeric ensemble. This suggests that the cyclic compound may provide for a conformational epitope that is conformationally-distinct from the sequence presented in the nascent monomeric α-Syn and/or insoluble fibril.

Accordingly, the present disclosure identifies conformational epitopes in α-Syn for example peptides EKTK (SEQ ID NO: 2), and KTKE (SEQ ID NO: 3) and TKEQ (SEQ ID NO: 4) or a part thereof such as EK corresponding to amino acids residues 57-58 on α-Syn and KEQ corresponding to amino acids 60-62 on α-Syn. As demonstrated in the Examples, EKTK (SEQ ID NO: 2) and TKEQ (SEQ ID NO: 4) were identified as regions prone to disorder in α-Syn. The residues EKTK (SEQ ID NO: 2) and TKEQ (SEQ ID NO: 4) emerged in a prediction using the Collective Coordinates method as described in the Examples.

An aspect includes a compound comprising an α-Syn peptide comprising at least 3 amino acids of EKTKEQ (SEQ ID NO: 1), optionally EKTK (SEQ ID NO: 2), KTKE (SEQ ID NO: 3) or TKEQ (SEQ ID NO: 4), and/or part of any of the foregoing such as KEQ. In an embodiment, the α-Syn peptide is selected from EKTK (SEQ ID NO: 2), KTKE (SEQ ID NO: 3), TKEQ (SEQ ID NO: 4), EKTKE (SEQ ID NO: 8), EKT, KTK, TKE, KEQ, or KTKEQ (SEQ ID NO: 9).

The α-Syn peptide can also include an additional 1, 2 or 3 amino acids in α-Syn either N-terminal and/or C-terminal to EKTKEQ (SEQ ID NO: 1) (or an internal sequence thereof such as EKT or EKTK (SEQ ID NO: 2)) for 1, 2 or 3 N-terminal amino acid residues, and/or) with 1, 2 or 3 C-terminal amino acid residues. In some embodiments, the maximum length of the α-Syn peptide is 9 amino acids, 8 amino acids or 7 amino acids.

In an embodiment, the α-Syn peptide comprises or consists of KEQ, TKEQ (SEQ ID NO: 4), KTKEQ (SEQ ID NO: 9) or EKTKEQ (SEQ ID NO: 1).

In an embodiment, the compound further comprises a linker. The linker can comprise one or more functionalizable moieties. The linker can for example comprise 1, 2, 3, 4, 5, 6, 7 or 8 amino acids and/or equivalently functioning molecules such as polyethylene glycol (PEG) moieties, and/or a combination thereof. In an embodiment, the linker amino acids are selected from non-immunogenic or poorly immunogenic amino acid residues such as G and A, for example the linker can be GG, GGG, GAG, G(PEG)G, PEG-PEG(also referred to as PEG2)-GG and the like. One or more functionalizable moieties e.g. amino acids with a functional group may be included for example for coupling the compound to an agent or detectable tag or a carrier such as BSA or an immunogenicity enhancing agent such as KLH. The functionalizable moiety can be an amino acid such as cysteine. In an embodiment, the linker comprises up to or a maximum of 1, 2, 3, 4, 5, 6, 7 or 8 amino acids.

In an embodiment, the linker comprises GC-PEG, PEG-GC, GCG or PEG2-CG. In another embodiment, the linker comprises GCGGGG (SEQ ID NO: 12), GGCGG (SEQ ID NO: 13), GGCGGGG (SEQ ID NO: 14), GGGCGG (SEQ ID NO: 15) or GGGGCGG (SEQ ID NO: 16). Other linkers are provided (presented in constructs comprising the alpha-Syn peptide) in Tables 2-4.

Proteinaceous portions of compounds (or the compound wherein the linker is also proteinaceous) may be prepared by chemical synthesis using techniques well known in the chemistry of proteins such as solid phase synthesis or synthesis in homogenous solution.

The compound can be linear and can be used for example for selecting antibodies that bind preferentially to the corresponding cyclic compound. Preferably, the compound is a conformational compound, such as a cyclic compound. As shown in the Examples this can be accomplished using a cyclic peptide comprising the α-Syn peptide.

An aspect therefore provides a cyclic compound comprising an α-Syn peptide comprising at least 3 amino acids of EKTKEQ (SEQ ID NO: 1), optionally EKTK (SEQ ID NO: 2), KTKE (SEQ ID NO: 3) or TKEQ (SEQ ID NO: 4), and/or part of any of the foregoing and a linker, wherein the linker is covalently coupled directly or indirectly to the α-Syn peptide. As shown in the Examples, residues in the cyclic peptide are in an alternate conformation compared to the corresponding residue in monomer or fibril ensembles. In an embodiment, the cyclic compound comprises an α-Syn peptide and linker described herein. In an embodiment, the cyclic compound comprises an α-Syn peptide comprising EKT, KEQ, EKTK (SEQ ID NO: 2), KTKE (SEQ ID NO: 3), or TKEQ (SEQ ID NO: 4) and up to 6 α-Syn residues (e.g. 1 or 2 amino acids N and/or C terminus to EKTK (SEQ ID NO: 2), KTKE (SEQ ID NO: 3), or TKEQ (SEQ ID NO: 4) and a linker, wherein the linker is covalently coupled directly or indirectly to the peptide N-terminus residue and the C-terminus residue of the α-Syn peptide. The exposure of the residues in the cyclic peptide can be different than corresponding residues, in the monomeric and/or fibril ensembles and cellular monomeric and insoluble fibrillar α-Syn. For example in the cyclic compound, at least one of E57, K58, T59, K60, E61, or Q62, has more surface exposure than the conformation occupied in the monomeric ensemble.

In embodiments wherein the peptide comprising EKTK (SEQ ID NO: 2), EKT, EKTKE (SEQ ID NO: 8), KTKEQ (SEQ ID NO: 9), KEQ or TKEQ (SEQ ID NO: 4) includes 1, 2 or 3 additional residues found in α-Syn that are N- and/or C-terminal to EKTK (SEQ ID NO: 2) or TKEQ (SEQ ID NO: 4) the linker in the cyclized compound is covalently linked to the N- and/or C-termini of the α-Syn additional residues. Similarly, where the α-Syn peptide is EKTK (SEQ ID NO: 2) the linker is covalently linked to residues E and K, where the α-Syn peptide is TKEQ (SEQ ID NO: 4), the linker is covalently linked to residues T and Q, and where the α-Syn peptide is KTKEQ (SEQ ID NO: 9), the linker is covalently linked to residues K and Q.

In an embodiment, the cyclic compound comprises a peptide comprising or consisting of EKTK (SEQ ID NO: 2), KTKE (SEQ ID NO: 3), or TKEQ (SEQ ID NO: 4) and a linker, wherein the linker is coupled to the N- and C-termini of the peptide.

In an embodiment, the alternate conformation is a more solvent-exposed conformation, for one or more of the residues E57, K58, T59, K60, E61, or Q62.

In one embodiment, the cyclic compound is a cyclic peptide. In another embodiment, the cyclic peptide comprises or consists of the sequence of any one of SEQ ID NOs: 5, 7 and 10-60. In one embodiment, the cyclic peptide comprises or consists of the sequence of CGGGGEKTKGG (SEQ ID NO: 5). In another embodiment, the cyclic peptide comprises or consists of the sequence of CGTKEQGGGG (SEQ ID NO: 7). In another embodiment, the cyclic peptide comprises or consists of the sequence of CGGGEKTKGG (SEQ ID NO: 10).

The cyclic peptides and corresponding linear peptides can for example be referenced by identifying the positions of the linker residues relative to the α-Syn peptide and the functionalizable moiety. For example, CGGGGEKTKGG (SEQ ID NO: 5) can be referred to as the 4, 2 construct, CGTKEQGGGG (SEQ ID NO: 7), can be referred to as the 1, 4 construct and CGGGEKTKGG can be referred to as the 3, 2 construct.

Methods for making cyclized peptides are known in the art and include SS-cyclization or amide cyclization (head-to-tail, or backbone cyclization). Methods are further described in the Example section. For example, a peptide with "C" residues at its N- and C-termini, e.g. CGGEKTKGGC (SEQ ID NO: 17), can be reacted by SS-cyclization to produce a cyclic peptide. The cyclic compound can be synthesized as a linear molecule with the linker covalently attached to the N-terminus or C-terminus of the peptide comprising the α-Syn peptide, optionally EKTK (SEQ ID NO: 2), KTKE (SEQ ID NO: 3), or TKEQ (SEQ ID NO: 4) or related epitope, prior to cyclization. Alternatively, part of the linker is covalently attached to the N-terminus and part is covalently attached to the C-terminus prior to cyclization. In either case, the linear compound is cyclized for example in a head to tail cyclization (e.g. amide bond cyclization).

As described in the Examples, cyclic compounds were assessed for their relatedness to the conformational epitopes identified, synthesized and used to prepare immunogens and used to raise antibodies selective for misfolded oligomeric α-Syn. The epitopes EKTK (SEQ ID NO: 2), KTKE (SEQ ID NO: 3), or TKEQ (SEQ ID NO: 4) and/or parts thereof, as described herein may be a potential target in misfolded propagating strains of α-Syn, and antibodies that recognize the conformational epitope as shown herein are useful for detecting misfolded species and inhibiting such propagating strains. As mentioned the above cyclic compounds comprising the α-Syn peptides can be used as an immunogen to raise antibodies.

Accordingly another aspect includes an immunogen comprising a conformational compound, optionally a cyclic compound, such as a cyclic peptide, described herein. In an embodiment, the immunogen comprises an immunogenicity enhancing agent such as Keyhole Limpet Hemocyanin (KLH) or carrier such as bovine serum albumin (BSA) or ovalbumin. The immunogenicity enhancing agent can be coupled to the compound either directly, such as through an amide bound, or indirectly through a chemical linker. Alternatively the immunogen may be a multi antigenic peptide (MAP).

The immunogen can be produced by conjugating the cyclic compound containing the constrained α-Syn epitope peptide to an immunogenicity enhancing agent such as KLH or a carrier such as BSA using for example the method described in Lateef et al 2007, herein incorporated by reference. In an embodiment, the method described in Examples 3 and 4 is used.

III. Antibodies

The compounds and particularly the cyclic compounds comprising any 3 amino acid residues of EKTKEQ (SEQ ID NO: 1) such as alpha-Syn peptide EKTK (SEQ ID NO: 2), KTKE (SEQ ID NO: 3), or TKEQ (SEQ ID NO: 4) described herein can be used to raise antibodies that selectively bind the compound comprising the alpha-Syn peptide relative to the corresponding linear compound, and/or also bind an epitope in the alpha-Syn peptide in misfolded forms of alpha-Syn including misfolded oligomeric alpha-Syn relative to monomeric and/or alpha-Syn insoluble fibrils. As shown in the Examples, the cyclic compounds exhibit one or more spatial conformations that are dissimilar to unbiased fibrillar alpha-Syn and which resemble partially unfolded fibrillar alpha-Syn (biased alpha-Syn). Further, it is demonstrated that antibodies raised using said compounds are selective for cyclic peptides and also bind misfolded alpha-syn such as misfolded oligomeric alpha-syn selectively relative to native species, indicating that they preferentially recognize a conformation of these residues in the misfolded α-Syn. For example, as shown in the examples, the antibodies raised preferentially bind misfolded oligomeric species relative to monomeric and insoluble fibril species.

Similarly, cyclic compounds comprising for example EKT, KTK, TKE, KEQ, EKTK (SEQ ID NO: 2), KTKE (SEQ ID NO: 3), TKEQ (SEQ ID NO: 4), EKTKE (SEQ ID NO: 8) or KTKEQ (SEQ ID NO: 9) and/or other related epitope sequences described herein can be used to raise antibodies that selectively bind for example to EKT, KTK, TKE, KEQ, EKTK (SEQ ID NO: 2), KTKE (SEQ ID NO: 3), TKEQ (SEQ ID NO: 4), EKTKE (SEQ ID NO: 8) or KTKEQ (SEQ ID NO: 9) etc. in the context of misfolded oligomeric alpha-Syn.

Accordingly, an aspect includes an antibody that binds an epitope in an α-Syn peptide, the α-Syn peptide comprising or consisting of EKTKEQ (SEQ ID NO: 1), or a related epitope thereof such as a part thereof comprising at least 3 or at least 4 amino acids. In an embodiment, α-Syn peptide selected from EKT, KTK, TKE, KEQ, EKTK (SEQ ID NO: 2), KTKE (SEQ ID NO: 3) and TKEQ (SEQ ID NO: 4).

In an embodiment, epitope is a conformational epitope.

The α-Syn peptide may be in a cyclic compound and/or in a misfolded α-Syn such as misfolded oligomeric α-Syn. In an embodiment, the antibody selectively binds a cyclic compound comprising the α-Syn peptide relative to a corresponding linear compound. In another embodiment, the antibody selectively binds α-Syn peptide in a misfolded α-Syn such as oligomeric α-Syn relative to monomeric or insoluble fibrillar α-Syn.

In an embodiment, the antibody is isolated.

In an embodiment, the antibody does not selectively bind isolated native monomeric alpha-Syn relative to misfolded forms such as misfolded oligomeric alpha-Syn. Binding including selective binding can be measured using, for example, an ELISA or surface plasmon resonance measurement, for example as described herein.

Accordingly a further aspect is an antibody which specifically or selectively binds a conformational epitope in an α-Syn peptide in a cyclic compound comprising said α-Syn peptide or in misfolded oligomeric α-Syn, wherein the α-Syn peptide or the epitope comprises or consists of EKTKEQ (SEQ ID NO: 1), EKTK (SEQ ID NO: 2), KTKE (SEQ ID NO: 3), or TKEQ (SEQ ID NO: 4), or a part thereof such as EKT, KTK, TKE or KEQ. In some embodiments, the α-Syn peptide or the epitope is EKTK (SEQ ID NO: 2), KTKE (SEQ ID NO: 3), or TKEQ (SEQ ID NO: 4). In one embodiment, the α-Syn peptide or epitope is EKTK (SEQ ID NO: 2). In another embodiment, the α-Syn peptide or epitope is KTKE (SEQ ID NO: 3). In yet another embodiment, the α-Syn peptide or epitope is TKEQ (SEQ ID NO: 4).

In an embodiment, the epitope comprises or consists of at least two consecutive amino acid residues predominantly involved in binding to the antibody, wherein the at least two consecutive amino acids are EK, or KT, or TK, or KE, or EQ embedded correspondingly within EKTK (SEQ ID NO: 2), or KTKE (SEQ ID NO: 3), or TKEQ (SEQ ID NO: 4).

In another embodiment, the epitope is a conformational epitope and consists of EKTK (SEQ ID NO: 2), KTKE (SEQ ID NO: 3), or TKEQ (SEQ ID NO: 4). In an embodiment, the antibody selectively binds EKTK (SEQ ID NO: 2), KTKE (SEQ ID NO: 3), or TKEQ (SEQ ID NO: 4) in a cyclic peptide, optionally cyclo(CGTKEQGGGG) (SEQ ID NO: 7), cyclo(CGGTKEQGG) SEQ ID NO: 48, cyclo(CGGTKEQGGGG) SEQ ID NO:49, cyclo (CGGGEKTKGG) SEQ ID NO: 10, or cyclo (CGGGGEKTKGG) SEQ ID NO: 5 relative to a corresponding linear compound.

In an embodiment, the antibody selectively binds the α-Syn peptide or epitope in a cyclic compound, the α-Syn peptide comprising or consisting of EKTK (SEQ ID NO: 2), KTKE (SEQ ID NO: 3), or TKEQ (SEQ ID NO: 4), optionally in the context of cyclo(CGTKEQGGGG) (SEQ ID NO: 7) or other cyclic peptide sequence listed in Table 2-4 relative to the corresponding linear peptide and/or monomeric or insoluble fibrillar α-Syn. For example, in an embodiment the antibody selectively binds TKEQ (SEQ ID NO: 4) in a cyclic compound, optionally a cyclic peptide such as cyclo(CGTKEQGGGG) (SEQ ID NO: 7) and has at least 2 fold, at least 5 fold, at least 10 fold at least 20 fold, at least 30 fold, at least 40 fold, at least 50 fold, at least 100 fold, at least 500 fold, at least 1000 fold more selective greater selectivity (e.g. binding affinity) for TKEQ (SEQ ID NO: 4) in the cyclic conformation compared to TKEQ (SEQ ID NO: 4) in the corresponding linear peptide and/or monomeric or insoluble fibrillar α-Syn, for example as measured by ELISA or surface plasmon resonance, optionally using a method described herein.

In an embodiment, the antibody selectively binds the α-Syn peptide or epitope in misfolded oligomeric α-Syn polypeptide relative to native α-Syn. In an embodiment, the selectivity is at least 2 fold, at least 3 fold, at least 5 fold, at least 10 fold, at least 20 fold, at least 30 fold, at least 40 fold, at least 50 fold, at least 100 fold, at least 500 fold, at least 1000 fold more selective for misfolded oligomeric α-Syn polypeptide over a monomeric or insoluble fibrillar α-Syn.

In an embodiment, the antibody comprises a heavy chain variable region and/or a light chain variable region, the heavy chain variable region comprising complementarity determining regions CDR-H1, CDR-H2 and CDR-H3, and the light chain variable region comprising complementarity determining regions CDR-L1, CDR-L2 and CDR-L3 with the amino acid sequences of one or more of said CDRs being selected from the amino acid sequences set forth below:
- CDR-H1: SEQ ID NOs: 61, 67, 73, 79 91 or 180;
- CDR-H2: SEQ ID NOs: 62, 68, 74, 80 92 or 181;
- CDR-H3: SEQ ID NOs: 63, 69, 75, 81 93 or 182;
- CDR-L1: SEQ ID NOs: 64, 70, 76 94 or 183;
- CDR-L2: SEQ ID NOs: 65, 71 or 77; or
- CDR-L3: SEQ ID NOs: 66, 72, 78, 84, 96 or 184.

In an embodiment, the antibody comprises a heavy chain variable region and/or a light chain variable region, the heavy chain variable region comprising complementarity determining regions CDR-H1, CDR-H2 and CDR-H3, and the light chain variable region comprising complementarity determining regions CDR-L1, CDR-L2 and CDR-L3 with the amino acid sequence of CDR3 selected from SEQ ID NOs: 63, 69, 75, 81 93 or 182; wherein the antibody selectively binds an α-Syn peptide or epitope described herein in misfolded oligomeric α-Syn relative to native α-Syn.

In one embodiment, the antibody comprises complementarity determining regions CDR-H1, CDR-H2, CDR-H3, CDR-L1, CDR-L2 and CDR-L3 with the amino acid sequences of one or more of said CDRs being selected from the amino acid sequences of SEQ ID NOs: 61-66.

In a specific embodiment, the antibody comprises complementarity determining regions CDR-H1, CDR-H2, CDR-H3, CDR-L1, CDR-L2 and CDR-L3 having amino acid sequences SEQ ID NO: 61, 62, 63, 64, 65 and 66, respectively.

In another embodiment, the antibody comprises complementarity determining regions CDR-H1, CDR-H2, CDR-H3, CDR-L1, CDR-L2 and CDR-L3 with the amino acid sequences of one or more of said CDRs being selected from the amino acid sequences of SEQ ID NOs: 67-72.

In a specific embodiment, the antibody comprises complementarity determining regions CDR-H1, CDR-H2, CDR-H3, CDR-L1, CDR-L2 and CDR-L3 having amino acid sequences SEQ ID NO: 67, 68, 69, 70, 71 and 72, respectively.

In another embodiment, the antibody comprises complementarity determining regions CDR-H1, CDR-H2, CDR-H3, CDR-L1, CDR-L2 and CDR-L3 with the amino acid sequences of one or more of said CDRs being selected from the amino acid sequences of SEQ ID NOs: 73-78.

In a specific embodiment, the antibody comprises complementarity determining regions CDR-H1, CDR-H2, CDR-H3, CDR-L1, CDR-L2 and CDR-L3 having amino acid sequences SEQ ID NO: 73, 74, 75, 76, 77 and 78, respectively.

In another embodiment, the antibody comprises complementarity determining regions CDR-H1, CDR-H2, CDR-H3, CDR-L1, CDR-L2 and CDR-L3 with the amino acid sequences of one or more of said CDRs being selected from the amino acid sequences of SEQ ID NOs: 76-77, 79-81, and 84.

In a specific embodiment, the antibody comprises complementarity determining regions CDR-H1, CDR-H2, CDR-H3, CDR-L1, CDR-L2 and CDR-L3 having amino acid sequences SEQ ID NO: 76-77, 79, 80, 81, and 84, respectively.

In another embodiment, the antibody comprises complementarity determining regions CDR-H1, CDR-H2, CDR-H3, CDR-L1, CDR-L2 and CDR-L3 with the amino acid sequences of one or more of said CDRs being selected from the amino acid sequences of SEQ ID NOs: 79-81, 76-77 and 84.

In a specific embodiment, the antibody comprises complementarity determining regions CDR-H1, CDR-H2, CDR-H3, CDR-L1, CDR-L2 and CDR-L3 having amino acid sequences SEQ ID NO: 79, 80, 81, 76, 77 and 84, respectively.

In another embodiment, the antibody comprises complementarity determining regions CDR-H1, CDR-H2, CDR-H3, CDR-L1, CDR-L2 and CDR-L3 with the amino acid sequences of one or more of said CDRs being selected from the amino acid sequences of SEQ ID NOs: 71, 91-94, and 96.

In a specific embodiment, the antibody comprises complementarity determining regions CDR-H1, CDR-H2, CDR-H3, CDR-L1, CDR-L2 and CDR-L3 having amino acid sequences SEQ ID NO: 91, 92, 93, 94, 71 and 96, respectively.

In another embodiment, the antibody comprises complementarity determining regions CDR-H1, CDR-H2, CDR-H3, CDR-L1, CDR-L2 and CDR-L3 with the amino acid sequences of one or more of said CDRs being selected from the amino acid sequences SEQ ID NO: 180, 181,182, 183, 77 and 184.

In a specific embodiment, the antibody comprises complementarity determining regions CDR-H1, CDR-H2, CDR-H3, CDR-L1, CDR-L2 and CDR-L3 having amino acid sequences SEQ ID NO: 180, 181,182, 183, 77 and 184, respectively.

In another embodiment, the antibody comprises a heavy chain variable region comprising an amino acid sequence of any one of SEQ ID NOs: 133, 135, 137, 139, 141, 143 and 190; or an amino acid sequence having at least 80%, 90%, 95% or 98% sequence identity to any one of SEQ ID NOs: 133, 135, 137, 139, 141, 143 and 190, wherein the CDR sequences are maintained.

In another embodiment, the antibody comprises a heavy chain variable region comprising an amino acid sequence of SEQ ID NO: 133; or an amino acid sequence having at least 80%, 90%, 95% or 98% sequence identity to SEQ ID NO: 133. In another embodiment, the antibody comprises a heavy chain variable region comprising an amino acid sequence of SEQ ID NO: 135; or an amino acid sequence having at least 80%, 90%, 95% or 98% sequence identity to SEQ ID NO: 135. In another embodiment, the antibody comprises a heavy chain variable region comprising an amino acid sequence of SEQ ID NO: 137; or an amino acid sequence having at least 80%, 90%, 95% or 98% sequence identity to SEQ ID NO: 137. In another embodiment, the antibody comprises a heavy chain variable region comprising an amino acid sequence of SEQ ID NO: 139; or an amino acid sequence having at least 80%, 90%, 95% or 98% sequence identity to SEQ ID NO: 139. In another embodiment, the antibody comprises a heavy chain variable region comprising an amino acid sequence of SEQ ID NO: 141; or an amino acid sequence having at least 80%, 90%, 95% or 98% sequence identity to SEQ ID NO: 141. In another embodiment, the antibody comprises a heavy chain variable region comprising an amino acid sequence of SEQ ID NO: 143; or an amino acid sequence having at least 80%, 90%, 95% or 98% sequence identity to SEQ ID NO: 143. In a further embodiment, the antibody comprises a heavy chain variable region comprising an amino acid sequence of SEQ ID NO: 190; or an amino acid sequence having at least 80%, 90%, 95% or 98% sequence identity to SEQ ID NO: 190.

In an embodiment, the light chain variable region comprises an amino acid sequence of any one of SEQ ID NOs: 134, 136, 138, 140, 142, 144 and 191; or an amino acid sequence having at least 80%, 90%, 95% or 98% sequence identity to any one of SEQ ID NOs: 134, 136, 138, 140, 142, 144 and 191, wherein the CDR sequences are maintained.

In another embodiment, the light chain variable region comprises an amino acid sequence of SEQ ID NO: 134; or an amino acid sequence having at least 80%, 90%, 95% or 98% sequence identity to any one of SEQ ID NO: 134. In another embodiment, the light chain variable region comprises an amino acid sequence of SEQ ID NO: 136; or an amino acid sequence having at least 80%, 90%, 95% or 98% sequence identity to any one of SEQ ID NO: 136. In another embodiment, the light chain variable region comprises an amino acid sequence of SEQ ID NO: 138; or an amino acid sequence having at least 80%, 90%, 95% or 98% sequence identity to any one of SEQ ID NO: 138. In another embodiment, the light chain variable region comprises an amino acid sequence of SEQ ID NO: 140; or an amino acid sequence having at least 80%, 90%, 95% or 98% sequence identity to any one of SEQ ID NO: 140. In another embodiment, the light chain variable region comprises an amino acid sequence of SEQ ID NO: 142; or an amino acid sequence having at least 80%, 90%, 95% or 98% sequence identity to any one of SEQ ID NO: 142. In another embodiment, the light chain variable region comprises an amino acid sequence of SEQ ID NO: 144; or an amino acid sequence having at least 80%, 90%, 95% or 98% sequence identity to any one of SEQ ID NO: 144. In another embodiment, the light chain variable region comprises an amino acid sequence of SEQ ID NO: 191; or an amino acid sequence having at least 80%, 90%, 95% or 98% sequence identity to any one of SEQ ID NO: 191.

In another embodiment, the heavy chain variable region and light chain variable region are amino acid sequences of SEQ ID NO: 133, or an amino acid sequence having at least 80%, 90%, 95% or 98% sequence identity to SEQ ID NO: 133; and SEQ ID NO: 134, or an amino acid sequence having at least 80%, 90%, 95% or 98% sequence identity to SEQ ID NO: 134, respectively. In another embodiment, the heavy chain variable region and light chain variable region are amino acid sequences of SEQ ID NO: 135, or an amino acid sequence having at least 80%, 90%, 95% or 98% sequence identity to SEQ ID NO: 135; and SEQ ID NO: 136, or an amino acid sequence having at least 80%, 90%, 95% or 98% sequence identity to SEQ ID NO: 136, respectively. In another embodiment, the heavy chain variable region and light chain variable region are amino acid sequences of SEQ ID NO: 137, or an amino acid sequence having at least 80%, 90%, 95% or 98% sequence identity to SEQ ID NO: 137; and SEQ ID NO: 138, or an amino acid sequence having at least 80%, 90%, 95% or 98% sequence identity to SEQ ID NO: 138, respectively. In another embodiment, the heavy chain variable region and light chain variable region are amino acid sequences of SEQ ID NO: 139, or an amino acid sequence having at least 80%, 90%, 95% or 98% sequence identity to SEQ ID NO: 139; and SEQ ID NO: 140, or an amino acid sequence having at least 80%, 90%, 95% or 98% sequence identity to SEQ ID NO: 140, respectively. In another embodiment, the heavy chain variable region and light chain variable region are amino acid sequences of SEQ ID NO: 141, or an amino acid sequence having at least 80%, 90%, 95% or 98% sequence identity to SEQ ID NO: 141; and SEQ ID NO: 142, or an amino acid sequence having at least 80%, 90%, 95% or 98% sequence identity to SEQ ID NO: 142, respectively. In another embodiment, the heavy chain variable region and light chain variable region are amino acid sequences of SEQ ID NO: 143, or an amino acid sequence having at least 80%, 90%, 95% or 98% sequence identity to SEQ ID NO: 143; and SEQ ID NO: 144, or an amino acid sequence having at least 80%, 90%, 95% or 98% sequence identity to SEQ ID NO: 144, respectively. In another embodiment, the heavy chain variable region and light chain variable region are amino acid sequences of SEQ ID NO: 190, or an amino acid sequence having at least 80%, 90%, 95% or 98% sequence identity to SEQ ID NO: 190; and SEQ ID NO: 191, or an amino acid sequence having at least 80%, 90%, 95% or 98% sequence identity to SEQ ID NO: 191, respectively.

Tables 13 and 14 below set out the nucleic acid and amino acid sequences of complementarity determining regions (CDRs) and of the heavy and light chains, respectively, of each of the antibody clones 2E9, 9D8, 12G1, 3C11, 12B12, 10D5 and 11B6, as determined according to IgBLAST. CDRs of heavy and light chains in Table 14 are shown in bold. In some embodiments, the CDR set, variable region of the heavy and/or the light is as set out therein. In other embodiments, the antibody or nucleic acid comprises the sequence set out therein.

In an embodiment, the antibody is selected from the group consisting of a monoclonal antibody, an immunoglobulin molecule, a Fab, a Fab', a F(ab)2, a F(ab')2, a Fv, a disulfide linked Fv, a scFv, a disulfide linked scFv, a single chain antibody, single domain antibody, a diabody, a dimer, a minibody, a bispecific antibody fragment, a chimeric antibody, a humanized antibody and a polyclonal antibody.

In an embodiment, the antibody is a monoclonal antibody.

In an embodiment, the antibody is a humanized antibody.

In an embodiment, the antibody is a single chain antibody, optionally a humanized single chain antibody.

In an embodiment, the antibody is a binding fragment such as a Fab fragment, optionally a humanized Fab fragment.

To produce monoclonal antibodies, antibody producing cells (lymphocytes) can be harvested from a subject immunized with an immunogen described herein, and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121:140-67 (1986)), and screening of combinatorial antibody libraries (Huse et al., Science 246:1275 (1989)). Hybridoma cells can be screened immunochemically for production of antibodies specifically reactive with the desired epitopes and the monoclonal antibodies can be isolated.

Specific antibodies, or antibody fragments, reactive against particular antigens or molecules, may also be generated by screening expression libraries encoding immunoglobulin genes, or portions thereof, expressed in bacteria with cell surface components. For example, complete Fab fragments, VH regions and FV regions can be expressed in bacteria using phage expression libraries (see for example Ward et al., Nature 41:544-546 (1989); Huse et al., Science 246:1275-1281 (1989); and McCafferty et al., Nature 348: 552-554 (1990).

The humanization of antibodies from non-human species has been well described in the literature. See for example EP-B1 0 239400 and Carter & Merchant 1997 (Curr Opin Biotechnol 8, 449-454, 1997 incorporated by reference in their entirety herein). Humanized antibodies are also readily obtained commercially (eg. Scotgen Limited, 2 Holly Road, Twickenham, Middlesex, Great Britain.).

Humanized forms of rodent antibodies are readily generated by CDR grafting (Riechmann et al. Nature, 332:323-327, 1988). In this approach the six CDR loops comprising the antigen binding site of the rodent monoclonal antibody are linked to corresponding human framework regions. CDR grafting often yields antibodies with reduced affinity as the amino acids of the framework regions may influence antigen recognition (Foote & Winter. J Mol Biol, 224: 487-499, 1992). To maintain the affinity of the antibody, it is often necessary to replace certain framework residues by site directed mutagenesis or other recombinant techniques and may be aided by computer modeling of the antigen binding site (Co et al. J Immunol, 152: 2968-2976, 1994).

Humanized forms of antibodies are optionally obtained by resurfacing (Pedersen et al. J Mol Biol, 235: 959-973, 1994). In this approach only the surface residues of a rodent antibody are humanized.

Human antibodies specific to a particular antigen may be identified by a phage display strategy (Jespers et al. Bio/Technology, 12: 899-903, 1994). In one approach, the heavy chain of a rodent antibody directed against a specific antigen is cloned and paired with a repertoire of human light chains for display as Fab fragments on filamentous phage. The phage is selected by binding to antigen. The selected human light chain is subsequently paired with a repertoire of human heavy chains for display on phage, and the phage is again selected by binding to antigen. The result is a human antibody Fab fragment specific to a particular antigen. In another approach, libraries of phage are produced where members display different human antibody fragments (Fab or Fv) on their outer surfaces (Dower et al., WO 91/17271 and McCafferty et al., WO 92/01047). Phage displaying antibodies with a desired specificity are selected by affinity enrichment to a specific antigen. The human Fab or Fv fragment identified from either approach may be recloned for expression as a human antibody in mammalian cells.

Human antibodies are optionally obtained from transgenic animals (U.S. Pat. Nos. 6,150,584; 6,114,598; and 5,770,429). In this approach the heavy chain joining region (JH) gene in a chimeric or germ-line mutant mouse is deleted. Human germ-line immunoglobulin gene array is subsequently transferred to such mutant mice. The resulting transgenic mouse is then capable of generating a full repertoire of human antibodies upon antigen challenge.

Humanized or human antibodies are selected from any class of immunoglobulins including: IgM, IgG, IgD, IgA or IgE; and any isotype, including: IgG1, IgG2, IgG3 and IgG4. The humanized or human antibody may include sequences from one or more than one isotype or class. Further, these antibodies are typically produced as antigen binding fragments such as Fab, Fab' F(ab')2, Fd, Fv and single domain antibody fragments, or as single chain antibodies in which the heavy and light chains are linked by a linker. Also, the human or humanized antibodies may exist in monomeric or polymeric form. The humanized antibody optionally comprises one non-human chain and one humanized chain (i.e. one humanized heavy or light chain).

Additionally, antibodies specific for the epitopes described herein are readily isolated by screening antibody phage display libraries. For example, an antibody phage library is optionally screened by using a disease specific epitope of the current disclosure to identify antibody fragments specific for the disease specific epitope. Antibody fragments identified are optionally used to produce a variety of recombinant antibodies that are useful with different embodiments of the present disclosure. Antibody phage display libraries are commercially available, for example, through Xoma (Berkeley, California) Methods for screening antibody phage libraries are well known in the art.

Another aspect is an immunoconjugate comprising an antibody herein disclosed and a moiety such as a detectable label or particle.

The detectable label can for example be a polypeptide that is fused to the antibody (e.g. fusion moiety) such as a fluorescent protein or a purification tag such as a FLAG tag, histidine tag, optionally cleavable. For example, the detectable label could be streptavidin, or a fluorescent dye (e.g. Cy3, Cy4, Cy5).

The detectable label can also be positron-emitting radionuclide. Other detectable labels are described elsewhere herein.

The particle can for example be a magnetic particle, such as a magnetic bead, a gold particle, resin or agarose to which the antibody is conjugated. One or more different antibodies described herein can be conjugated to the particle. The antibodies can be conjugated to particles for example by covalent linking through an amine, carboxyl or maleimide functional group.

A further aspect is a nucleic acid encoding the amino acid residues of the compound or immunogen herein described.

A further aspect is a nucleic acid encoding an antibody or immunoconjugate described herein, such as a single chain, single domain and/or humanized antibody, optionally comprised in a vector. Nucleic acid sequences can be determined by sequencing immunoglobulin gene transcripts expressed for example by hybridomas using cDNA generated therefrom using standard RT-PCR and sequencing for example using standard dye-terminator capillary sequencing.

The nucleic acid can also encode any part thereof such as a CDR, comprising for example at least 10 nucleotides. The nucleic acid can also be a primer for amplifying one or more sequences described herein.

The nucleic acid may comprise other comprise such as signal sequences and the like.

In an embodiment, the nucleic acid encoding an antibody comprises a nucleic acid sequence which encodes a heavy chain variable region, the heavy chain variable region comprising complementarity determining regions CDR-H1, CDR-H2 and CDR-H3 with the amino acid sequence of one or more of said CDRs selected from those set forth below:
  CDR-H1: SEQ ID NOs: 61, 67, 73, 79, 91 or 180;
  CDR-H2: SEQ ID NOs: 62, 68, 74, 80, 92 or 181;
  CDR-H3: SEQ ID NOs: 63, 69, 75, 81 93 or 182;
  CDR-L1: SEQ ID NOs: 64, 70, 76, 94 or 183;
  CDR-L2: SEQ ID NOs: 65, 71 or 77; or
  CDR-L3: SEQ ID NOs: 66, 72, 78, 84 96 or 184.

In an embodiment, the nucleic acid encoding an antibody comprises a nucleic acid sequence which encodes a heavy chain variable region, the heavy chain variable region comprising complementarity determining regions CDR-H1, CDR-H2 and CDR-H3 with the amino acid sequence of CDR-H3 selected from SEQ ID NOs: 63, 69, 75, 81 93 and 182.

In an embodiment, the nucleic acid encoding an antibody comprises a nucleic acid sequence which encodes a heavy chain variable region, the heavy chain variable region comprising complementarity determining regions CDR-H1, CDR-H2 and CDR-H3 with the amino acid sequence of one or more of said CDRs being encoded by the nucleic acid sequences set forth below:
CDR-H1: SEQ ID NOs: 97, 103, 109, 115, 127 or 185;
CDR-H2: SEQ ID NOs: 98, 104, 110, 116, 128 or 186; or
CDR-H3: SEQ ID NOs: 99, 105, 111, 117, 123, 129 or 187.

For example, the complementarity determining regions CDR-H1, CDR-H2 and CDR-H3 can be encoded by the nucleic acid sequences SEQ ID NOs: 97-99, respectively. For example, the complementarity determining regions CDR-H1, CDR-H2 and CDR-H3 can be encoded by the nucleic acid sequences SEQ ID NOs: 103-105 respectively. For example, the complementarity determining regions CDR-H1, CDR-H2 and CDR-H3 can be encoded by the nucleic acid sequences SEQ ID NOs: 109-111. For example, the complementarity determining regions CDR-H1, CDR-H2 and CDR-H3 can be encoded by the nucleic acid sequences SEQ ID NOs: 115-117 respectively. For example, the complementarity determining regions CDR-H1, CDR-H2 and CDR-H3 can be encoded by the nucleic acid sequences SEQ ID NOs: 115-116, and 123 respectively. For example, the complementarity determining regions CDR-H1, CDR-H2 and CDR-H3 can be encoded by the nucleic acid sequences selected from SEQ ID NOs: 127-129 respectively. For example, the complementarity determining regions CDR-H1, CDR-H2 and CDR-H3 can be encoded by the nucleic acid sequences SEQ ID NOs: 185-187 respectively.

In another embodiment, the nucleic acid encoding an antibody comprises a nucleic acid which encodes a light chain variable region, the light chain variable region comprising complementarity determining regions CDR-L1, CDR-L2 and CDR-L3 with the amino acid sequence of one or more of said CDRs being encoded by the nucleic acid sequences set forth below:
CDR-L1: SEQ ID NOs: 100, 106, 112, 115, 130 or 188;
CDR-L2: SEQ ID NOs: 101, 107 or 113; or
CDR-L3: SEQ ID NOs: 102, 108, 114, 120, 132, or 189.

For example, the complementarity determining regions CDR-L1, CDR-L2 and CDR-L3 can be encoded by the nucleic acid sequences SEQ ID NOs: 100-102, respectively. For example, the complementarity determining regions CDR-L1, CDR-L2 and CDR-L3 can be encoded by the nucleic acid sequences SEQ ID NOs: 106-108 respectively. For example, the complementarity determining regions CDR-L1, CDR-L2 and CDR-L3 can be encoded by o the nucleic acid sequences SEQ ID NOs: 112-114 respectively. For example, the complementarity determining regions CDR-L1, CDR-L2 and CDR-L3 can be encoded by the nucleic acid sequences SEQ ID NOs: 112-113, and 120 respectively. For example, the complementarity determining regions CDR-L1, CDR-L2 and CDR-L3 can be encoded by the nucleic acid sequences SEQ ID NOs: 112-113, and 120 respectively. For example, the complementarity determining regions CDR-L1, CDR-L2 and CDR-L3 can be encoded by the nucleic acid sequences SEQ ID NOs: 107,130, and 132 respectively. For example, the complementarity determining regions CDR-L1, CDR-L2 and CDR-L3 can be encoded by the nucleic acid sequences SEQ ID NOs: 188, 113, and 189 respectively.

In an embodiment, the nucleic acid encodes an antibody and comprises i) a first nucleic acid molecule encoding a heavy chain variable region, the heavy chain variable region comprising complementarity determining regions CDR-H1, CDR-H2 and CDR-H3 and ii) a second nucleic acid molecule encoding a light chain variable region comprising complementarity determining regions CDR-L1, CDR-L2 and CDR-L3, with the amino acid sequence of one or more of said CDRs being encoded by the nucleic acid sequences set forth below:
CDR-H1: SEQ ID NOs: 97, 103, 109, 115, 127 or 185;
CDR-H2: SEQ ID NOs: 98, 104, 110, 116, 128 or 186;
CDR-H3: SEQ ID NOs: 99, 105, 111, 117, 123, 129 or 187;
CDR-L1: SEQ ID NOs: 100, 106, 112, 130 or 188;
CDR-L2: SEQ ID NOs: 101, 107 or 113; or
CDR-L3: SEQ ID NOs: 102, 108, 114, 120, 132 or 189.

The first nucleic acid molecule and the second nucleic acid molecule may be fused as an expression cassette or comprised in a vector as separate expression cassettes.

The nucleic acid can comprise the CDR sets described herein.

In a specific embodiment, the CDRs CDR-H1, CDR-H2, CDR-H3, CDR-L1, CDR-L1, CDR-L2 and CDR-L3 are encoded by SEQ ID NOs: 97, 98, 99, 100, 101 and 102, respectively.

In a specific embodiment, the CDRs CDR-H1, CDR-H2, CDR-H3, CDR-L1, CDR-L1, CDR-L2 and CDR-L3 are encoded by SEQ ID NOs: 103, 104, 105, 106, 107 and 108, respectively.

In a specific embodiment, the CDRs CDR-H1, CDR-H2, CDR-H3, CDR-L1, CDR-L1, CDR-L2 and CDR-L3 are encoded by SEQ ID NOs: 109, 110, 111, 112, 113 and 114, respectively.

In a specific embodiment, the CDRs CDR-H1, CDR-H2, CDR-H3, CDR-L1, CDR-L1, CDR-L2 and CDR-L3 are encoded by SEQ ID NOs: 115, 116, 117, 112, 113 and 120, respectively.

In a specific embodiment, the CDRs CDR-H1, CDR-H2, CDR-H3, CDR-L1, CDR-L1, CDR-L2 and CDR-L3 are encoded by SEQ ID NOs: 115, 116, 123, 112, 113 and 120, respectively.

In a specific embodiment, the CDRs CDR-H1, CDR-H2, CDR-H3, CDR-L1, CDR-L1, CDR-L2 and CDR-L3 are encoded by SEQ ID NOs: 127, 128, 129, 130, 107 and 132, respectively.

In a specific embodiment, the CDRs CDR-H1, CDR-H2, CDR-H3, CDR-L1, CDR-L1, CDR-L2 and CDR-L3 are encoded by SEQ ID NOs: 185-188, 113 and 189, respectively.

In another embodiment, the heavy chain variable region of the antibody is encoded by a nucleic acid sequence comprising any one of SEQ ID NOs: 145, 147, 149, 151, 153, 155 and 192; a sequence with at least 80%, 90%, 95%, 98% or 99% sequence identity to any of the foregoing wherein the amino acid sequence of the CDR regions are maintained; a sequence encoding any one of SEQ ID NOs: 133, 135, 137, 139, 141, 143 and 190; or encoding an amino acid sequence having at least 80%, 90%, 95% 98% or 99% sequence identity to any one of SEQ ID NOs: 133, 135, 137, 139, 141, 143 and 190, wherein the CDR amino acid sequences are maintained.

In a further embodiment, the light chain variable region of the antibody is encoded by a nucleic acid sequence comprising any one of SEQ ID NOs: 146, 148, 150, 152, 154, 156 and 193, a sequence with at least 80%, 90%, 95%, 98% or 99% sequence identity to any of the foregoing wherein the amino acid sequence of the CDR regions are maintained; a sequence encoding any one of SEQ ID NOs: 134, 136, 138, 140, 142, 144 and 191; or encoding an amino acid sequence having at least 80%, 90%, 95% or 98% sequence identity to any one of SEQ ID NOs: 134, 136, 138, 140, 142, 144 and 191, wherein the CDR sequences are maintained.

In an embodiment, the nucleic acid is an isolated nucleic acid.

The vector can be any vector, including vectors suitable for producing an antibody or expressing a peptide sequence described herein.

The nucleic acid molecules may be incorporated in a known manner into an appropriate expression vector which ensures expression of the protein. Possible expression vectors include but are not limited to cosmids, plasmids, or modified viruses (e.g. replication defective retroviruses, adenoviruses and adeno-associated viruses). The vector should be compatible with the host cell used. The expression vectors are suitable for transformation of a host cell, which means that the expression vectors contain a nucleic acid molecule encoding antibodies described herein. For example, the nucleic acid molecules encoding the heavy chain variable region and the light chain variable region may be inserted into separate vectors. For example, the nucleic acid molecules encoding the heavy chain variable region and the light chain variable region may be inserted into the same expression vector.

In an embodiment, the vector comprises one or more of the nucleic acid sequences encoding any amino acid sequence described herein or comprising any nucleic acid described herein for example one or more of SEQ ID NOs: 97-117, 120, 123, 127-130, 132, 145-156 and 185-189.

In an embodiment, the vector is suitable for expressing for example single chain antibodies by gene therapy. The vector can be adapted for specific expression in neural tissue, for example using neural specific promoters and the like. In an embodiment, the vector comprises an IRES and allows for expression of a light chain variable region and a heavy chain variable region. Such vectors can be used to deliver antibody in vivo.

Suitable regulatory sequences may be derived from a variety of sources, including bacterial, fungal, viral, mammalian, or insect genes.

Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

In an embodiment, the regulatory sequences direct or increase expression in neural tissue and/or cells.

In an embodiment, the vector is a viral vector.

The recombinant expression vectors may also contain a marker gene which facilitates the selection of host cells transformed, infected or transfected with a vector for expressing an antibody or epitope peptide described herein.

The recombinant expression vectors may also contain expression cassettes which encode a fusion moiety (i.e. a "fusion protein") which provides increased expression or stability of the recombinant peptide; increased solubility of the recombinant peptide; and aid in the purification of the target recombinant peptide by acting as a ligand in affinity purification, including for example tags and labels described herein. Further, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, MA) and pRIT5 (Pharmacia, Piscataway, NJ) which fuse glutathione S-transferase (GST), maltose E binding protein, or protein A, respectively, to the recombinant protein.

Systems for the transfer of genes for example into neurons and neural tissue both in vitro and in vivo include vectors based on viruses, most notably Herpes Simplex Virus, Adenovirus, Adeno-associated virus (AAV) and retroviruses including lentiviruses. Alternative approaches for gene delivery include the use of naked, plasmid DNA as well as liposome-DNA complexes. Another approach is the use of AAV plasmids in which the DNA is polycation-condensed and lipid entrapped and introduced into the brain by intracerebral gene delivery (Leone et al. U.S. Application No. 2002076394).

In an embodiment, the vector comprises a nucleic acid sequence comprising a signal sequence (permitting intracellular antibody expression). Any signal peptide suitable for expression of a secretable chain precursor that enables proper externalization with folding and disulfide formation to elaborate the desired antibody as a secreted, dimerized and processed protein may be used. For example the signal sequence is chosen from any one of SEQ ID NOs: 157 to 164, 169-177, and 179.

In an embodiment, the vector comprises a nucleic acid sequence deleted of signal sequence, optionally one in Table 15.

Also provided in another aspect is a cell expressing an antibody described herein.

In an embodiment, the cell is a fused cell such as a hybridoma.

In an embodiment, the cell is a recombinant cell. In an embodiment, the cell is a mammalian cell, optionally a CHO cell.

The recombinant cell can be generated using any cell suitable for producing a polypeptide, for example suitable for producing an antibody and/or binding fragment thereof.

Suitable host cells include a wide variety of prokaryotic and eukaryotic host cells. For example, the proteins may be expressed in bacterial cells such as *E. coli*, insect cells (using baculovirus), yeast cells or mammalian cells.

More particularly, bacterial host cells suitable for producing recombinant antibody producing cells include *E. coli, B. subtilis, Salmonella typhimurium*, and various species within the genus *Pseudomonas, Streptomyces*, and *Staphylococcus*, as well as many other bacterial species well known to one of ordinary skill in the art. Suitable bacterial expression vectors preferably comprise a promoter which functions in the host cell, one or more selectable phenotypic markers, and a bacterial origin of replication. Representative promoters include the ß-lactamase (penicillinase) and lactose promoter system, the trp promoter and the tac promoter. Representative selectable markers include various antibiotic resistance markers such as the kanamycin or ampicillin resistance genes. Suitable expression vectors include but are not limited to bacteriophages such as lambda derivatives or plasmids such as pBR322, the pUC plasmids pUC18, pUC19, pUC118, pUC119, and pNH8A, pNH16a, pNH18a, and Bluescript M13 (Stratagene, La Jolla, CA).

Suitable yeast and fungi host cells include, but are not limited to *Saccharomyces cerevisiae, Schizosaccharomyces pombe*, the genera *Pichia* or *Kluyveromyces* and various species of the genus *Aspergillus*. Examples of vectors for expression in yeast *S. cerivisiae* include pYepSec1, pMFa, pJRY88, and pYES2 (Invitrogen Corporation, San Diego, CA). Protocols for the transformation of yeast and fungi are well known to those of ordinary skill in the art.

Suitable mammalian cells include, among others: COS (e.g., ATCC No. CRL 1650 or 1651), BHK (e.g. ATCC No.

CRL 6281), CHO (ATCC No. CCL 61), HeLa (e.g., ATCC No. CCL 2), 293 (ATCC No. 1573), NS-1 cells and any derivatives of these lines.

In an embodiment, the mammalian cells used to produce a recombinant antibody are selected from CHO, HEK293 cells or Freestyle™ 293-F cells (Life technologies). Free-Style 293-F cell line is derived from the 293 cell line and can be used with the FreeStyle™ MAX 293 Expression System, FreeStyle™ 293 Expression System or other expression systems.

Suitable expression vectors for directing expression in mammalian cells generally include a promoter (e.g., derived from viral material such as polyoma, Adenovirus 2, cytomegalovirus and Simian Virus 40), as well as other transcriptional and translational control sequences.

Suitable insect cells include cells and cell lines from *Bombyx* or *Spodotera* species. Baculovirus vectors available for expression of proteins in cultured insect cells (SF 9 cells) include the pAc series and the pVL series.

The recombinant expression vectors may also contain genes which encode a fusion moiety (i.e. a "fusion protein") which provides increased expression or stability of the recombinant peptide; increased solubility of the recombinant peptide; and aid in the purification of the target recombinant peptide by acting as a ligand in affinity purification, including for example tags and labels described herein. Further, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMAL (New England Biolabs, Beverly, MA) and pRIT5 (Pharmacia, Piscataway, NJ) which fuse glutathione S-transferase (GST), maltose E binding protein, or protein A, respectively, to the recombinant protein.

In an embodiment, expression of the antibody or binding fragment thereof is under the control of an inducible promoter. Examples of inducible non-fusion expression vectors include pTrc (ThermoFisher Scientific) and pET 11d.

The recombinant expression vectors may also contain a marker gene which facilitates the selection of host cells transformed or transfected with a recombinant molecule of the invention. Examples of selectable marker genes are genes encoding a protein such as G418 and hygromycin which confer resistance to certain drugs, ß-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as ß-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest. Other selectable markers include fluorescent proteins such as GFP which may be cotransduced with the nucleic acid of interest.

IV. Compositions

A further aspect is a composition comprising a compound, an immunogen, an immunoconjugate, an antibody, a nucleic acid, a vector and/or a cell described herein. The composition comprise 2 or more, 3 more or any combination of components described herein. For example the composition can comprise two or more antibodies, two or more immunoconjugates, two or more immunogens etc.

In an embodiment, the composition comprises a diluent. Suitable diluents for polypeptides, including antibodies and/or cells include but are not limited to saline solutions, pH buffered solutions and glycerol solutions or other solutions suitable for freezing polypeptides and/or cells. Suitable diluents for nucleic acids include but are not limited to water, saline solutions and ethanol.

In an embodiment, the composition comprises a pharmaceutically acceptable carrier, diluent, and/or excipient. In an embodiment, the composition is a pharmaceutical composition, for example for a method described herein such as for treating a subject with a synucleinopathy or in need of inhibiting misfolded α-synuclein toxicity.

One or more antibodies can be administered in combination or with other treatments for a condition or disease described herein.

The compositions described herein can be prepared by per se known methods for the preparation of pharmaceutically acceptable compositions that can be administered to subjects, optionally as a vaccine, such that an effective quantity of the active substance is combined in a mixture with a pharmaceutically acceptable vehicle.

In an embodiment comprising a compound or immunogen described herein, the composition comprises an adjuvant.

Adjuvants that can be used for example, include Intrinsic adjuvants (such as lipopolysaccharides) normally are the components of killed or attenuated bacteria used as vaccines. Extrinsic adjuvants are immunomodulators which are typically non-covalently linked to antigens and are formulated to enhance the host immune responses. Aluminum hydroxide, aluminum sulfate and aluminum phosphate (collectively commonly referred to as alum) are routinely used as adjuvants. A wide range of extrinsic adjuvants can provoke potent immune responses to immunogens. These include saponins such as Stimulons (QS21, Aquila, Worcester, Mass.) or particles generated therefrom such as ISCOMs and (immunostimulating complexes) and ISCOMATRIX, complexed to membrane protein antigens (immune stimulating complexes), pluronic polymers with mineral oil, killed mycobacteria and mineral oil, Freund's complete adjuvant, bacterial products such as muramyl dipeptide (MDP) and lipopolysaccharide (LPS), as well as lipid A, and liposomes.

In an embodiment, the adjuvant is aluminum hydroxide. In another embodiment, the adjuvant is aluminum phosphate. Oil in water emulsions include squalene; peanut oil; MF59 (WO 90/14387); SAF (Syntex Laboratories, Palo Alto, Calif.); and Ribi™ (Ribi Immunochem, Hamilton, Mont.). Oil in water emulsions may be used with immunostimulating agents such as muramyl peptides (for example, N-acetylmuramyl-L-threonyl-D-isoglutamine (thr-MDP), -acetyl-normuramyl-L-alanyl-D-isoglutamine (nor-MDP), N-acetylmuramyl-L-alanyl-D-isoglutamyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components.

The adjuvant may be administered with an immunogen as a single composition. Alternatively, an adjuvant may be administered before, concurrent and/or after administration of the immunogen.

In an embodiment, the composition comprises an antibody described herein. In another embodiment, the composition comprises an antibody described herein and a diluent. In an embodiment, the composition is a sterile composition.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The composition may be supplied, for example but not by way of limitation, as a lyophilized powder which is reconstituted with sterile water or saline or other pharmaceutically acceptable diluent prior to administration to the patient.

Pharmaceutical compositions may comprise a pharmaceutically acceptable carrier. Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N, N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

The term "compound as used herein" can refer for example to the peptide, immunogen, antibody, immunoconjugate etc.

Another aspect includes an antibody complex comprising an antibody described herein and alph-syn (e.g. misfolded alpha-syn oligomers or soluble fibrils). The complex may be in solution.

V. Kits

A further aspect relates to a kit comprising i) an antibody or immunoconjugate, ii) a nucleic acid or vector, iii) a peptide, cyclic compound or immunogen, iv) a composition and/or v) recombinant cell described herein, comprised for example in a vial such as a sterile vial or other housing and optionally a reference agent and/or instructions for use thereof.

The kit can comprise an antibody described herein and a particle, such as a bead, a plate, such as multiwell plate for an immunoassay or other matrices. The antibody can be conjugated thereto or provided separately with one or more coupling reagents.

The kit can comprise one or more reagents such as a test sample preparatory or dilution solution, a complex formation solution, or a wash solution for washing unbound antibody, one or more detection reagents or a coupling.

The reagent may be a reagent described herein, for example described in the Examples.

The kit can for example be for use with a method or methods described herein.

The compounds, immunogens, antibodies, immunoconjugates, nucleic acids, vectors, cells compositions and kits described herein can be used for inhibiting misfolded alpha-syn toxicity, for treating a synucleinopathy or other method or assay described herein. They can also be used in the manufacture of a medicament for the inhibiting misfolded alpha-syn toxicity, for treating a synucleinopathy or other method or assay described herein.

VI. Methods and Assays

Included are methods for making the compounds, immunogens, nucleic acid, vectors, antibodies and immunoconjugates described herein.

In particular, provided are methods of making an antibody selective for a conformational epitope in EKTKEQ (SEQ ID NO: 1), EKTK (SEQ ID NO: 2), KTKE (SEQ ID NO: 3), TKEQ (SEQ ID NO: 4), or related epitope.

In one embodiment, the method comprises administering a cyclic compound or immunogen described herein or a composition comprising the cyclic compound or the immunogen to a subject and isolating antibody and/or cells expressing antibody specific for the cyclic compound or immunogen administered, optionally selecting and/or isolating one or more antibodies that selectively bind misfolded oligomeric alpha-Syn polypeptide.

As mentioned above, the antibody herein described comprises a heavy chain variable region and/or a light chain variable region, the heavy chain variable region comprising complementarity determining regions CDR-H1, CDR-H2 and CDR-H3, and the light chain variable region comprising complementarity determining regions CDR-L1, CDR-L2 and CDR-L3 with the amino acid sequence of said CDRs being selected from the amino acid sequences set forth below:

CDR-H1: SEQ ID NOs: 61, 67, 73, 79, 91 or 180;
CDR-H2: SEQ ID NOs: 62, 68, 74, 80, 92 or 181;
CDR-H3: SEQ ID NOs: 63, 69, 75, 81, 93 or 182;
CDR-L1: SEQ ID NOs: 64, 70, 76, 94 or 183;
CDR-L2: SEQ ID NOs: 65, 71 or 77; or
CDR-L3: SEQ ID NOs: 66, 72, 78, 84, 96 or 184.

The antibody can comprise any of the CDR sets or variable regions described herein.

In another embodiment, the produced antibody is isolated and purified.

In another embodiment, the isolated and purified antibody is affinity matured. Affinity maturation can be performed as described for the initial selection, with antigen adsorbed to plastic plates, using a for example a phage library comprising variants of the CDR sequences.

A person skilled in the art will appreciate that several methods can be used to produce antibodies with specific binding affinity to misfolded oligomeric α-synuclein. A method that can be used is a phage display method.

A further aspect provides an assay for detecting whether a test sample comprises misfolded oligomeric α-Syn for example, wherein EKTK (SEQ ID NO: 2), KTKE (SEQ ID NO: 3), or TKEQ (SEQ ID NO: 4) or related conformational epitope comprises at least one of the residues E57, K58, T59, K60, E61, or Q62 is in an alternate conformation than occupied by E57, K58, T59, K60, E61, and/or Q62 in a non-misfolded proteinic conformation (e.g. native monomers and tetramers) or insoluble fibrils.

In an embodiment, the assay comprises:
a. contacting the test sample with the antibody described herein under conditions permissive to produce an antibody:misfolded oligomeric α-Syn polypeptide complex; and
b. detecting the presence of any complex;
wherein the presence of detectable complex is indicative that the test sample may contain misfolded oligomeric α-Syn polypeptide.

In another embodiment, the assay comprises:

a. contacting a test sample of said subject with an antibody or immunoconjugate described herein, under conditions permissive to produce an antibody-antigen complex;
b. quantitating the amount of the antibody-antigen complex in the test sample; and
c. comparing the amount of antibody-antigen complex in the test sample to a control.

For example, the comparison to a control can indicate if the test sample comprises misfolded α-Syn such as misfolded oligomeric α-Syn.

In an embodiment, the test sample comprises brain tissue or an extract thereof, saliva, and/or CSF. In an embodiment, the test sample is obtained from a human subject.

The control can be a range or cut-off value derived from a control population known as having or not having the disease. The assay can also include a negative control or a positive control (such as recombinant misfolded oligomeric alpha-syn or cyclic peptide).

For example, a negative control sample can be included in the assay to provide background values for the assay. Results obtained with test samples can be compared to the values obtained with a control population (e.g. the control). The control can for example be a range or a cut-off value determined from control subjects that are for example age matched and which are known as not having or having the synucleinopathy of the subject from whom the test sample is obtained. Comparisons can also be made to one or more previous levels in methods involving monitoring disease progression.

In some embodiments, the test sample is from a subject with comprising a genetic mutation in the alpha-synuclein gene.

In another embodiment, the test sample is from a subject with or suspected of having a synucleinopathy, optionally Parkinson's disease, dementia with Lewy bodies, or multiple system atrophy.

A number of methods can be used to determine if misfolded oligomeric α-Syn polypeptide is present in a test sample using the antibodies described herein, including immunoassays such as flow cytometry, dot blot, Western blots, ELISA, and immunoprecipitation followed by SDS-PAGE immunocytochemistry and other detection platform (e.g. SIMOA, MSD, etc).

Detection of misfolded oligomeric α-Syn polypeptide in a test sample using a number of methods could be used for diagnosis and treatment tracking of synucleinopathies, including Parkinson's disease (PD), dementia with Lewy bodies (DLB), and multiple system atrophy (MSA). Assays that can detect in the range of for example 1-1000 pg/ml of a sample may be useful. For example, the "Single Molecule Counting" (SMC™) platform from EMD Millipore is ultrasensitive and suitable for detection of low abundance biomarkers such as misfolded oligomeric α-Syn.

In some embodiments, immunoconjugates comprising particles such as magnetic beads coated with an α-Syn-antibody or antibodies described herein are used to capture α-Syn from the test samples. As the antibodies described herein selectively bind toxigenic oligomeric species relative to monomeric species, the method limits interference by physiologically abundant monomers. The measuring step can comprise detecting the captured misfolded oligomeric α-Syn with a pan-α-Syn antibody that comprises for example a label such as any of the detectable labels described elsewhere, followed by elution of the bound detector antibody for quantitation of signal from the label. The signal determined is proportional to the amount of misfolded oligomeric α-Syn polypeptide in the sample such that the amount can be calculated from a standard curve. Comparison to a range or cut-off value obtained with normal control samples can be used for diagnostic purposes while longitudinal measurements can be used to assess efficacy of treatment. The feasibility of this approach has been established using soluble MSA brain extract (Example 19).

As described in the Examples surface plasmon resonance can be used to assess conformation specific binding.

A further aspect includes a method of inducing an immune response in a subject, comprising administering to the subject a compound, immunogen and/or composition comprising a compound described herein; and optionally isolating cells and/or antibodies that specifically bind the compound or immunogen administered. The antibodies can be tested using one or more assays described in the Examples.

It is also demonstrated in the Examples, that antibodies of the disclosure, were able to inhibit the toxicity of misfolded alpha-Syn oligomers in a Parkinson's disease rat dopaminergic neural assay. Further, it is also demonstrated herein that antibodies of the disclosure can prevent alpha-synuclein aggregation and phosphorylation induced by exposure to small soluble fibrils (sonicated synthetic preformed fibrils (PFFs)) in a hippocampal neuron culture model of Parkinson's disease. For example as shown in Example 11, the antibodies of the disclosure were able to reduce the amount of synthetic alpha-syn internalized and the recruitment of endogenous alpha-syn to a pathological phosphorylated form induced by the exposure to PFFs.

Recently it was also shown that mice expressing the familial PD E46K mutation plus 2 homologous E→K mutations in adjacent KTK EGV sequence had disrupted tetramers and produced an increased number of monomers (Nuber 2018). The inability to form physiological tetramers in these mice caused a Parkinson's-like disorder.

Accordingly another aspect is a method of inhibiting misfolded alpha-syn toxicity and/or propagation comprising administering an effective amount of an antibody, immunoconjugate or composition comprising said antibody or immunoconjugate described herein to a cell population and/or subject in need thereof, wherein the antibody selectively binds misfolded oligomeric alpha-Syn but not physiological tetramers, for example determined using an assay described herein or inhibits misfolded oligomeric alpha-Syn toxicity for example as assessed in a dopaminergic neural toxicity assay, for example such as the model assay described in the examples.

Also provided is use of an effective amount of an antibody, immunoconjugate or composition comprising said antibody or immunoconjugate described herein for inhibiting misfolded alpha-syn toxicity in a cell population or subject in need thereof, wherein the antibody selectively binds misfolded oligomeric alpha-Syn and/or an epitope sequence in the context of an immunogen described herein.

In an embodiment, method or use is for inhibiting cell to cell transmission of misfolded alpha-syn and/or reducing the amount of endogenous aggregated phosphorylated alpha-syn.

In an embodiment, the cell population is a neural cell population. In an embodiment, the neural cell population is an in vitro model of Parkinson's disease.

In an embodiment, the subject is a human.

In an embodiment, the human has or is suspected of having, or has an increased likelihood of developing Parkinson's disease (PD), Lewy Body disease (LBD, also referred to as dementia with Lewy Bodies or DLB) or multiple system atrophy (MSA) (collectively known as synucleinopathies). For example, a person who carries a mutation associated with familial PD is considered to have an increased likelihood of developing PD.

Also provided is a method of treating a α-synucleinopathy, the method comprising administering to a subject in need thereof an effective amount of an antibody or immunoconjugate of the disclosure described herein, or a composition comprising said antibody or immunoconjugate.

In an embodiment, the α-synucleinopathy is PD, LBD or multiple system atrophy (MSA). Alpha-synuclein has also been implicated in Alzheimer's disease (AD). Accordingly a further aspect is a method of treating a subject with comprising administering to a subject in need thereof an effective amount of an antibody or immunoconjugate of the disclosure described herein, or a composition comprising said antibody or immunoconjugate, optionally in combination with another AD treatment. The another AD treatment can for example be an antibody described in any of WO/2017/079833, WO/2017/079834, WO/2017/079831, WO/2017/079832 and WO/2017/079835 each of which ere filed on Sep. 11, 2016 and which are herein incorporated by reference.

The antibody can for example be comprised in a composition as described herein for example in combination with a pharmaceutically acceptable carrier, diluent and/or excipient and formulated for example in vesicles for improving delivery. Combinations of antibodies (e.g. 2 or more antibodies) and/or immunoconjugates can also be used.

The compositions, antibodies, immunogens and immunoconjugates described herein can be administered for example, by parenteral, intravenous, subcutaneous, intramuscular, intracranial, intraventricular, intrathecal, intraorbital, ophthalmic, intraspinal, intracisternal, intraperitoneal, intranasal, aerosol or oral administration.

In certain embodiments, the composition is administered systemically.

Other embodiments contemplate the co-administration of the compositions, antibodies, and immunoconjugates described herein with biologically active molecules known to facilitate the transport across the blood brain barrier.

Also contemplated in certain embodiments, are methods for administering the compositions, antibodies, and immunoconjugates described herein across the blood brain barrier such as those directed at transiently increasing the permeability of the blood brain barrier as described in U.S. Pat. No. 7,012,061 "Method for increasing the permeability of the blood brain barrier", herein incorporated by reference.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Molecular-dynamics-based simulations which impose a global coordinate bias on a protein (or peptide-aggregate) to force the protein (or peptide-aggregate) to misfold and then predict the most likely unfolded regions of the partially unstructured protein (or peptide aggregate) were used to identify epitopes that are selectively or preferentially displayed in misfolded alpha-synuclein. Biasing simulations were performed and the change in solvent accessible surface area (SASA) corresponding to each residue was measured (compared to that of the initial fibril structure of the protein under consideration). SASA represents the surface area that is accessible to $H_2O$. A positive change in SASA (compared to that of the initial structure of the protein under consideration) may be considered to be indicative of unfolding in the region of the associated residue index. Two other methods were used in addition to SASA to identify candidate epitopes. These were the loss of fibril contacts, defined by non-hydrogen atoms within a cut-off length, and root mean squared fluctuations (RMSF), measuring the extent of deviations about the average in a structural ensemble; here an increase in RMSF for some amino acids indicates an increase in the dynamics of those amino acids.

The methods were applied to the α-Syn fibril (PDB entry 2N0A).

A structure of 10 chains of α-Syn fibril has been determined and is listed on the protein databank as PDB entry 2N0A. The PDB 2N0A structure or any part of it can be equilibrated on a computer to obtain an equilibrium ensemble, which was used for all measurements of the fibril conformations of the epitopes in the fibril structure of α-Syn, referred to herein variably as "structured fibril" or "unbiased fibril structure of α-Syn", "fibril ensemble of α-Syn", "equilibrium fibril ensemble of α-Syn", or "α-Syn fibril structural ensemble".

The monomer ensemble can be obtained for example by taking as a starting structure one of the chains from the PDB fibril (2N0A). A Pivot algorithm is then used to induce large conformational changes to the configuration, and generate 1500 different unfolded structures to be used as initial configurations. For each of these 1500 structures, a 3 ns equilibration simulation was performed, and a snapshot configuration for each 1 ns was collected and added into the monomer ensemble—3 equilibrated snapshots for each initial condition. The net result is a monomer ensemble with 4500 configurations.

Simulations were performed for this initial structure using the collective coordinates method as described in WO/2017/079836 and the CHARMM force-field parameters described in: K. Vanommeslaeghe, E. Hatcher, C.Acharya, S. Kundu, S. Zhong, J. Shim, E. Darian, O. Guvench, P. Lopes, I. Vorobyov, and A. D. Mackerell. Charmm general force field: A force field for drug-like molecules compatible with the CHARMM all-atom additive biological force fields. *Journal of Computational Chemistry*, 31(4):671-690, 2010; and P. Bjelkmar, P. Larsson, M. A. Cuendet, B. Hess, and E. Lindahl. Implementation of the CHARMM force field in GROMACS: analysis of protein stability effects from correlation maps, virtual interaction sites, and water models. *J. Chem. Theo. Comp.*, 6:459-466, 2010, both of which are hereby incorporated herein by reference, with TIP3P water as solvent.

I. Epitope Predictions

Figure 1B:
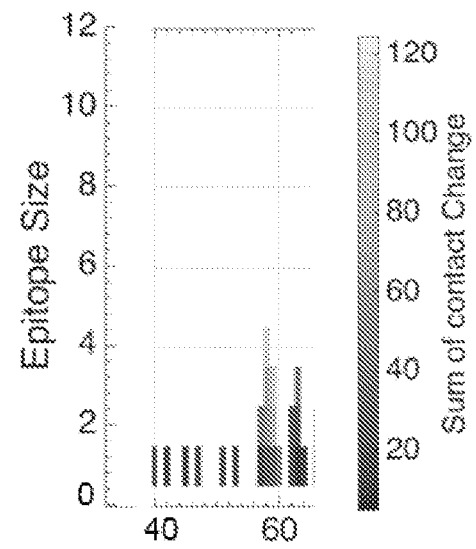

The epitopes EKTK (SEQ ID NO: 2), KTKE (SEQ ID NO: 3), and TKEQ (SEQ ID NO: 4) emerge as predicted epitopes from the PDB structure 2N0A using the collective coordinates approach as shown for example in FIG. 1A and FIG. 1B. The EKTK (SEQ ID NO: 2), KTKE (SEQ ID NO:

3), and TKEQ (SEQ ID NO: 4) epitopes emerge as a prediction for PDB structure 2N0A when considering either increased SASA, loss of fibril contacts, or increased RMSF (FIG. 1 Panel C). Cyclic compounds comprising epitopes EKTK (SEQ ID NO: 2), KTKE (SEQ ID NO: 3) or TKEQ (SEQ ID NO: 4) in an amino acid scaffold (e.g. comprising a linker) were assessed for their suitability for presenting the epitope as described in Example 2 and used for further analysis.

For the plots in FIGS. 1-5 discussed herein, the data are obtained from equilibrium simulations in explicit solvent (TIP3P) using the Charmm36m force field as mentioned above.

FIG. 2 shows the conformation an α-Syn monomer in the context of the unbiased fibril. This structure is the centroid conformation taken from an equilibrium simulation of 5 chains of α-Syn with 100 mM NaCl. Residues K58 and K60 are approximately parallel in this structural ensemble. There is a close contact between the Hε3 atom of K60 (which is weakly positive charged, Q=0.05) and the Nε2 of Q62 (which is negatively charged, Q=−0.64). Panel B shows a snapshot of the structure of an α-Syn monomer in the biased ensemble. Residues K58 and K60 are no longer parallel in this ensemble, and the contact between K60 and Q62 is no longer present.

II. Solvent-Exposure of The Epitope

Figure 1C:
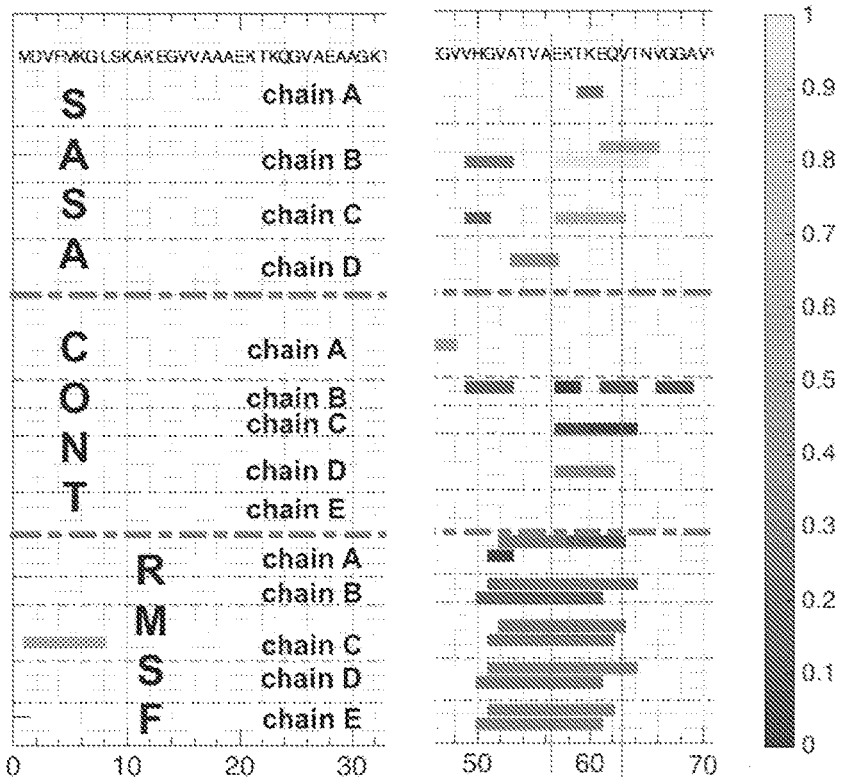
Figure 3A:
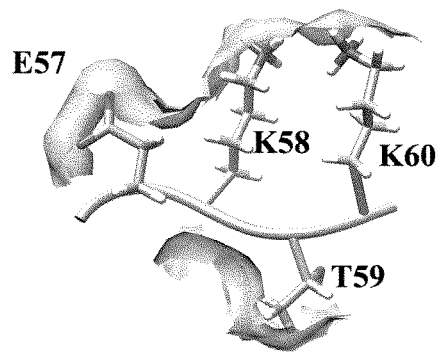
FIGS. 3A-C show schematic representations of different conformations of alpha-synuclein. Panel A shows a snapshot of the EKTK (SEQ ID NO: 2) in the context of the unbiased fibril (PDB 2N0A). The figure also shows the SASA of this region of sequence; the SASA is minimal since the epitope is largely buried. Panel B shows the centroid structure for the ensemble of the cyclic peptide cyclo(CGGGGEKTKGG) (SEQ ID NO: 5). The sidechains in the cyclic peptide show increased SASA relative to the sidechains in the fibril. Panel C shows the side-chain orientations of both instances of the epitope in the centroid structure of the isolated native monomer ensemble. The orientations of T59 and K60, relative to K58, are significantly different in the isolated monomer ensemble than in the cyclic peptide ensemble. The conformation of the epitope is different from the bulk of the conformations in the cyclic peptide ensemble.
Figure 3B:
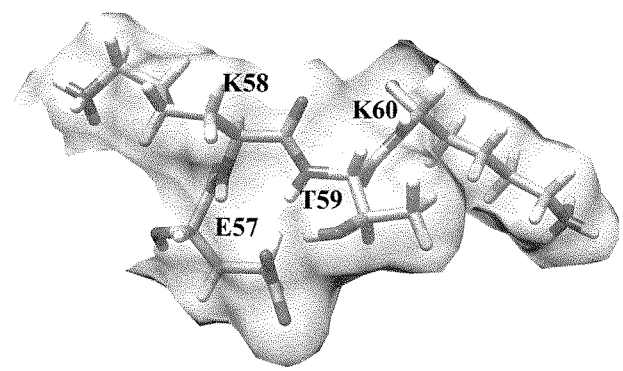
Figure 3C:
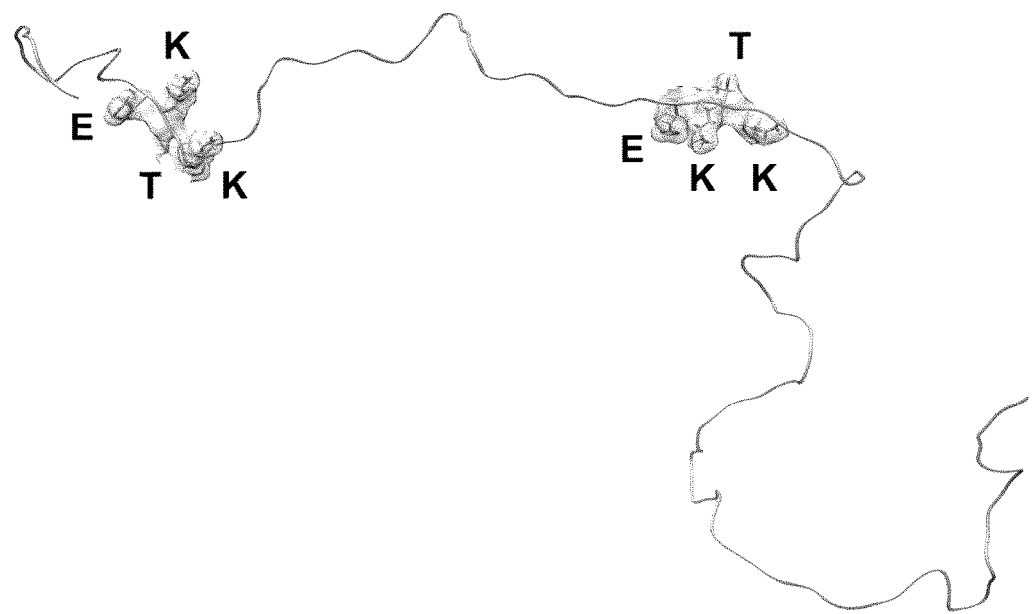
Figure 4A:
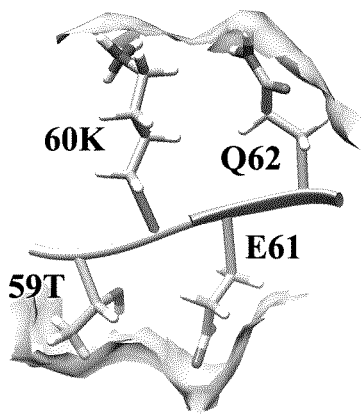
FIG. 4, Panel A shows a snapshot of the TKEQ (SEQ ID NO: 4) in the context of the unbiased fibril (PDB 2N0A). The figure also shows the SASA of this region of sequence; the SASA is minimal since the epitope is largely buried. Panel B shows the centroid structure for the ensemble of the cyclic peptide cyclo(CGTKEQGGGG) (SEQ ID NO: 7). The sidechains in the cyclic peptide show increased SASA relative to the sidechains in the fibril. Panel C shows the side-chain orientations of the epitope in the centroid structure of the isolated native monomer ensemble. The orientations of the side chains are significantly different in the isolated monomer ensemble than are the orientations of the corresponding side chains in the cyclic peptide ensemble.
Figure 4B:
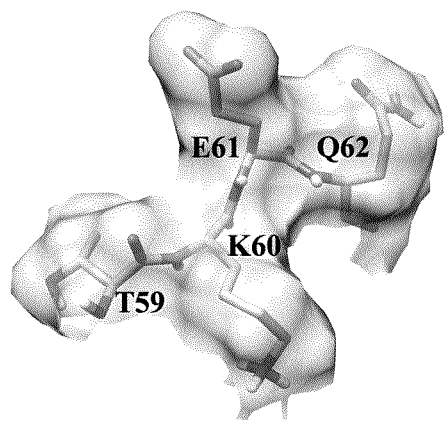
Figure 4C:
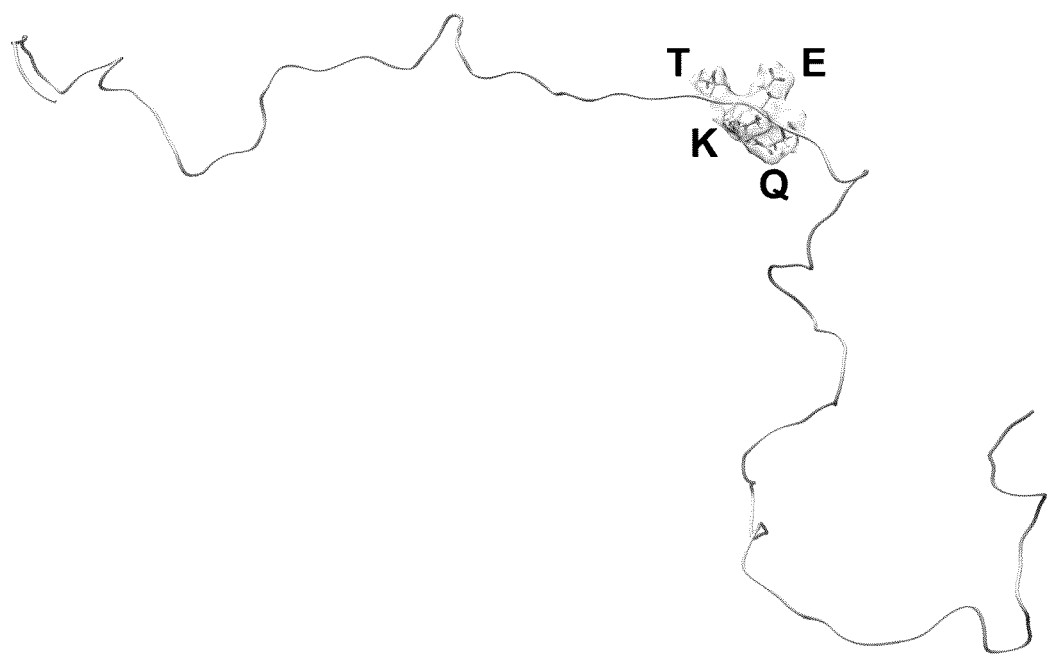
Figure 5A:
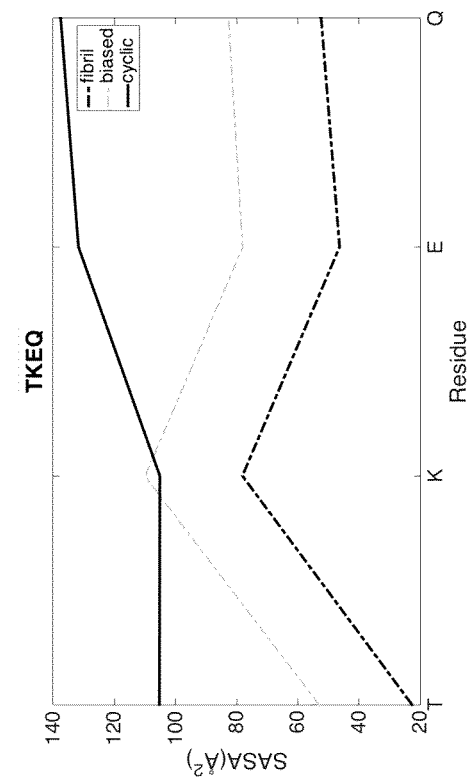
FIG. 5, Panel A plots the ensemble-averaged solvent accessible surface area (SASA) for the for the EKTK (SEQ ID NO: 2) epitope in the fibril ensemble, stressed/biased fibril ensemble, and cyclic peptide ensemble cyclo (CGGGGEKTKGG) (SEQ ID NO: 5). The residues show a monotonic increase in surface exposure between unbiased fibril, biased fibril, and cyclic peptide. Panel B plots the ensemble-averaged solvent accessible surface area (SASA) for the for the TKEQ (SEQ ID NO: 4) epitope in the unbiased fibril ensemble, stressed/biased fibril ensemble, and cyclic peptide ensemble cyclo(CGTKEQGGGG) (SEQ ID NO: 7). Residues T59, E61, and Q62 show the largest increases in surface exposure between unbiased fibril and the cyclic peptide. The increase in SASA from unbiased fibril to biased fibril is nearly uniform across the epitope. The increase in SASA for epitopes TKEQ (SEQ ID NO: 4) and EKTK (SEQ ID NO: 2) are also shown in FIG. 5, and in FIG. 1 Panels A, C. Panel C plots a histogram of the RMSD to the centroid of the cyclic peptide equilibrium distribution, for the cyclic peptide scaffold cylco (CGTKEQGGGG) (SEQ ID NO: 7). Most conformations are very similar to the centroid conformation and the distribution peaks at around 1.3 Angstrom. Also shown is the RMSD corresponding to the conformations of the epitopes in the centroid conformation of the monomer ensemble and fibril ensemble. Finally, the RMSD of the epitopes in the conformations of PDB structures of alpha helical, micelle-bound alpha-synuclein, 1XQ8 and 2KKW are shown. These conformations are dissimilar from most cyclic conformations.
Figure 5B:
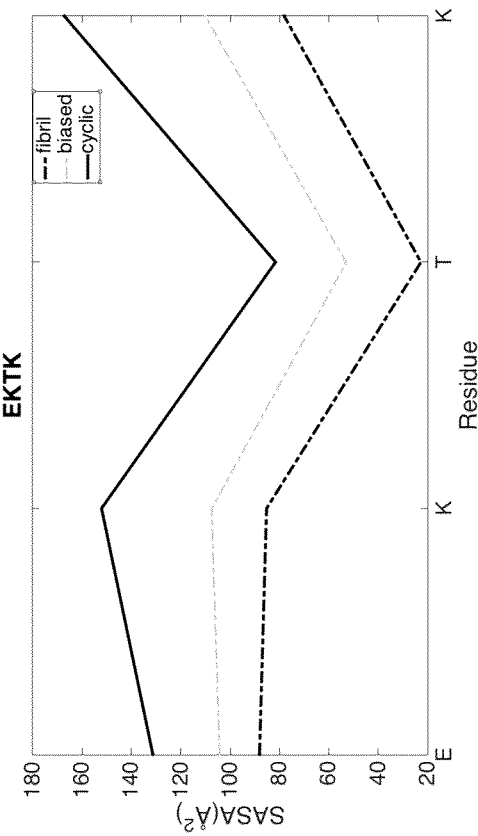

FIG. 3 Panels A-C illustrate snapshots of the epitope indicating solvent accessible surface area (SASA) of each residue in centroids of the equilibrium ensemble of the unbiased fibril ensemble; the identified cyclic peptide; and the isolated (native) monomer for the sequence EKTK. (SEQ ID NO: 2). FIG. 4 Panels A-C gives a snapshots of indicating solvent accessible surface area (SASA) of each residue in the the unstressed fibril ensemble; equilibrium ensemble of the cyclic peptide; and the isolated monomer ensemble for the sequence TKEQ (SEQ ID NO: 4). FIGS. 1A and 1C shows that the SASA of residues in EKTKEQ (SEQ ID NO: 1), including in EKTK (SEQ ID NO: 2), KTKE (SEQ ID NO: 3), and TKEQ (SEQ ID NO: 4) in the biased fibril ensemble is increased over the unbiased fibril. FIGS. 5A and B show that the SASA of the cyclic peptide is increased over that in the unbiased or biased ensemble (with the exception of K60 for TKEQ (SEQ ID NO: 4), indicating more surface would be exposed and thus accessible to antibody binding. For TKEQ (SEQ ID NO: 4) the increase in exposure is most significant for residues E61 and Q62, which shows the largest increase in SASA over the unbiased ensemble. For E61, this difference between the cyclic to unbiased fibril is 101 Å$^2$, while for Q62, this difference is 67 Å$^2$. For T59, the difference between the cyclic to unbiased fibril for TKEQ (SEQ ID NO: 4) is 80 Å$^2$ while for EKTK (SEQ ID NO: 2) the difference is 65 Å$^2$.

Figure 5C:
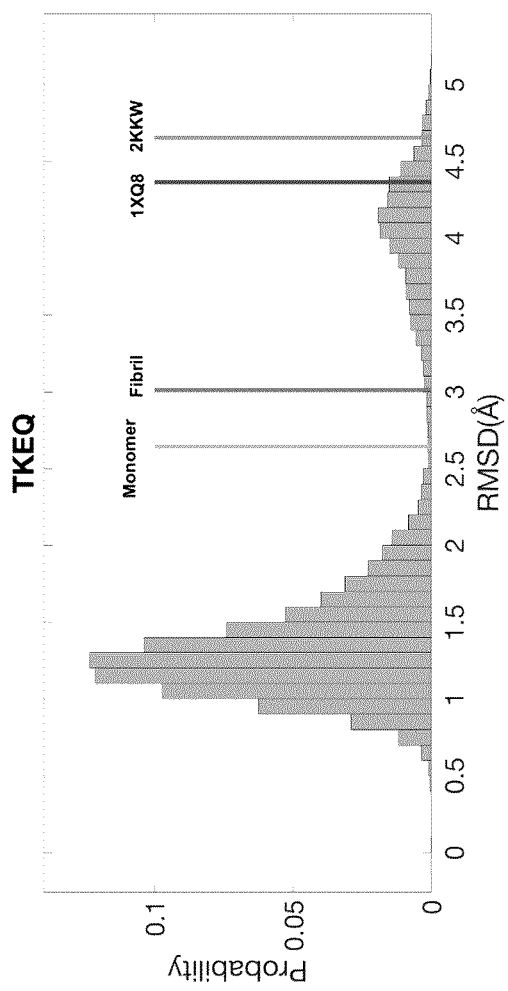

III. The Ensemble of Cyclic Peptide Conformations Clusters Differently than the Ensemble of Either Linear or Fibril Conformations FIG. 5C plots a histogram of the RMSD to the centroid of the cyclic peptide equilibrium distribution, for the cyclic peptide scaffolds cyclo(CGTKEQGGGG) (SEQ ID NO: 7). Most conformations are very similar to the centroid conformation and the distribution peaks at around 1.3 Angstrom. Also shown is the RMSD corresponding to the conformations of the epitopes in the centroid conformation of the native monomer ensemble and the fibril ensemble. Finally, the RMSD of the epitopes in the conformations of PDB structures of alpha helical, micelle-bound alpha-synuclein, 1XQ8 and 2KKW, are shown. This figure shows that these conformations are dissimilar from most cyclic conformations. The dissimilarity between the epitope conformation in cyclic peptide ensemble and its conformation in either the fibril ensemble or the isolated native monomer ensemble can be quantified by using the Jensen-Shannon distance. This distance gives an effective separation between any two pairs of ensembles, which may be recast as an effective separation between two Gaussian ensembles. Cyclic peptide conformations cyclo(CGGGGEKTKGG) (SEQ ID NO: 5) of the epitope EKTK (SEQ ID NO: 2) are distinct from those in the fibril: the effective distance between two gaussians representing these ensembles would be 7.8 standard deviations. Many cyclic peptide conformations of the epitope are also distinct from those in the isolated native monomer ensemble: the effective distance between two gaussians representing these ensembles would be 3.1 standard deviations.

Similarly, the cyclic peptide conformations Cyclo (CGTKEQGGGG) (SEQ ID NO: 7) of the epitope TKEQ (SEQ ID NO: 4) are distinct from those in the fibril: the effective distance between two gaussians representing these ensembles would be 7.8 standard deviations. Most cyclic peptide conformations of the epitope are also distinct from those in the isolated native monomer ensemble: the effective distance between two gaussians representing these ensembles would be 5.2 standard deviations.

The conformations of alpha-helical membrane-bound alpha-synuclein (PDB IDs 1XQ8 and 2KKW) are also distinct from most conformations in the cyclic peptide ensemble, as can be seen for example in FIG. 5C for the TKEQ (SEQ ID NO: 4) epitope. The degree of similarity was quantified by calculating the embedding depth of the epitope in these PDB structures into the cyclic peptide ensemble. Lower embedding depths indicate that less of the ensemble is outside of the PDB structure, and thus a larger percentage of cyclic conformations are distinct from those in the PDB structures. For EKTK (SEQ ID NO: 2), the embedding depth for the epitope in 2KKW is 20%, and the embedding depth for the epitope in 1QX8 is 38%. For TKEQ (SEQ ID NO: 4), the embedding depth for the epitope in 2KKW is 16%, and the embedding depth for the epitope in 1QX8 is 22%. These numbers indicate that much of the cyclic peptide ensemble is conformationally-distinct from the conformations of the epitope in alpha helical membrane-bound alpha-synuclein; antibodies raised to the cyclic peptide are thus unlikely to bind to this native form of the epitope.

Example 2

Scaffolding that can be used to present the identified epitopes in a cyclic conformation were assessed. Table 2 below gives several cyclic epitope scaffolds for EKTK (SEQ ID NO: 2), obtained by flanking the epitope with a variable number of glycine amino acids N- and C-terminal to the epitope. Suitability is assessed by measuring the Jenson-Shannon-distance between the ensembles of the cyclic peptide, the equilibrium ensembles of the alpha-synuclein monomer, beta-synuclein monomer, and gamma-synuclein monomer, and the equilibrium ensemble of the stressed (i.e. biased) fibril. Similarity to the stressed/biased fibril is desired, while dissimilarity to the monomer ensembles is also desired to avoid interference with in vivo function.

Cyclic peptide scaffolds that are predicted to be suitable based on these criteria are described in Table 2.

TABLE 2

Cyclic peptides for epitope EKTK (SEQ ID NO: 2)

| Cyclic peptide | SEQ ID NO: |
|---|---|
| CGGGGEKTKGG | 5 |
| CGGGEKTKGG | 10 |
| CGEKTKGGG | 18 |
| CGEKTKGG | 19 |
| CGGEKTKGGG | 20 |
| CGGGGEKTKG | 21 |
| CGEKTKG | 22 |
| CGGGGEKTKGGGG | 23 |
| CGGGEKTKGGG | 24 |
| CGGGGEKTKGGG | 25 |
| CGEKTKGGGG | 26 |
| CGGEKTKG | 27 |
| CGGGEKTKGGGG | 28 |
| CGGEKTKGG | 29 |
| CGGEKTKGGGG | 30 |
| CGGGGEKTKG | 31 |

A similar analysis was conducted for epitope KTKE (SEQ ID NO: 3). Suitable scaffolds are provided in Table 3.

TABLE 3

Cyclic peptides for epitope KTKE (SEQ ID NO: 3)

| Cyclic peptide | SEQ ID NO: |
|---|---|
| CGGGGKTKEGG | 32 |
| CGGKTKEGG | 33 |
| CGGGGKTKEG | 34 |
| CGKTKEGG | 35 |
| CGGKTKEG | 36 |
| CGGGKTKEGGGG | 37 |
| CGGGGKTKEGGG | 38 |
| CGGGKTKEGGG | 39 |
| CGKTKEG | 40 |
| CGGGGKTKEGGGG | 41 |
| CGGGKTKEG | 42 |
| CGGKTKEGGG | 43 |
| CGKTKEGGG | 44 |

TABLE 3-continued

Cyclic peptides for epitope KTKE (SEQ ID NO: 3)

| Cyclic peptide | SEQ ID NO: |
|---|---|
| CGKTKEGGG | 45 |
| CGGKTKEGGGG | 46 |

A similar analysis was conducted for epitope TKEQ (SEQ ID NO: 4). Suitable scaffolds are provided in Table 4.

TABLE 4

TKEQ (SEQ ID NO: 4) epitope scaffolds.

| cyclic peptide | SEQ ID NO: |
|---|---|
| CGTKEQGGGG | 7 |
| CGGGGTKEQGG | 11 |
| CGGTKEQGGG | 47 |
| CGGTKEQGG | 48 |
| CGGTKEQGGGG | 49 |
| CGGTKEQG | 50 |
| CGGGGTKEQGGGG | 51 |
| CGGGGTKEQGGG | 52 |
| CGTKEQGG | 53 |
| CGGGTKEQGGG | 54 |
| CGGGTKEQGG | 55 |
| CGTKEQG | 56 |
| CGTKEQGGG | 57 |
| CGGGTKEQGGGG | 58 |
| CGGGGTKEQG | 59 |
| CGGGTKEQG | 60 |

Example 3

Cyclic Compound Construction Comprising a Conformationally Constrained Epitope

Compounds comprising conformationally constrained epitope sequences can be prepared by making linear peptides comprising or consisting an epitope described herein such as EKTKEQ (SEQ ID NO: 1), EKTK (SEQ ID NO: 2), KTKE (SEQ ID NO: 3), or TKEQ (SEQ ID NO: 4) or a part thereof such as KEQ, and a linker sequence and cyclized to make cyclic compounds such as Cyclo(CGTKEQGGGG) (SEQ ID NO: 7) or cyclo(CGGTKEQGGGG) (SEQ ID NO: 49). For example, the cyclic compounds can be made by cyclizing linear peptides head to tail.

For example, a peptide corresponding to an epitope such as EKTK (SEQ ID NO: 2), KTKE (SEQ ID NO: 3), or TKEQ (SEQ ID NO: 4) or a part thereof such as KEQ can be synthesized with or conjugated to a a linker, preferably comprising 1, 2, 3, or 4 amino acids and/or PEG units C terminal and/or N terminal to the epitope sequence. When the linker is composed of amino acid sequence, it can be synthesized using known methods such as Fmoc based solid phase peptide synthesis alone or in combination with other methods. PEG molecules can be coupled to amine groups at the N terminus for example using coupling chemistries described in Hamley 2014 [*Biomacromolecules*, 2014, 15 (5), pp 1543-1559, DOI: 10.1021/bm500246w] and Roberts et al 2012 [*Advanced Drug Delivery Reviews*, Volume 64, Supplement, December 2012, Pages 116-127; M. J. Roberts M.D. Bentley J. M. Harris doi.org/10.1016/j.addr.2012.09.025], each incorporated herein by reference. The compounds may be cyclized by covalently bonding 1) the amino terminus and the carboxy terminus of the peptide+ linker to form a peptide bond (e.g. cyclizing the backbone), 2) the amino or carboxy terminus with a side chain in the peptide+linker or 3) two side chains in the peptide+linker.

The bonds in the cyclic compound may be all regular peptide bonds (homodetic cyclic peptide) or include other types of bonds such as ester, ether, amide or disulfide linkages (heterodetic cyclic peptide).

Peptides may be cyclized by oxidation of thiol- or mercaptan-containing residues at the N-terminus or C-terminus, or internal to the peptide, including for example cysteine and homocysteine. For example two cysteine residues flanking the peptide may be oxidized to form a disulphide bond. Oxidative reagents that may employed include, for example, oxygen (air), dimethyl sulphoxide, oxidized glutathione, cystine, copper (II) chloride, potassium ferricyanide, thallium(III) trifluro acetate, or other oxidative reagents such as may be known to those of skill in the art and used with such methods as are known to those of skill in the art.

Methods and compositions related to cyclic peptide synthesis are described in U.S. Patent Publication 2009/0215172. U.S. Patent publication 2010/0240865, U.S. Patent Publication 2010/0137559, and U.S. Pat. No. 7,569,541 describe various methods for cyclization. Other examples are described in PCT Publication WO01/92466, and Andreu et al., 1994. Methods in Molecular Biology 35:91-169.

The linker can comprise one or more cysteine residues flanking and/or inserted in the linker. The peptide can be structured into a cyclic conformation by creating a disulfide linkage between the non-native cysteines residues added to the N- and C-termini of the peptide.

The cyclic peptide can be linked to a carrier, optionally a BSA moiety or an immunogenicity enhancing agent such as KLH.

Example 4

The following linear and cyclic peptides were prepared:

TABLE 1

Cyclic peptides for immunogens
and corresponding linear peptide

| Linear CGTKEQGGGG | (SEQ ID NO: 7) (1, 4 linker) |
| Cylo(CGTKEQGGGG) | (SEQ ID NO: 7) (1, 4 linker) |
| Linear CGGTKEQGG | (SEQ ID NO: 48) (2, 2 linker) |
| Cyclo(CGGTKEQGG) | (SEQ ID NO: 48) (2, 2 linker) |
| Linear CGGTKEQGGGG | (SEQ ID NO: 49) (2, 4 linker) |
| Cyclo(CGGTKEQGGGG) | (SEQ ID NO: 49) (2, 4 linker) |

TABLE 1-continued

Cyclic peptides for immunogens
and corresponding linear peptide

| Linear CGGGEKTKGG | (SEQ ID NO: 10) (3, 2 linker) |
| Cyclo(CGGGEKTKGG) | (SEQ ID NO: 10) (3, 2 linker) |
| Linear CGGGGEKTKGGG | (SEQ ID NO: 25) (4, 3 linker) |
| Cyclo(CGGGGEKTKGGG) | (SEQ ID NO: 25) (4, 3 linker) |

Peptide synthesis was performed by CPC Scientific Inc. (Sunnyvale CA, USA). The peptides were synthesized by standard conventional Fmoc-based solid-phase peptide synthesis on 2-chlorotrityl chloride resin, followed by cleavage from the resin. Peptide sequence was confirmed by electrospray MS and purity was assessed by HPLC to confirm at least 95% pure. Cyclization was performed via a head-to-tail (C-G) amide bond. Non-cyclized, linear CGHHQKG peptide was also produced by CPC Scientific.

Immunogen Construction

The cyclic compounds in Table 1 were then conjugated to KLH (for immunizing) or BSA (for screening) via maleimide-based coupling (CPC Scientific Inc, Sunnyvale CA).

Example 5

Antibody Generation and Selection

The linked peptides were used for mouse monoclonal antibody production, following protocols approved by the Canadian Council on Animal Care (Immunoprecise Antibodies LTD (Victoria BC, Canada)).

Immunization

Briefly, fifty day old female BALB/c mice (Charles River Laboratories, Quebec) were immunized. A series of subcutaneous aqueous injections containing antigen but no adjuvant were given over a period of 19 days. Mice were immunized with 100 µg per mouse per injection of a 0.5 mg/mL solution in sterile saline of cyclic peptide-KLH. All mice were euthanized on Day 19 and lymphocytes were harvested for hybridoma cell line generation.

Fusion/Hybridoma Development

Lymphocytes were isolated and fused with murine SP2/0 myeloma cells in the presence of poly-ethylene glycol (PEG 1500). Fused cells were cultured using HAT selection. This method uses a semi-solid methylcellulose-based HAT selective medium to combine the hybridoma selection and cloning into one step. Single cell-derived hybridomas were grown to form monoclonal colonies on the semi-solid media. 10 days after the fusion event, resulting hybridoma clones were transferred to 96-well tissue culture plates and grown in HT containing medium until mid-log growth was reached (5 days).

Hybridoma Analysis (Screening)

Tissue culture supernatants from the hybridomas were tested by indirect ELISA on screening antigen (cyclic peptide-BSA and linear peptide-BSA) and probed for both IgG and IgM antibodies using a Goat anti-IgG/IgM(H&L)-HRP secondary and developed with TMB substrate.

Positive cultures were retested on screening antigen to confirm secretion and on an irrelevant antigen (Human Transferrin). Clones were isotyped by antibody trapping ELISA to determine if they are IgG or IgM isotype and tested by indirect ELISA on other cyclic peptide-BSA conjugates comprising the same epitope to evaluate cross-reactivity.

Isotyping

The hybridoma antibodies were isotyped using antibody trap experiments. Trap plates were coated with 1:10,000 Goat anti-mouse IgG/IgM(H&L) antibody at 100 uL/well carbonate coating buffer pH9.6 overnight at 4C. Primary antibody (hybridoma supernatants) was added at 100 ug/mL. Secondary Antibody was added at 1:5,000. Goat anti-mouse IgGγ-HRP or 1:10,000 Goat anti-mouse IgMμ-HRP was added at 100 uL/well in PBS-Tween for 1 hour at 37C with shaking. All washing steps were performed for 30 mins with PBS-Tween. The substrate TMB was added at 50 uL/well, developed in the dark and stopped with equal volume 1 M HCl.

Results

TKEQ (SEQ ID NO: 4) Constructs

Mice immunized with cyclo(CGTKEQGGGG)-KLH (SEQ ID NO: 7), cyclo(CGGTKEQGGGG)-KLH (SEQ ID NO: 49) and cyclo(CGGTKEQGG)-KLH (SEQ ID NO: 48) produced clones that were selective for the cyclic peptide (free or bound to BSA) relative to the linear construct. Clones were tested for reactivity to cyclic peptide-BSA at least 3 times for each clone with similar results.

TABLE 5

Binding characteristics of hybridoma clones for mice immunized with cyclo(CGTKEQGGGG)-KLH (SEQ ID NO: 7)

|  | 8H11 | 2E9 | 4D7 | 6C4 | 6C6 | 5H6 | 8B12 | 10F3 | 3C4 | 8B10 |
|---|---|---|---|---|---|---|---|---|---|---|
| (1,4)-C-BSA | 1.883 | 1.914 | 1.657 | 2.396 | 1.987 | 2.123 | 2.445 | 2.028 | 1.979 | 2.228 |
| (1,4)-C-Free | 1.682 | 2.197 | 2.002 | 1.974 | 2.041 | 2.008 | 1.836 | 1.216 | 1.222 | 0.388 |
| (1,4)-L-BSA | 0.054 | 0.054 | 0.052 | 0.045 | 0.102 | 0.058 | 0.049 | 0.061 | 0.067 | 0.149 |
| HT | 0.058 | 0.054 | 0.062 | 0.104 | 0.137 | 0.065 | 0.045 | 0.065 | 0.113 | 0.043 |
| (1,4)-C-BSA | 1.603 | 1.748 | 2.567 | 2.582 | 2.307 | 2.533 | 2.402 | 2.215 | 2.129 | 2.194 |
| HSA | 0.063 | 0.044 | 0.043 | 0.045 | 0.083 | 0.050 | 0.046 | 0.058 | 0.044 | 0.045 |
| Trap IgGy | 1.055 | 0.831 | 1.260 | 1.120 | 1.066 | 1.122 | 1.249 | 0.776 | 0.731 | 1.159 |
| Trap IgMu | 0.059 | 0.059 | 0.044 | 0.153 | 0.081 | 0.043 | 0.107 | 0.058 | 0.058 | 0.043 |

|  | 3B5 | 5G4 | 10H4 | 3G11 | 10D5 | 7H5 |
|---|---|---|---|---|---|---|
| (1,4)-C-BSA | 2.255 | 2.141 | 2.715 | 2.427 | 2.036 | 1.990 |
| (1,4)-C-Free | 2.080 | 2.049 | 0.047 | 1.122 | 1.254 | 1.969 |
| (1,4)-L-BSA | 0.109 | 0.048 | 0.045 | 0.064 | 0.087 | 0.067 |
| HT | 0.089 | 0.055 | 0.052 | 0.052 | 0.060 | 0.068 |
| (1,4)-C-BSA | 1.731 | 1.817 | 2.310 | 2.650 | 2.158 | 2.290 |
| HSA | 0.060 | 0.043 | 0.048 | 0.060 | 0.065 | 0.059 |
| Trap IgGy | 0.713 | 1.081 | 1.052 | 0.653 | 1.250 | 1.041 |
| Trap IgMu | 0.061 | 0.045 | 0.045 | 0.062 | 0.051 | 0.044 |
| BSA | 0.065 | 0.044 | 0.044 | 0.060 | 0.066 | 0.058 |

TABLE 6

Binding characteristics of hybridoma clones for mice immunized with cyclo(CGGTKEQGG)-KLH (SEQ ID NO: 48)

|  | 1H1 | 1A2 | 3B3 | 8D6 | 7F6 | 8B12 | 11A6 | 12G6 | 9C12 | 9A7 |
|---|---|---|---|---|---|---|---|---|---|---|
| HT | 0.053 | 0.071 | 0.048 | 0.074 | 0.073 | 0.053 | 0.169 | 0.054 | 0.06 | 0.047 |
| Hum. SA | 0.055 | 0.069 | 0.053 | 0.065 | 0.064 | 0.049 | 0.05 | 0.086 | 0.052 | 0.051 |
| Trap IgGy | 0.744 | 0.545 | 0.701 | 0.628 | 1.04 | 0.633 | 0.885 | 0.767 | 0.713 | 0.708 |
| Trap IgMu | 0.061 | 0.091 | 0.058 | 0.059 | 0.062 | 0.1 | 0.055 | 0.06 | 0.074 | 0.059 |
| BSA | 0.053 | 0.117 | 0.049 | 0.071 | 0.063 | 0.042 | 0.042 | 0.043 | 0.041 | 0.044 |
| (2,2)-C-BSA | 1.971 | 1.927 | 2.145 | 1.797 | 1.795 | 1.936 | 1.926 | 1.751 | 2.126 | 2.33 |
| L-BSA | 0.042 | 0.069 | 0.041 | 0.065 | 0.08 | 0.73 | 0.064 | 0.062 | 0.043 | 0.048 |

TABLE 7

Binding characteristics of hybridoma clones for mice immunized with cyclo(CGGTKEQGGGG)-KLH (SEQ ID NO: 49)

|  | 1A12 | 5B12 | 7C4 | 9D8 | 10A10 | 2D2 | 7B3 | 5F8 | 2H9 | 12G1 |
|---|---|---|---|---|---|---|---|---|---|---|
| (2,4)-C-BSA | 1.825 | 1.863 | 1.836 | 1.182 | 1.623 | 1.793 | 1.395 | 1.676 | 1.662 | 1.01 |
| (2,4)-C-FREE | 1.556 | 1.263 | 1.263 | 0.227 | 1.27 | 1.302 | 0.427 | 1.068 | 0.051 | 0.437 |
| (2,4)-L-BSA | 0.055 | 0.07 | 0.053 | 0.109 | 0.076 | 0.051 | 0.072 | 0.053 | 0.088 | 0.113 |
| HT | 0.057 | 0.052 | 0.054 | 0.06 | 0.048 | 0.052 | 0.048 | 0.047 | 0.059 | 0.071 |
| HAS | 0.055 | 0.048 | 0.055 | 0.054 | 0.048 | 0.048 | 0.047 | 0.047 | 0.048 | 0.052 |
| IgG | 0.577 | 0.453 | 0.593 | 0.42 | 0.497 | 0.549 | 0.181 | 0.438 | 0.444 | 0.573 |
| IgM | 0.051 | 0.053 | 0.05 | 0.049 | 0.051 | 0.052 | 0.048 | 0.049 | 0.051 | 0.053 |
| BSA | 0.077 | 0.066 | 0.059 | 0.055 | 0.058 | 0.053 | 0.089 | 0.058 | 0.069 | 0.06 |

TABLE 7-continued

Binding characteristics of hybridoma clones for mice immunized with cyclo(CGGTKEQGGGG)-KLH (SEQ ID NO: 49)

|  | 5E9 | 8A9 | 1C7 | 4A10 |
|---|---|---|---|---|
| (2,4)-C-BSA | 1.781 | 1.671 | 1.934 | 1.91 |
| (2,4)-C-FREE | 0.123 | 0.09 | 1.462 | 0.141 |
| (2,4)-L-BSA | 0.06 | 0.055 | 0.065 | 0.048 |
| HT | 0.06 | 0.057 | 0.074 | 0.055 |
| HAS | 0.056 | 0.048 | 0.096 | 0.047 |
| (2,4)-C-BSA | 1.685 | 1.745 | 1.862 | 1.638 |
| IgG | 0.467 | 0.516 | 0.483 | 0.504 |
| IgM | 0.062 | 0.052 | 0.051 | 0.044 |
| BSA | 0.189 | 0.052 | 0.117 | 0.06 |

Hybridoma antibodies were also tested for their ability to selectively bind cyclic peptides that comprised different linkers shown in Tables 2-4.

TABLE 8

Hybridoma antibodies raised against cyclo(CGTKEQGGGG) (SEQ ID NO: 7)

|  | 8H11 | 2E9 | 4D7 | 6C4 | 6C6 | 5H6 | 8B12 | 10F3 | 3C4 | 8B10 |
|---|---|---|---|---|---|---|---|---|---|---|
| (1,4)-C-BSA | 1.883 | 1.914 | 1.657 | 2.396 | 1.987 | 2.123 | 2.445 | 2.028 | 1.979 | 2.228 |
| (1,4)-C-Free | 1.682 | 2.197 | 2.002 | 1.974 | 2.041 | 2.008 | 1.836 | 1.216 | 1.222 | 0.388 |
| (1,4)-L-BSA | 0.054 | 0.054 | 0.052 | 0.045 | 0.102 | 0.058 | 0.049 | 0.061 | 0.067 | 0.149 |
| (2,2)-C-BSA | 0.051 | 0.047 | 0.047 | 0.041 | 0.060 | 0.062 | 0.125 | 0.043 | 0.044 | 1.755 |
| (2,2)-L-BSA | 0.057 | 0.051 | 0.042 | 0.040 | 0.050 | 0.041 | 0.051 | 0.047 | 0.043 | 0.057 |
| (2,4)-C-BSA | 0.053 | 0.055 | 0.058 | 0.041 | 0.085 | 1.997 | 1.461 | 2.365 | 1.670 | 1.732 |
| (2,4)-L-BSA | 0.055 | 0.048 | 0.045 | 0.043 | 0.058 | 0.043 | 0.053 | 0.044 | 0.044 | 0.066 |

|  | 3B5 | 5G4 | 10H4 | 3G11 | 10D5 | 7H5 |
|---|---|---|---|---|---|---|
| (1,4)-C-BSA | 2.255 | 2.141 | 1.119 | 2.427 | 2.036 | 1.990 |
| (1,4)-C-Free | 2.080 | 2.049 | 0.047 | 1.122 | 1.254 | 1.969 |
| (1,4)-L-BSA | 0.109 | 0.048 | 0.045 | 0.064 | 0.087 | 0.067 |
| (2,2)-C-BSA | 0.082 | 0.046 | 0.173 | 0.044 | 0.064 | 0.292 |
| (2,2)-L-BSA | 0.059 | 0.041 | 0.040 | 0.042 | 0.045 | 0.072 |
| (2,4)-C-BSA | 0.183 | 0.058 | 0.049 | 2.036 | 1.953 | 0.732 |
| (2,4)-L-BSA | 0.071 | 0.046 | 0.042 | 0.045 | 0.050 | 0.073 |

Figure 11:
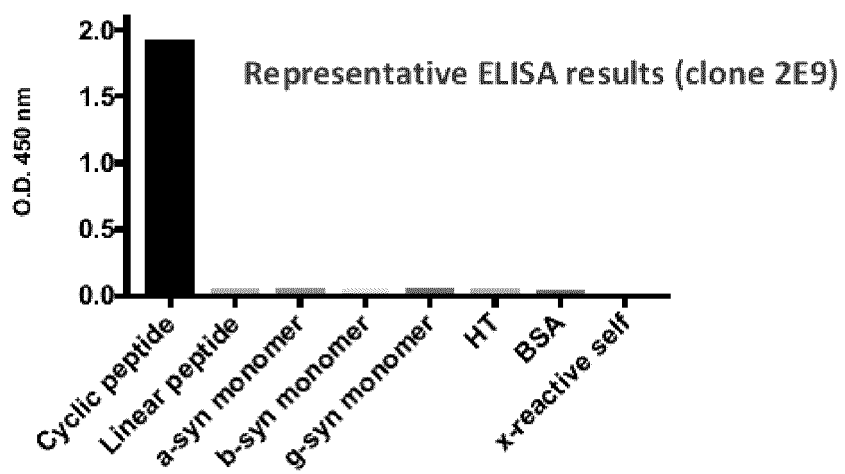
FIG. 11 is a graph showing the representative ELISA results for antibody 2E9.

Results for hybridoma antibody 2E9 to selectively bind cyclic peptide relative to linear or unrelated peptides HT, BSA and x-reactive self (a potentially cross-reactive human protein from in silico analysis) are shown in FIG. 11. Also shown is its lack of reactivity to alpha-syn, beta-syn and gamma-syn monomers.

TABLE 9

Hybridoma antibodies raised against cyclo(CGGTKEQGG) (SEQ ID NO: 48)

|  | 1H1 | 1A2 | 3B3 | 8D6 | 7F6 | 8B12 | 11A6 | 12G6 | 9C12 | 9A7 |
|---|---|---|---|---|---|---|---|---|---|---|
| (2, 2) C-BSA | 1.971 | 1.927 | 2.145 | 1.797 | 1.795 | 1.936 | 1.926 | 1.751 | 2.126 | 2.33 |
| (2, 2) L-BSA | 0.042 | 0.069 | 0.041 | 0.065 | 0.08 | 0.073 | 0.064 | 0.062 | 0.043 | 0.048 |
| 1,4-C-BSA | 0.063 | 0.075 | 0.056 | 0.059 | 0.066 | 0.070 | 0.069 | 0.063 | 0.345 | 1.695 |
| 1,4-L-BSA | 0.057 | 0.080 | 0.053 | 0.047 | 0.052 | 0.070 | 0.043 | 0.044 | 0.041 | 0.044 |
| 2,4-C-BSA | 0.173 | 0.106 | 0.061 | 0.046 | 0.735 | 2.287 | 0.946 | 0.955 | 0.070 | 0.890 |
| 2,4-L-BSA | 0.060 | 0.087 | 0.065 | 0.047 | 0.056 | 0.063 | 0.048 | 0.054 | 0.055 | 0.043 |
| Beta-Syn | 0.057 | 0.075 | 0.055 | 0.062 | 0.051 | 0.058 | 0.053 | 0.048 | 0.053 | 0.057 |
| Gamma-Syn | 0.050 | 0.077 | 0.061 | 0.044 | 0.051 | 0.063 | 0.041 | 0.041 | 0.042 | 0.044 |

TABLE 10

Hybridoma antibodies raised against cyclo(CGGTKEQGGGG) (SEQ ID NO: 49)

|  | 1A12 | 5B12 | 7C4 | 9D8 | 10A10 | 2D2 | 7B3 | 5F8 | 2H9 | 12G1 |
|---|---|---|---|---|---|---|---|---|---|---|
| (2,4)-L-BSA | 0.041 | 0.051 | 0.068 | 0.046 | 0.046 | 0.070 | 0.053 | 0.046 | 0.088 | 0.066 |
| (2,4)-C-BSA | 1.177 | 1.189 | 1.031 | 0.726 | 1.013 | 1.16 | 1.045 | 1.149 | 0.888 | 0.756 |
| (1,4)-C-BSA | 0.156 | 0.143 | 0.169 | 0.048 | 0.157 | 1.957 | 1.735 | 0.201 | 0.049 | 2.066 |
| (1,4)-L-BSA | 0.042 | 0.073 | 0.043 | 0.043 | 0.040 | 0.047 | 0.042 | 0.041 | 0.042 | 0.070 |
| (2,2)-C-BSA | 0.062 | 0.073 | 0.068 | 0.048 | 0.069 | 0.079 | 0.054 | 0.073 | 0.395 | 1.612 |
| (2,2)-L-BSA | 0.044 | 0.057 | 0.043 | 0.045 | 0.042 | 0.046 | 0.043 | 0.043 | 0.059 | 0.047 |

|  | 5E9 | 8A9 | 1C7 | 4A10 |
|---|---|---|---|---|
| (2,4)-L-BSA | 0.046 | 0.045 | 0.056 | 0.046 |
| (2,4)-C-BSA | 1.168 | 1.134 | 1.17 | 1.177 |
| (1,4)-C-BSA | 0.047 | 0.049 | 0.175 | 0.215 |
| (1,4)-L-BSA | 0.042 | 0.047 | 0.045 | 0.043 |
| (2,2)-C-BSA | 0.046 | 0.049 | 0.075 | 0.046 |
| (2,2)-L-BSA | 0.045 | 0.043 | 0.225 | 0.046 |

Example 6

EKTK Epitope (SEQ ID NO: 2)

Similarly, the binding selectivity of hybridoma antibodies raised against cyclo(CGGGEKTKGG) (SEQ ID NO: 10) to free and BSA bound cyclic peptide relative to linear or unrelated peptides HT, BSA and human complement factor H (HCFH) is shown in Table 11. Also shown is reactivity to cyclic and linear peptides of CGGGGEKTKGG (SEQ ID NO: 5).

TABLE 11

Binding Characteristics of antibodies raised against cyclo(CGGGEKTKGG) (SEQ ID NO: 10)

|  | 2B11 | 11B3 | 11F11 | 12E2 | 3C11 | 12B12 |
|---|---|---|---|---|---|---|
| BSA | 0.067 | 0.067 | 0.05 | 0.057 | 0.052 | 0.055 |
| HCFH | 0.075 | 0.082 | 0.055 | 0.068 | 0.064 | 0.059 |
| HT | 0.053 | 0.069 | 0.061 | 0.056 | 0.054 | 0.045 |
| Trap IgG | 0.867 | 0.876 | 0.657 | 1.106 | 0.419 | 0.957 |
| Trap IgM | 0.067 | 0.048 | 0.052 | 0.049 | 0.115 | 0.048 |
| ASPEP(3,2)-C-BSA | 1.446 | 1.349 | 0.804 | 1.399 | 1.171 | 1.285 |
| ASPEP(3,2)-L-BSA | 0.046 | 0.046 | 0.045 | 0.046 | 0.057 | 0.047 |
| ASPEP(4,2)-C-BSA | 0.053 | 0.045 | 0.043 | 0.051 | 0.567 | 0.851 |
| ASPEP(4,2)-L-BSA | 0.044 | 0.048 | 0.041 | 0.048 | 0.049 | 0.045 |

ASPEP refers to alpha-Syn peptide.

Further, the binding selectivity of hybridoma antibodies raised against cyclo(CGGGGEKTKGG) (SEQ ID NO: 5) to free and BSA bound cyclic peptide relative to linear or unrelated peptides HT, BSA and HCFH is shown in Table 12. Also shown is reactivity to cyclic and linear peptides of CGGGEKTKGG (SEQ ID NO: 10).

TABLE 12

Binding Characteristics of antibodies raised against cyclo(CGGGGEKTKGG) (SEQ ID NO: 5)

|  | 7F6 | 11B6 | 2D6 | 3F2 |
|---|---|---|---|---|
| 4,2-Free-C | 1.65 | 1.269 | 1.491 | 1.702 |
| HT | 0.07 | 0.051 | 0.043 | 0.036 |
| BSA | 0.05 | 0.041 | 0.045 | 0.041 |
| HCFH | 0.048 | 0.042 | 0.048 | 0.046 |
| Trap IgG | 0.783 | 0.866 | 0.839 | 0.678 |
| Trap IgM | 0.051 | 0.05 | 0.065 | 0.07 |
| ASPEP(4,2)-C-BSA | 1.758 | 1.586 | 1.604 | 1.802 |
| ASPEP(4,2)-L-BSA | 0.051 | 0.045 | 0.062 | 0.066 |
| ASPEP(3,2)-C-BSA | 0.055 | 0.047 | 0.592 | 0.215 |
| ASPEP(3,2)-L-BSA | 0.056 | 0.044 | 0.059 | 0.045 |

Mouse anti-alpha-synuclein hybridomas were cross-tested for reactivity to beta-synuclein and gamma-synuclein by indirect ELISA.

ELISA plates were coated with 0.1 microgram/well beta-synuclein or gamma-synuclein antigen at 100 microL/well in carbonate coating buffer (ph 9.6) O/N at 4° C. Plates were blocked with 3% skim milk powder in PBS for 1 hour at RT. Hybridoma antibody (100 microL/well) was added and plates incubated for 1 hour at 37° C. w/shaking. Secondary antibody at 1:5000 (goat anti-mouse IgGy-HRP) was added at 100 microL/well in PBS-Tween for 1 hour at 37° C. w/shaking. All washing steps were performed for 30 mins with PBS-Tween. TMB substrate was added at 50 microL/well, developed in the dark and stopped with an equal volume of 1 M HCL.

Results

Hybridomas raised using cyclo(CGTKEQGGGG) (SEQ ID NO: 7) were tested. Counts for both beta-synuclein and gamma-synuclein were similar to background.

Similarly hybridomas raised against cyclo (CGGTKEQGG) (SEQ ID NO: 48) and cyclo (CGGTKEQGGGG) (SEQ ID NO: 49) were tested. Counts for both beta-synuclein and gamma-synuclein were similar to background.

Ten hybridomas raised against cyclo(CGGGEKTKGG) (SEQ ID NO: 10) were tested. Counts for both beta-synuclein and gamma-synuclein were similar to background.

Similarly hybridomas raised against cyclo (CGGGGEKTKGG) (SEQ ID NO: 5) were tested. Counts for both beta-synuclein and gamma-synuclein were similar to background.

Example 7

Anti-Misfolded α-Syn Antibodies Characterization

Antibodies were tested for their ability to bind native monomeric α-Syn polypeptide as well as misfolded oligomeric α-Syn polypeptide using surface plasmon resonance.

Surface Plasmon Resonance Analysis of Biological Samples

Homogenization: Human neurological tissue samples were weighed and subsequently submersed in a volume of fresh, ice cold TBS (supplemented with 5 mM EGTA, 5 mM EDTA, (both from Sigma) and EDTA-free protease inhibitor cocktail from Roche Diagnostics, Laval QC, Canada) such that the final concentration of tissue was 20% (w/v). Tissue is homogenized in this buffer using a mechanical probe homogenizer (3×30 sec pulses with 30 sec pauses in between, all performed on ice). TBS homogenized samples were then subjected to ultracentrifugation (70,000×g for 90 min). Supernatants were collected, aliquoted and stored at −80° C. The protein concentration of TBS homogenates was determined using a BCA protein assay (Pierce Biotechnology Inc, Rockford IL, USA).

Surface Plasmon Resonance Analysis: neurological tissue samples from PD and LBD patients were analyzed. Test antibodies, positive control antibody (4D6) and IgG isotype control were immobilized at high densities (~10,000 RU) (approximately 9500 to 13,000 RUs) on flow cells of a sensor chip. Diluted samples were injected sequentially over the surfaces for approximately 300-900 seconds, followed by 150 seconds of dissociation in buffer and surface regeneration. In some experiments, 4D6 (BioLegend), was used to detect captured material. Binding responses were double-referenced by subtraction of IgG reference surface binding and normalized with assay buffer, and the different groups of samples compared.

Test antibodies included clones: 2E9, 3B5, 2D2, 8B12, 9A7. Control antibodies used were pan-Alpha Syn Antibody (4D6) (Biolegend) and Mouse IgG1 Isotype Control.

Analytes included SynAging alpha-Syn Oligomers, unfractionated Lewy Body Disease (LBD) (also referred to as dementia with Lewy Bodies (DLB)) soluble brain extracts, high molecular weight (HMW) and low molecular weight (LMW) LBD and PD fractions were analyzed.

Unfractionated soluble brain extract was diluted 1:4 and HMW and LMW fractions were diluted to 100 ug/ml total protein.

Analytes injected over immobilized antibodies for 15 minutes at 10 ul/min. Antibody 4D6 injected over captured analyte for 5 minutes at 10 ul/min

Results

Figure 6A:
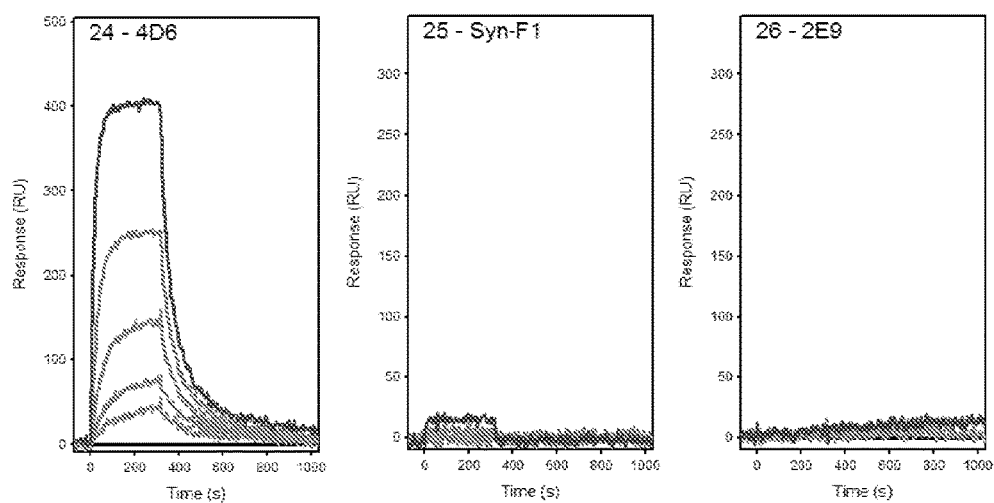
Figure 6B:
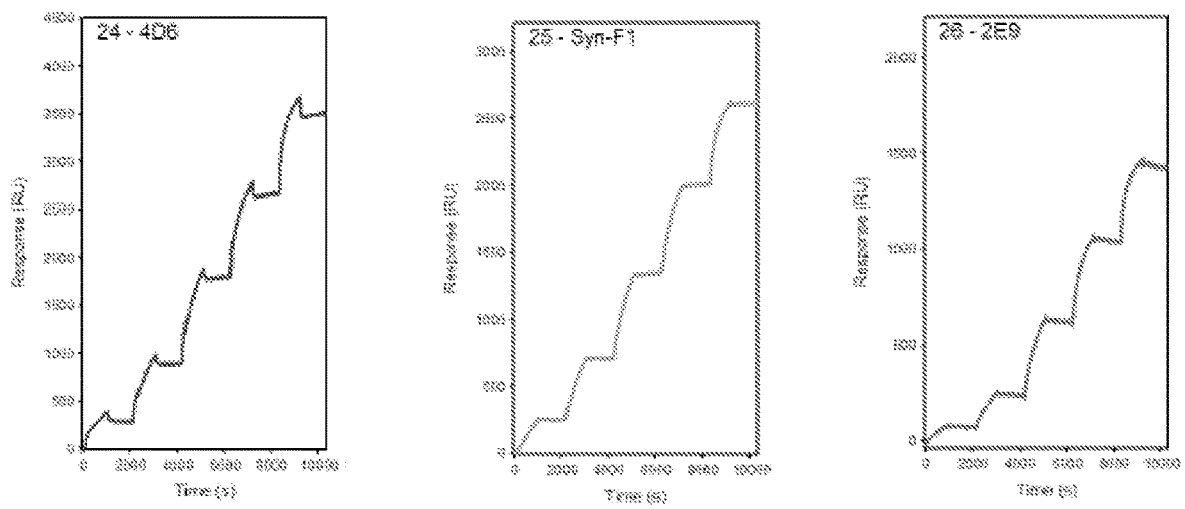

4D6 (pan alpha-syn antibody) showed strong binding to SynAging α-syn oligomers. Test clone 2E9 shows robust binding to SynAging α-syn oligomers. Test clones 2D2 and 8B12 show weaker binding (FIG. 6D). The left panel shows direct binding of captured alpha synuclein. The right panel shows alpha synuclein captured by the antibody along the x axis and detected with pan antibody 4D6

Figure 6C:
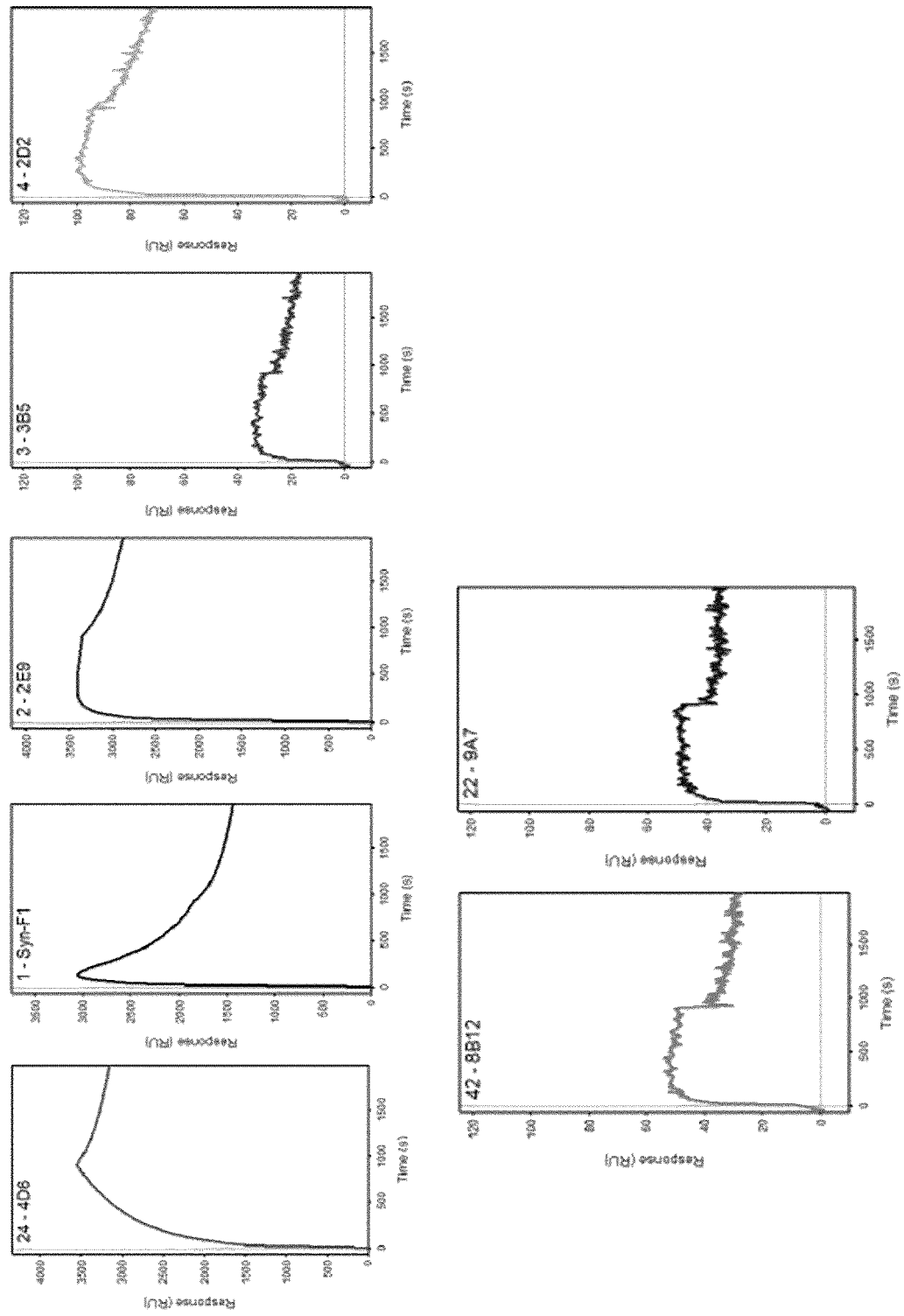
Figure 6D:
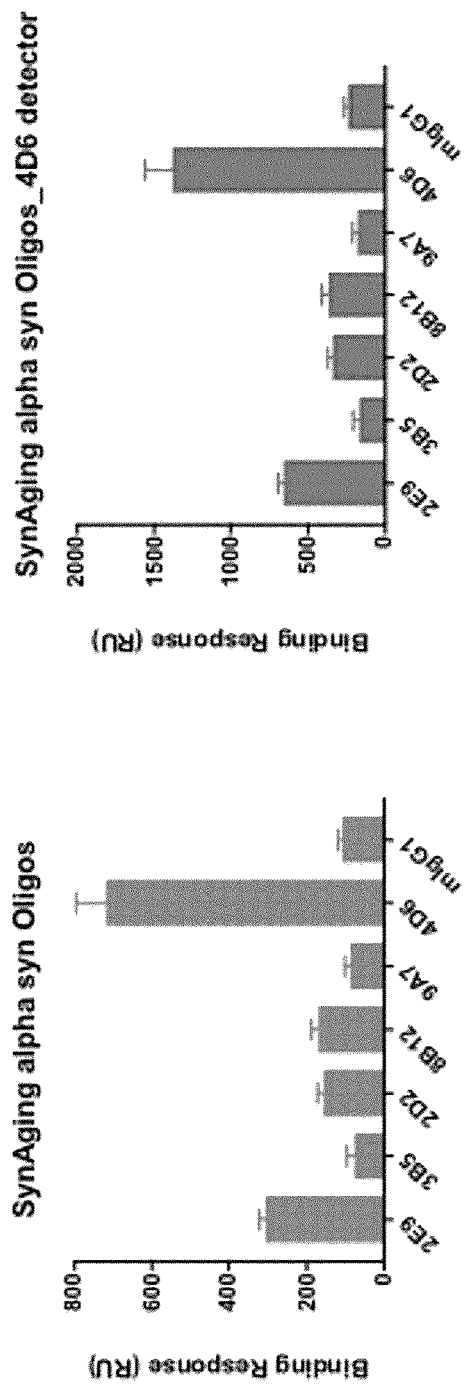
Figure 6E:
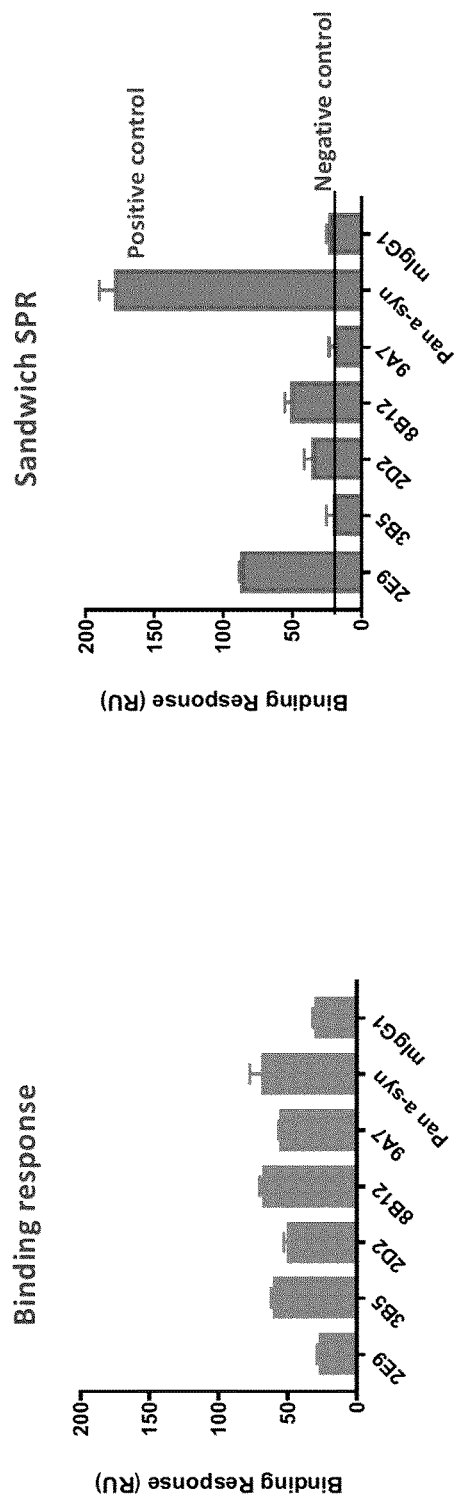

As shown in the right panel of FIG. 6E, test antibodies bound alpha-syn directly in unfractionated soluble LBD brain extract. Subsequent detection with a pan alpha-syn antibody 4D6 confirmed the presence of alpha-syn in the material captured by the test antibodies (left panel). Test clone 2E9 and, to a lesser extent, clones 2D2 and 8B12 bind α-syn in both unfractionated (FIG. 6E) as well as LMW and HMW fractions of brain extracts (FIG. 6F).

Test clones were also assessed for binding soluble fibrils. In a separate SPR run test antibodies were immobilized and a soluble sonicated fibril preparation was injected. A majority of the test antibodies showed some degree of cross-reactivity with small soluble fibrils, as shown in FIG. 6G.

FIG. 6H compares the binding profile of test clone 2E9 vs the pan alpha-syn 4D6 antibody. Clone 2E9 does not bind to monomers, exhibits a robust binding to soluble oligomers and cross-reactivity with small soluble fibrils.

Example 8

Binding to Misfolded Alpha-Synuclein Oligomers

Additional SPR experiments were carried out on a Wastach protein spotted and IBIS 96×SPR biosensor. Test mAbs along with control mAbs Syn-F1 and 4D6 were amine coupled to a 200 M biosensor surface using standard NHS/EDC activation. Controls Syn-F1 and 4D6 were immobilized each in 4 positions. The test mAbs were immobilized each in two positions. Oligomeric alpha-synuclein was purchased from SynAging (Nancy France).

Alpha synuclein monomer purchased from rPeptide (Georgia, USA) was tested up to 500 uM in a 3 fold concentration series. Syn-F1 shows weak binding to alpha monomer. 4D6 (commercial pan mAb) showed higher levels of binding to alpha synuclein (see FIG. 6A). Test antibodies showed no binding to alpha synuclein monomer (FIG. 6A).

SynAging alpha-synuclein oligomers were tested in a 3 fold titration up to 6 uM. Synaging oligomer bound well to the Syn-F1 and 4D6 surfaces. It also bound well to clone 2E9 (FIG. 6B).

Test mAb 2E9 and control 4D6 were also tested at 1/10 dilution over the surfaces with captured oligomers. 2E9 was injected first followed by 4D6 second (see arrows). 2E9 (raised against cyclo(CGTKEQGGGG) (SEQ ID NO: 7)) binds to the surfaces that have SynAging oligomers on them and not surfaces that do not. 4D6 also binds surfaces that have SynAging oligomers on them and not surfaces that do not. See FIG. 6. Binding was also detected with clone 3B5 (raised against cyclo(CGTKEQGGGG) (SEQ ID NO: 7)), 8B12, 9A7 (raised against cyclo(CGGTKEQGG) (SEQ ID NO: 48)) and 2D2 (raised against cyclo(CGGTKEQGGGG) (SEQ ID NO: 49)).

FIG. 6C demonstrates that other clones also specifically bound SynAging oligomers.

Figure 9A:
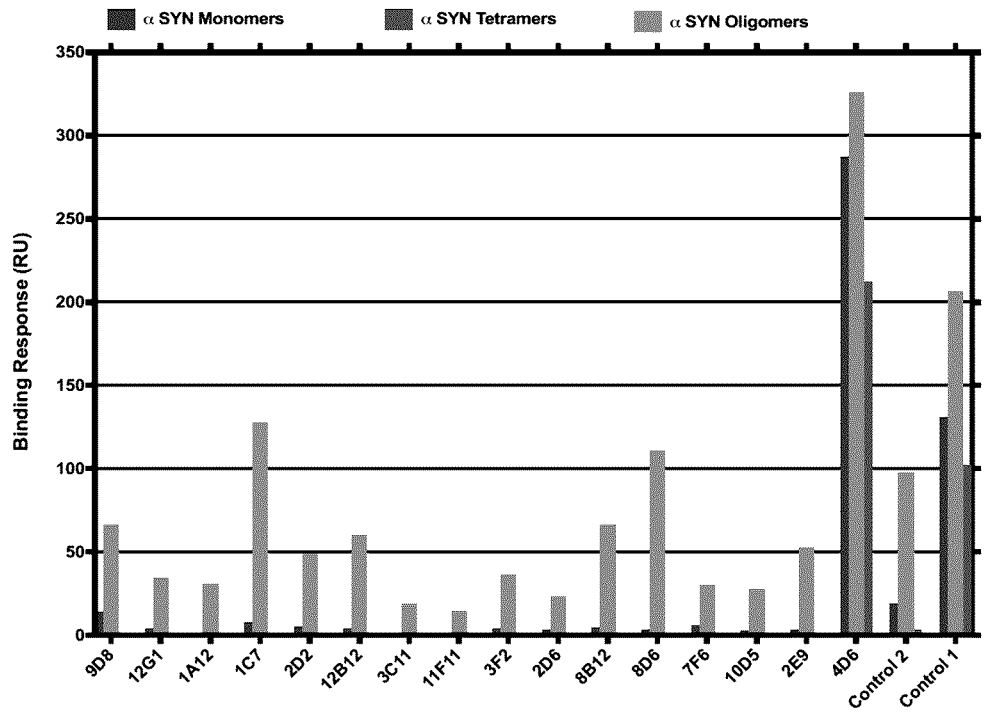
FIGS. 9A-B are a series of graphs.

In a separate SPR run with a MASS2 instrument (Sierra Biosensors), antibodies were directly immobilized onto sensor chip via amine coupling and alpha-syn analyte was injected over the chip to measure binding response. All tested clones, particularly 1C7, 8D6, 8B12, 9D8, 12B12, 2D2 and 2E9, selectively bind alpha-syn oligomers with little or no binding to monomers or physiological tetramers (FIG. 9). Control 4D6 reacted with all species of alpha-syn. Control 1 (Prasinezumab, Human IgG, PRX002/RG7935, Creative Biolabs) behaved in a similar fashion to a pan alpha-syn antibody and binds all species. Control 2 (BAN0805, mAb49/G, Mouse IgG, alpha-syn antibody, Creative Bioabs) binds alpha-syn oligomers with some reactivity against monomers.

Figure 9B:
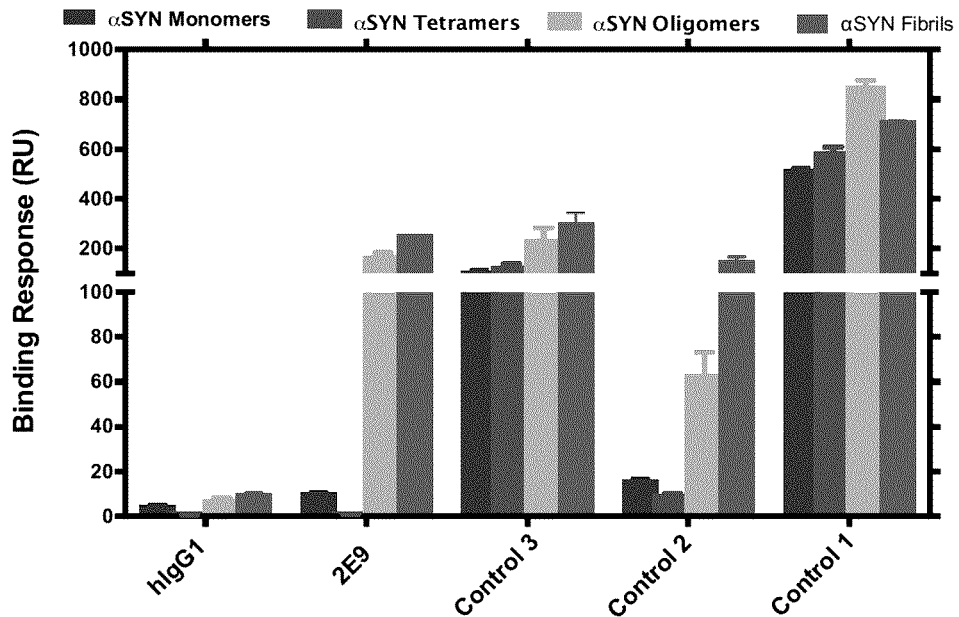

Test antibody 2E9 results are shown in comparison with other alpha-syn-directed antibodies, in FIG. 9B. Control antibodies 1 and 3 (NI-202.12F4 and PRX002 from Creative Biolabs) behaved in a similar fashion to a pan alpha-syn antibody and bind all species. Control antibody 2 (mAb 49/G) primarily binds alpha-syn oligomers and sonicated fibrils.

Example 9

Several antibodies were also tested in dot blot assays using dementia with Lewy Bodies (LBD) brain homogenate and control brain homogenate. A LBD frontal cortex high speed pellet TritonX extract (NDB13220_HP-TX) and a control brain ("72_HP-TX) were tested using Syn-F1 aggregation/fibril preferring antibody (0.5 µg/ml), 4D6 pan alpha-Syn antibody (BioLegend, 1 µg/ml) and test antibodies 2E9, 12B12, 3C11 and 2D6 (4 µg/ml). Loading was confirmed by staining for β-actin (abm, 1 µg/ml). Nitrocellulose membrane was dotted with either 10 µg of control brain or 10 µg of LBD brain. For the loading reference, 10 µg β-actin was dotted.

Figure 7C:
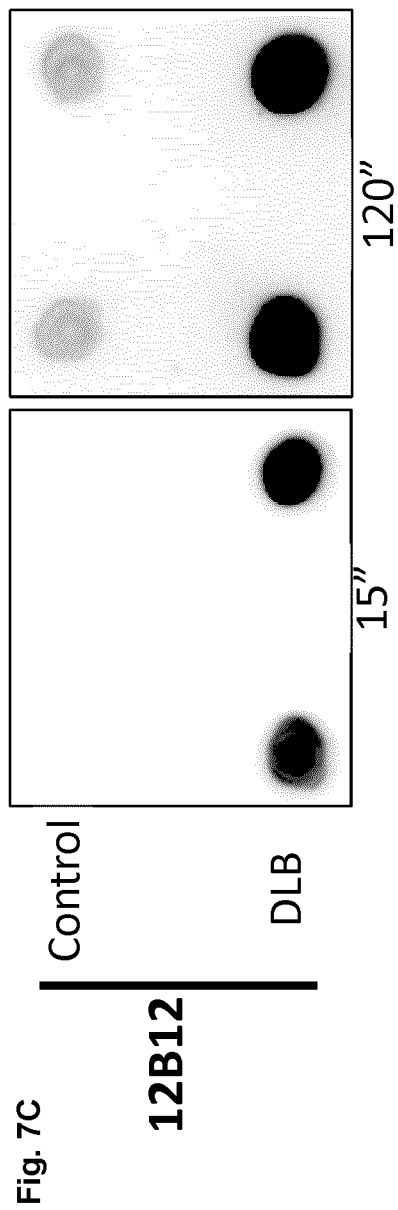
Figure 7D:
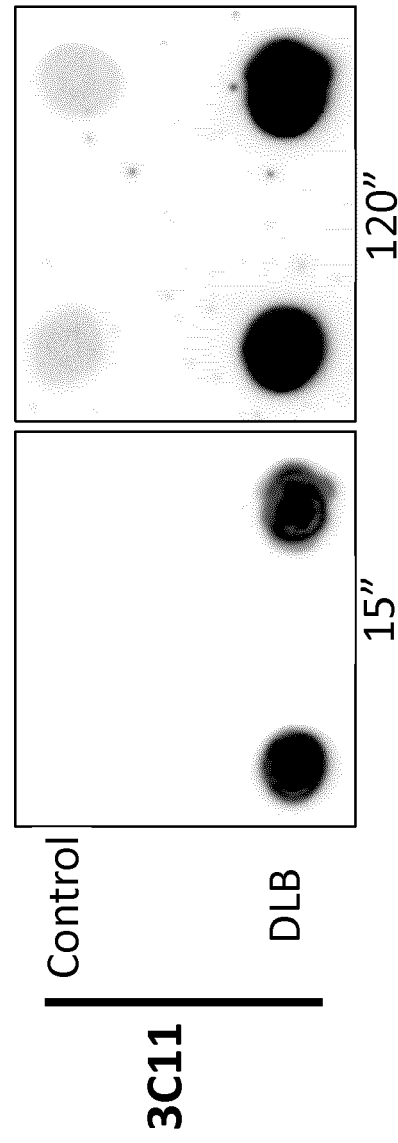
Figure 7E:
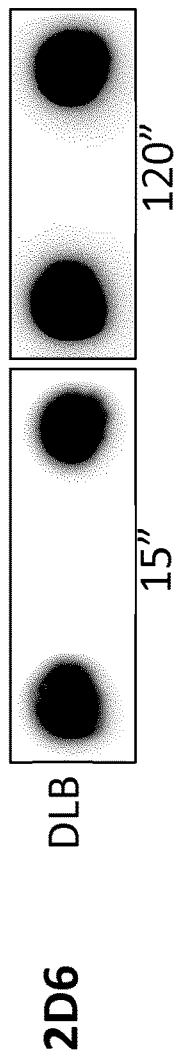
Figure 7F:
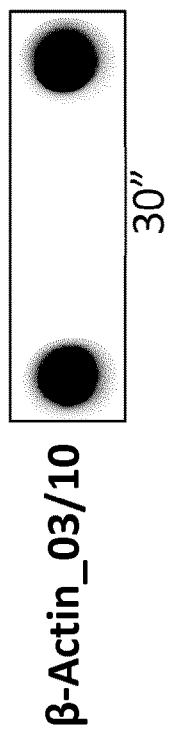

As shown in FIG. 7A Syn-F1 bound LBD preferentially compared to control brain. As shown also in FIG. 7A, 4D6 robustly binds to both LBD brain and control brain. Strong binding to LBD was exhibited by test antibodies 2E9, 12B12, 3C11 and 2D6 (FIGS. 7B-E). The beta-actin control confirmed that the amount of protein in each dot was equivalent (FIG. 7F).

Figure 7H:
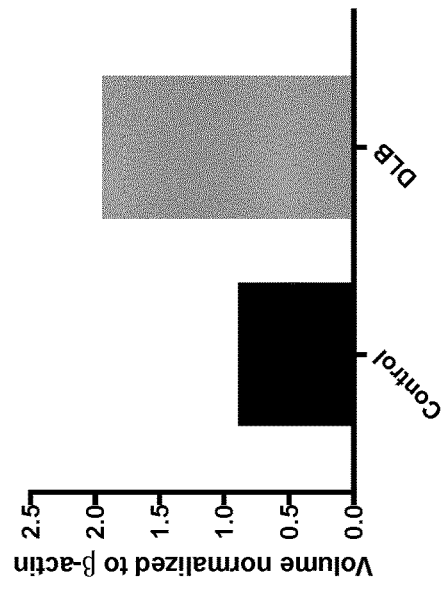
FIG. 7H is a graph showing the total amount of alpha synuclein in brain samples.
Figure 7G:
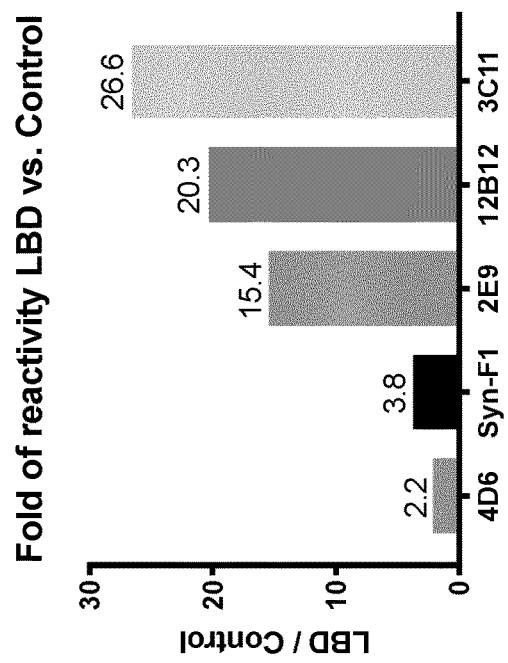
FIGS. 7G and H are a series of graphs.

The relative amount of staining for LBD relative to control brain extract was assessed for antibodies Syn-F1, 4D6, 2E9, 12B12 and 3C11. As shown in FIG. 7G, the test antibodies preferentially bound LBD by 15 to 26 fold. This was several fold higher than that seen with Syn-F1 or 4D6. The total amount of alpha-Syn detected by the pan alpha-syn antibody 4D6 in control and LBD brain is shown in FIG. 7H.

Example 10

Neuroprotective Effect of Antibodies Against α-Syn Toxicity in Rat Primary Dopaminergic Neurons Model of Parkinson's Disease The neuroprotective effect of several antibodies was also tested on rat primary dopaminergic neurons injured by exposure to alpha-syn oligomers using an in vitro Parkinson's disease model.

Methods

Rat dopaminergic neurons were cultured as described by Schinelli et al., 1988. Briefly pregnant female rats of 15 days gestation were killed by cervical dislocation (Rats Wistar; Janvier) and the foetuses removed from the uterus. The embryonic midbrains were removed and placed in ice-cold medium of Leibovitz 15 (L15; PanBiotech, Ref P04-27055, Batch: 4511117) containing 2% of Penicillin-Streptomycin (PS; PanBiotech, ref: P06-07100, Batch: 7050218) and 1% of bovine serum albumin (BSA; PanBiotech, Ref: P06-1391100, Batch: H170807). The midbrains were dissociated by trypsinisation. Cells were then mechanically dissociated by 3 passages through a 10 ml pipette. Cells were resuspended in a defined culture medium consisting of Neurobasal (Invitrogen, Ref: 11570556, Batch: 1944312) supplemented with B27 2%; (Invitrogen, ref: 17504, batch: 1950376), L-glutamine (2 mM; PanBiotech, Ref: P04-80100, Batch: 8440517) and 2% of PS, 10 ng/mmL of brain derived neurotrophic factor (BDNF) (PeproTech, Ref: 450-02, Batch: 081761) and 1 ng/mL of glial cell-derived neurotrophic factor GDNF (PanBiotech, Ref: CB-1116001, Batch: H170806). Viable cells were counted in a Neubauer cytometer using the trypan blue exclusion test. The cells were seeded at a density of 40000 cells/well in 96 well-plates (pre-coated with poly-D-lysine; Greiner, Ref: 655940, batch: E170938V) and were cultured at 37° C. in a humidified air (95%)/CO2 (5%) atmosphere Half of the medium was changed every 2 days with fresh medium. In these conditions, after 5 days of culture, astrocytes are present in the culture and release growth factor allowing neuron differentiation.

Alpha-Synuclein Preparation and Cell Culture Injury

Briefly, α-syn peptide (rPeptide, ref: S 1001-1, batch: 080817AS) was reconstituted in defined culture medium at 4 µM and slowly shaken at +37° C. for 3 days in dark to generate oligomers. The control medium was prepared in the same conditions. A second α-syn oligomer preparation from SynAging was also tested. After 6 days of culture, the test antibodies and the alpha-syn toxin (oligomers) were pre-incubated together for 30 min at room temperature before adding the mixture to the neuronal cultures. The culture medium was removed and α-syn oligomer preparation was added. Test compounds were left in during α-syn intoxication. The following conditions were tested:
Control (vehicle)/vehicle for 4 days
α-synuclein oligomer/vehicle 4 days injuries
α-synuclein oligomer (0.5 µM)+test antibodies at 2 concentrations (0.05 µM and 0.25 µM)
α-synuclein oligomer (0.5 µM)+BDNF 50 ng/mL
test antibodies alone at the highest concentration (0.25 µM) assessed
One culture was performed (6 wells per condition) to assess the dopaminergic neuronal survival.

Total Number of TH Positive Neurons

After 4 days of intoxication in presence or absence of test compounds, cells were fixed by a solution of 4% paraformaldehyde (Sigma, ref 6148, batch: SZBE2390V) for 20 min at room temperature, cells from the control conditions were fixed as well following the same procedure. The cells were then permeabilized and non-specific sites were blocked with a solution of phosphate buffered saline (PBS; PanBiotech; ref: P04-36500, Batch: 2300518) containing 0.1% of saponin (Sigma; ref: S7900, Batch: BCBJ8417V) and 1% fetal calf serum (FCS) for 15 min at room temperature. Cells were incubated with Monoclonal Anti-Tyrosine Hydroxylase antibody produced in chicken (TH, antibodies-abcam; ref: ab76442, Batch: GR3190915) PBS containing 1% FCS, 0.1% saponin, for 2 h at room temperature. Antibody against TH stained dopaminergic neuron.

The antibody was revealed with Alexa Fluor 488 goat anti-chicken IgG (Molecular probe, ref: 13417227, Batch: SC2359411A) in PBS with 1% FCS, 0.1% saponin, for 1 h at room temperature. Nuclei of cells were labelled by a fluorescent marker (Hoechst solution, Sigma; ref: B1155, Batch: 046M4048V) in the same solution.

For each condition, 20 pictures per well were taken using InCell Analyzer™ 2200 (GE Healthcare) with 20× magnification. Images of each culture well were taken in same condition. Analysis of cell bodies of TH positive neurons was performed using Developer software (GE healthcare). A total of 6 data per experimental condition were provided.

Statistics

The data were expressed as mean+/−s.e.mean (of 6 data per condition, 1 culture). A global analysis of the data was performed using a one-way analysis of variance (ANOVA) following by Dunnett's test. The level of significance is set at $p<0.05$.

Results

Figure 8A:
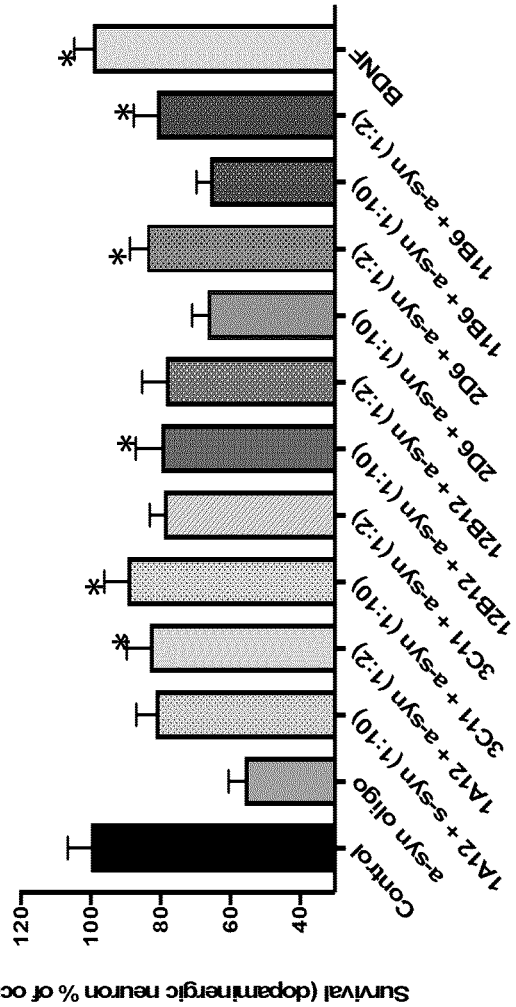

As shown in FIG. 8A, SynAging alpha synuclein oligomer preparation induced a large decrease of dopaminergic neurons survival (p<0.001, *, 58.43% of the control). Similar experiments produced similar levels of decrease in neuron survival (e.g. 56.07% of the control). BDNF at 50 ng/mL rescued the neurons from cell death (p<0.001, *, 97.19% of the control). In similar experiments, BDNF rescued neurons from cell death at a similar level, e.g. 99.42% of the control).

Test antibody 1A12 at 250 nM (which was raised against cyclo(CGGTKEQGGGG) (SEQ ID NO: 49) shows a statistically significant effect on dopaminergic neuron survival (p<0.05, *, 83.15% of the control).

Test antibody 3C11 at 50 nM and 12B12 at 50 nM are able to rescue dopaminergic neurons from oligomer-induced cell death in a statistically significant manner (**, p<0.01, 89.60% and *, 79.77% of the control respectively. FIG. 8A)

Test antibody 2D6 at 250 nM and 11B6 at 250 nM (which were both raised against cyclo(CGGGGEKTKGG) (SEQ ID NO: 5) are able to rescue dopaminergic neurons from oligomer-induced cell death in a statistically significant manner (**, p<0.01, 83.80% and *, p<0.05, 81.01% of the control respectively).

Antibodies 1A12, 3C11, 12B12, 2D6 and 11B6 were able to rescue dopaminergic neurons from oligomer-induced cell death in a statistical significant manner. Antibody 2E9 approached statistical significance.

Figure 8B:
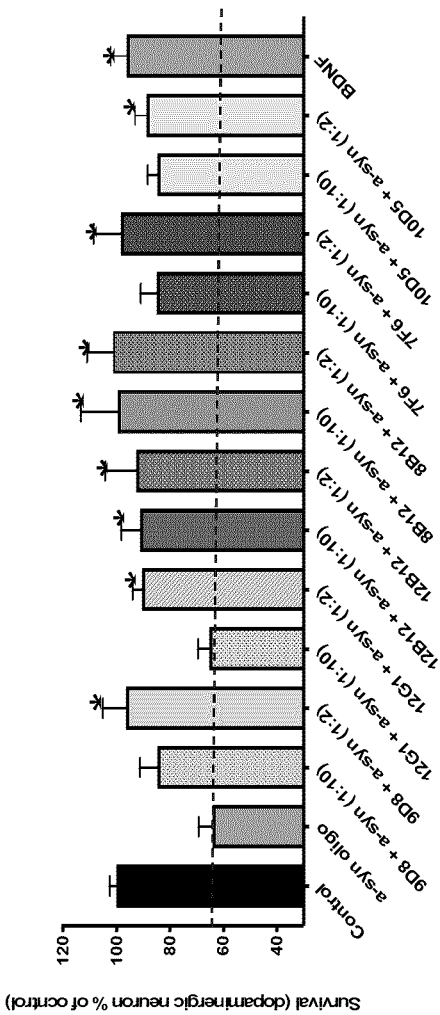
Figure 8C:
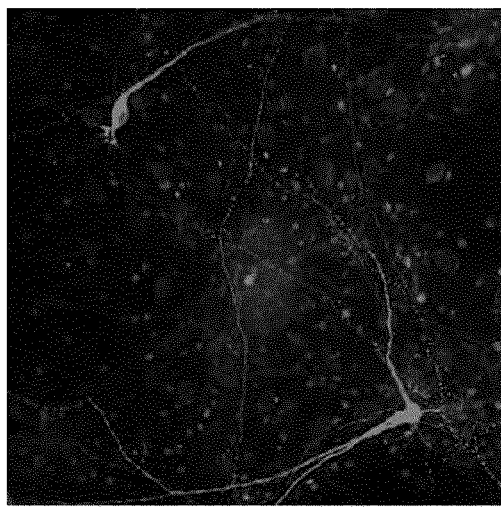
Figure 8D:
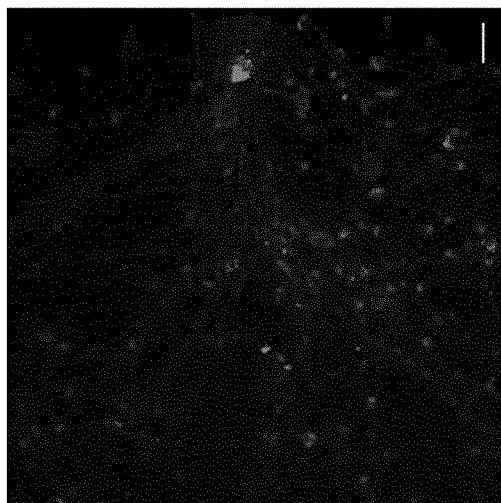
Figure 8H:
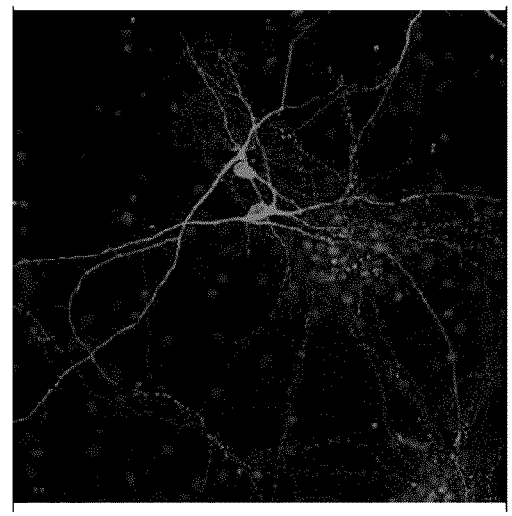
Figure 8G:
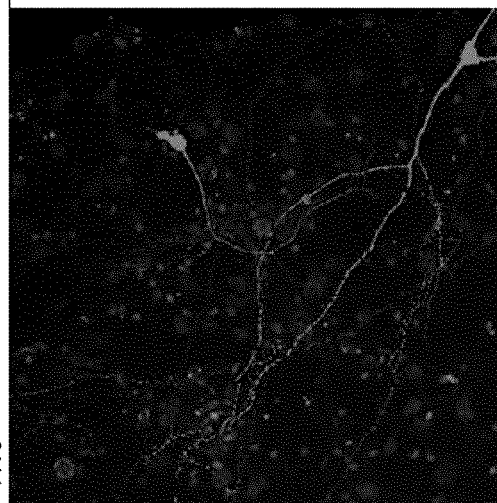
Figure 8F:
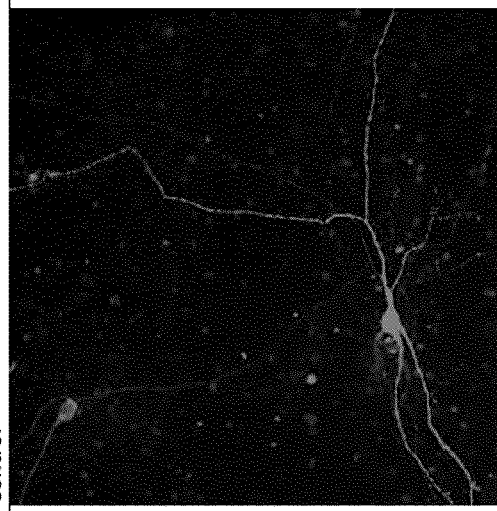

Results with additional clones are shown in FIG. 8B. FIGS. 8C-G are exemplary immunohistochemistry images showing dopaminergic neurons (stained for TH) and nuclei (stained with Hoechst solution) as described in the methods. FIG. 8C is control untreated neurons, showing dopaminergic neuron processes. FIG. 8D are cells treated with alpha-synuclein oligomers. No neuron processes are detectable. Neuron loss is prevented by antibodies of the application. FIG. 8E are cells treated with 2E9 antibody and α-synuclein oligomers; FIG. 8F are cells treated with 12G1 antibody and α-synuclein oligomers and FIG. 8G are cells treated with 12B12 antibody and α-synuclein oligomers, all showing protection of dopaminergic neurons from oligomer toxicity.

An alpha-synuclein oligomer preparation was shown in repeated tests to induce a large decrease of dopaminergic neurons survival (p<0.01, *, 62.98 to 64.50% of the control). Moreover, BDNF at 50 ng/mL is able to rescue neurons from the cell death induced by the preparation (p<0.001, *, 96.31-103.76% of the control).

Test antibodies 9D8 at 250 nM and 12G1 at 250 nM are able to rescue dopaminergic neuron death in a statistically significant manner (**, p<0.01, 96.47% and *, p<0.05, 90.59% of the control respectively).

Test antibodies 12B12 (at 250 nM and 50 nM) and antibody 10D5 at 250 nM are able to rescue dopaminergic neuron death in a statistically significant manner (**, p<0.01, 92.63%; *, p<0.05, 91.24% and *, p<0.05, 88.94% of the control respectively).

Test antibody 8B12 (at 250 nM and 50 nM) is able to rescue dopaminergic neuron death in a statistically significant manner (**, p<0.01, 101.44% and *, p<0.05, 99.52% of the control respectively).

Test antibody 7F6 at 250 nM is able to rescue dopaminergic neuron death in a statistically significant manner (**, p<0.01, 98.39% of the control respectively).

Example 11

Effect of Antibodies Against Alpha-Synuclein Aggregates Using Preformed Fibrils (PFFs) in Hippocampal Neurons Culture Model of Parkinson's Disease Sonicated synthetic preformed fibrils (PFFs; small soluble fibrils) have been shown to recruit endogenous α-syn and induce LB/LN pathology in vitro and in vivo, implicating propagation and cell-to-cell transmission of pathological α-syn as mechanisms for the progressive spread of LBs/LNs (Costanzo and Zurzolo, 2013; Guo and Lee, 2014).

The cell-to-cell spread of misfolded disease protein may involve their release followed by internalization. Immunotherapy may treat this neurodegenerative disease by neutralizing them in the extracellular space (Prusiner, 2012; Jucker and Walker, 2013).

The effect of test antibodies on internalization of synthetic alpha-syn and recruitment of endogenous alpha-syn to a pathological phosphorylated form was also tested using PFFs in hippocampal neuron cultures.

Methods

Rat hippocampal neurons were cultured as described by Harrison (1990). Pregnant females (Wistar, Janvier) at 17 days of gestation were killed by cervical dislocation. Hippocampi were rapidly and aseptically dissected from each brain in ice-cold medium of Leibovitz (L15, Panbiotech, Ref, P04-27055, batch: 4511117), followed by removal of meninges and mincing to small pieces. The hippocampal tissues were next digested by trypsinisation (Trypsin EDTA 1X; PanBiotech, ref P10-023100, batch 8970318) for 20 min at 37° C. The reaction was stopped by the addition of DMEM (Panbiotech, Ref P04-03600, batch: 5181217) containing DNAase I grade II (0.1 mg/ml Panbiotech, ref: P60-37780100, batch: H170706) and 10% of foetal calf serum (FCS, Invitrogen, ref: 10270-098, batch 42G2068K). Cells were mechanically dissociated by 3 passages through a 10 ml pipette. Cells were then centrifuged at 515×g for 10 min at 4° C. The supernatant was discarded and the pellet was re-suspended in a defined culture medium consisting of Neurobasal (Nb, Invitrogen, ref 21103049, batch 1979084) supplemented with 2% of B27 (Invitrogen, ref 17504-044, batch: 1969926), 2 mM of L-glutamine (PanBiotech, ref P04-80100, batch: 8440517), 2% of PS solution and 10 ng/ml of BDNF (Peprotech, ref: 450-02, batch: 021861). Viable cells were counted in a Neubauer cytometer using the trypan blue exclusion test. In this condition, after 3 days of culture, the hippocampal neurons culture contains less than 5% of astrocytes.

The cells were seeded at a density of 20 000 cells/well in 96 well-plates (wells are pre-coated with poly-D-lysine (Greiner)) and cultured at 37° C. in a humidified air (95%)/CO2 (5%) atmosphere. Half of the medium was changed every 2 days with fresh medium. The culture was used after 7 days of culture.

Alpha-Synuclein Preparation and Cell Culture Injury

Human α-syn peptide (Proteos) was prepared as described by Volpicelli-Daley et al.(2014). Human α-syn peptide was thawed and centrifuged at 12 000 g at 4° C. 10 min to pellet any aggregated material. Supernatant was used for the generation of PFFs. The concentration was adjusted to 5 mg/mL and 500 µL of it was shaking at 37° C. at 1 000 RPM during 7 days. At this step, PFFs were aliquoted and stored at −80° C. until use.

The α-syn PFFs preparation was used on primary hippocampal neurons after 7 days of culture.

PFFs were diluted at 0.1 mg/ml in sterile PBS and the suspension was sonicated with 60 pulses of 0.5 seconds at 10% power. Then sonicated PFFs solution was diluted at 1 μg/mL in hippocampal neurons medium and added on neurons cells culture.

The test antibodies and the alpha-syn toxin (sonicated PFFs) were pre-incubated together for 30 min at room temperature before adding the mixture to the neuronal cultures.

Cells were incubated with test compounds at the same time. The following conditions were done:
Control (vehicle)/vehicle for 14 days
α-synuclein PFFs (1 μg/mL, 14 days)
α-synuclein PFFs (1 μg/mL, 14 days)+test antibodies (0.25 μM and 0.05 μM)
Medium was changed once a week without new addition of fibrils.
One culture and 6 wells by condition were done.

Alpha Synuclein Aggregate Evaluation

After 14 days of intoxication, cells were fixed by a solution of 4% paraformaldehyde (Sigma, ref 6148, batch: SZBE2390V)/4% sucrose (Sigma, Ref: 57903-250G, Batch: BCBV9208)/1% triton X-100 (Sigma) for 15 min at room temperature. The cells were then permeabilized and blocked by a solution of phosphate buffered saline (PBS; PanBiotech, ref: P04-36500, Batch: 6760918) containing 3% Bovine Serum Albumin (BSA, Dutcher, Ref: P06-1391100, batch: H160810) and 0.1% of triton 15 min at room temperature (RT).

For human α-synuclein quantification, cells were incubated overnight at 4° C. in blocking buffer (PBS, 3% BSA) with:
Chicken primary antibody against Microtubule associated Protein (MAP2, Abcam, ref:ab5392, batch: GR3209140-2)
Rabbit primary antibody anti-α-synuclein (Thermofisher, ref 701085, batch 1920377-3) at 1/500.

For endogenous pathologic α-synuclein quantification, cells were incubated overnight at 4° C. in blocking buffer with:
Chicken primary antibody against Microtubule associated Protein (MAP2, Abcam, ref:ab5392, batch: GR3209140-2)
Rabbit primary antibody anti-Phosphorylatd Ser 129 α-synuclein (abcam, ref ab51253, batch: GR3232346-1) at 1/500.

These antibodies were revealed with Alexa Fluor 633 goat anti-rabbit IgG (Molecular probe, ref: A21070, Batch: 1700326) and Alexa Fluor 568 goat anti-chicken (Molecular probe, ref: A110041, batch: 1776042) in PBS 3% BSA, for 1 h at room temperature. Nuclei of cells were labeled by a fluorescent marker (Hoechst solution, SIGMA, ref: B1155, Batch: 046M4048V) in the same solution.

For each condition, multiple pictures per well were taken using InCell Analyzer™ 2200 (GE Healthcare) with 20× magnification. Analysis of MAP2 positive neurons and α-synuclein aggregates were performed using Developer software (GE healthcare). All values were expressed as mean±SEM. Statistical analyses were done on different conditions.

Statistics

The data were expressed as mean±SEM (of 6 data per condition, 1 culture). A global analysis of the data was performed using a one-way analysis of variance (ANOVA) following by Dunnett's test. The level of significance is set at $p < 0.05$.

Results

The effect of test antibodies on human alpha synuclein aggregates in hippocampal neurons injured by PFFs preparation is shown in FIGS. 13-14.

Figure 13C:
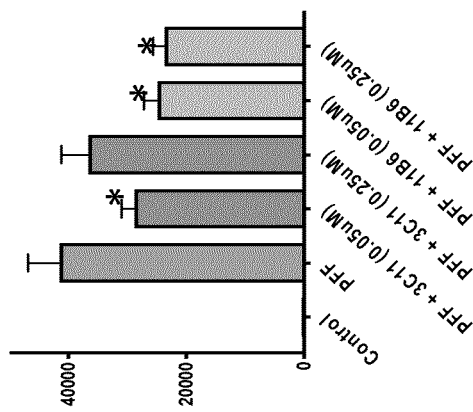
Figure 13B:
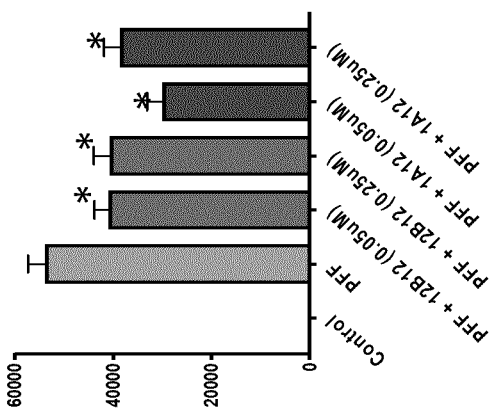
Figure 13A:
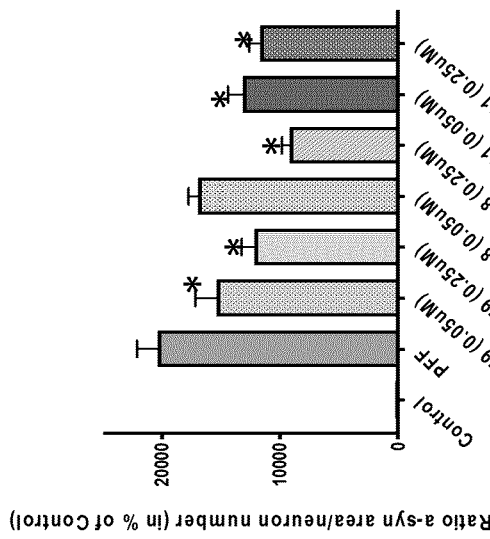

As shown in FIG. 13A, the PFFs preparation induces a large and significant increase of human alpha synuclein aggregates ($p<0.001$, ***, 20376% of the control).

Antibodies 2E9 (***, $p<0.001$, 12168% of the control at 0.25 μM; *, $p<0.05$ 15387% of the control at 0.05 μM), 9D8 (*, $p<0.001$, 9181% of the control at 0.25 μM), and 12G1 (*, $p<0.001$, 11694% of the control at 0.25 μM and 13156% of the control at 0.05 μM) are able to decrease human α-synuclein aggregates in a statistically significant manner.

As shown in FIG. 13B, the PFFs preparation induces a large and significant increase of human alpha synuclein aggregates ($p<0.001$, ***, 53941% of the control). Antibodies 12B12 (*, $p<0.05$, 40717% of the control at 0.25 μM and 41007% of the control at 0.05 μM), and 1A12 (, $p<0.01$, 38641% of the control at 0.25 μM and *, $p<0.001$ 30064% of the control at 0.05 μM) are able to decrease human α-syn aggregates in a statistically significant manner.

As shown in FIG. 13C, the PFFs preparation induces a large and significant increase of human alpha synuclein aggregates ($p<0.001$, ***, 41528% of the control).

Antibodies 3C11 (*, $p<0.05$, 28829% of the control at 0.05 μM) and 11B6 (*, $p<0.001$, 23690% of the control at 0.25 μM and , $p<0.01$ 24897% of the control at 0.05 μM) are able to decrease human α-syn aggregates in a statistically significant manner.

Figure 13I:
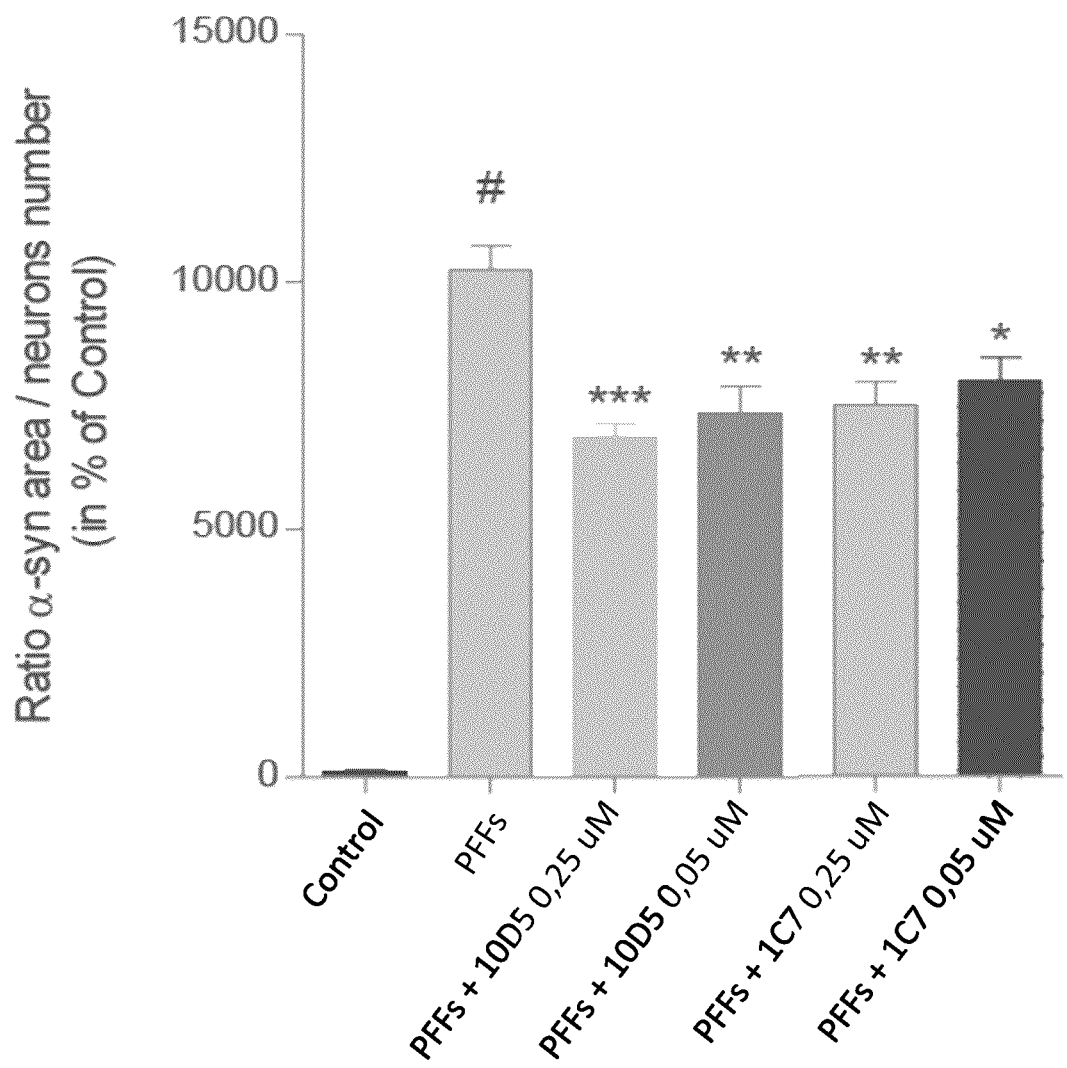

As shown in FIG. 13I, the effect of the 10D5 and 1C7 antibodies on internalization of pre-formed α-Syn fibrils (PFFs) was tested according to the protocol described in this Example. Both antibodies significantly decreased PFF uptake and induction of aggregation. For mean+SEM, * denotes $p<0.05$,  denotes $p<0.01$, * denotes $p<0.001$, and #denotes PFFs alone.

Exemplary images are shown in FIGS. 13D-H. FIG. 13D shows control cells stained for neuronal marker MAP2 illustrating the long neuronal processes and cell bodies of the neurons. Nuclei are stained as described in the methods. FIG. 13E shows cells treated with α-synuclein PFF. α-synuclein PFF is visible as bright punctate staining denoting aggregates. FIGS. 13F-H, shows cells where the α-synuclein PFF is first incubated with test antibodies. Aggregates are visibly less numerous.

Figure 14B:
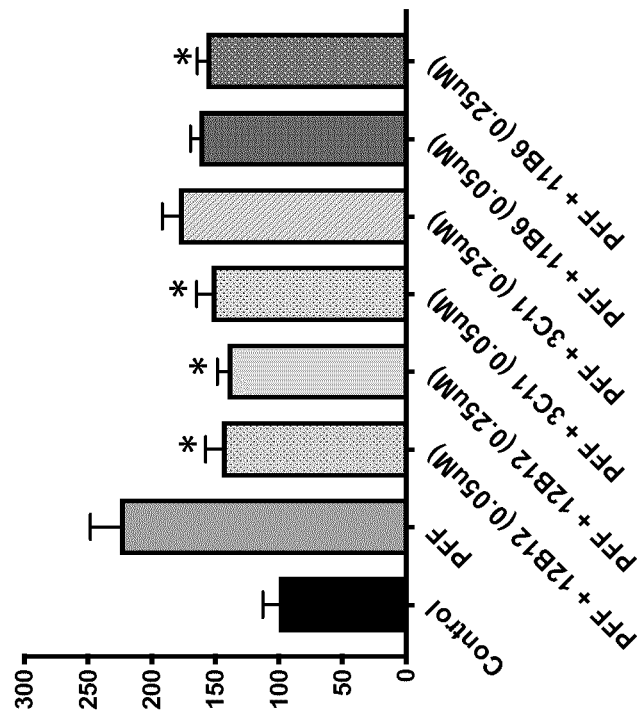
Figure 14A:
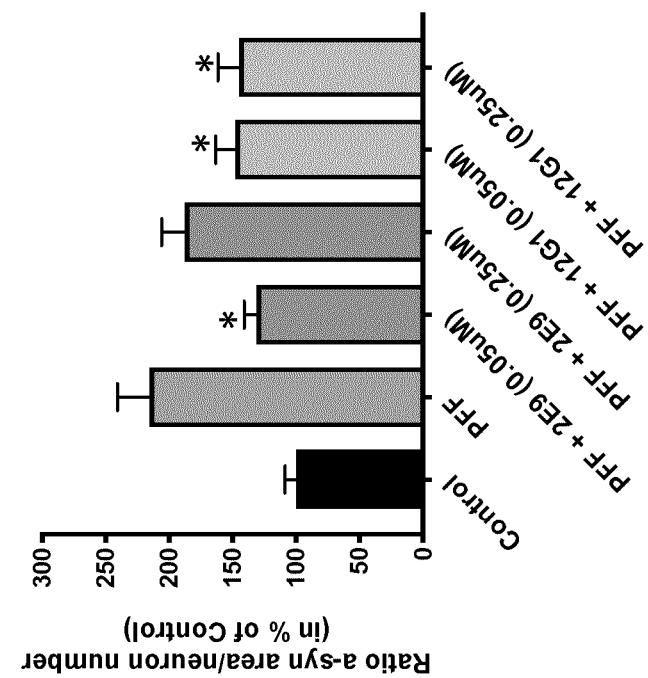

The effect of test antibodies on the recruitment of phosphorylated endogenous rat alpha synuclein aggregates in hippocampal neurons exposed to human PFFs alpha synuclein preparation is shown in FIGS. 14A and 14B.

As observed on FIG. 14A, PFFs preparation induces a large and significant increase of endogenous phosphorylated alpha synuclein aggregates ($p<0.001$, ***, 215.26% of the control).

Antibodies 2E9 at 0.05 μM (**, $p<0.01$, 131.13% of the control) and 12G1 at 0.25 μM and 0.05 μM (*, $p<0.05$ 144.81% and 147.77% of the control respectively) are able to decrease endogenous phosphorylated α-syn aggregates in a statistically significant manner.

As observed on FIG. 14B, PFFs preparation induces a large and significant increase of endogenous phosphorylated alpha synuclein aggregates (p<0.001, ***, 225.18% of the control).

Antibody 12B12 at 0.25 µM and 0.05 µM is able to statistically decrease endogenous phosphorylated α-syn aggregates (*, p<0.05 140.44% and 144.88% of the control respectively).

Antibodies 3C11 at 0.05 µM (*, p<0.05, 152.89% of the control), and 11B6 at 0.25 µM (*, p<0.05 156.71% of the control respectively) are able to statistically decrease endogenous phosphorylated α-syn aggregates.

Figure 14H:
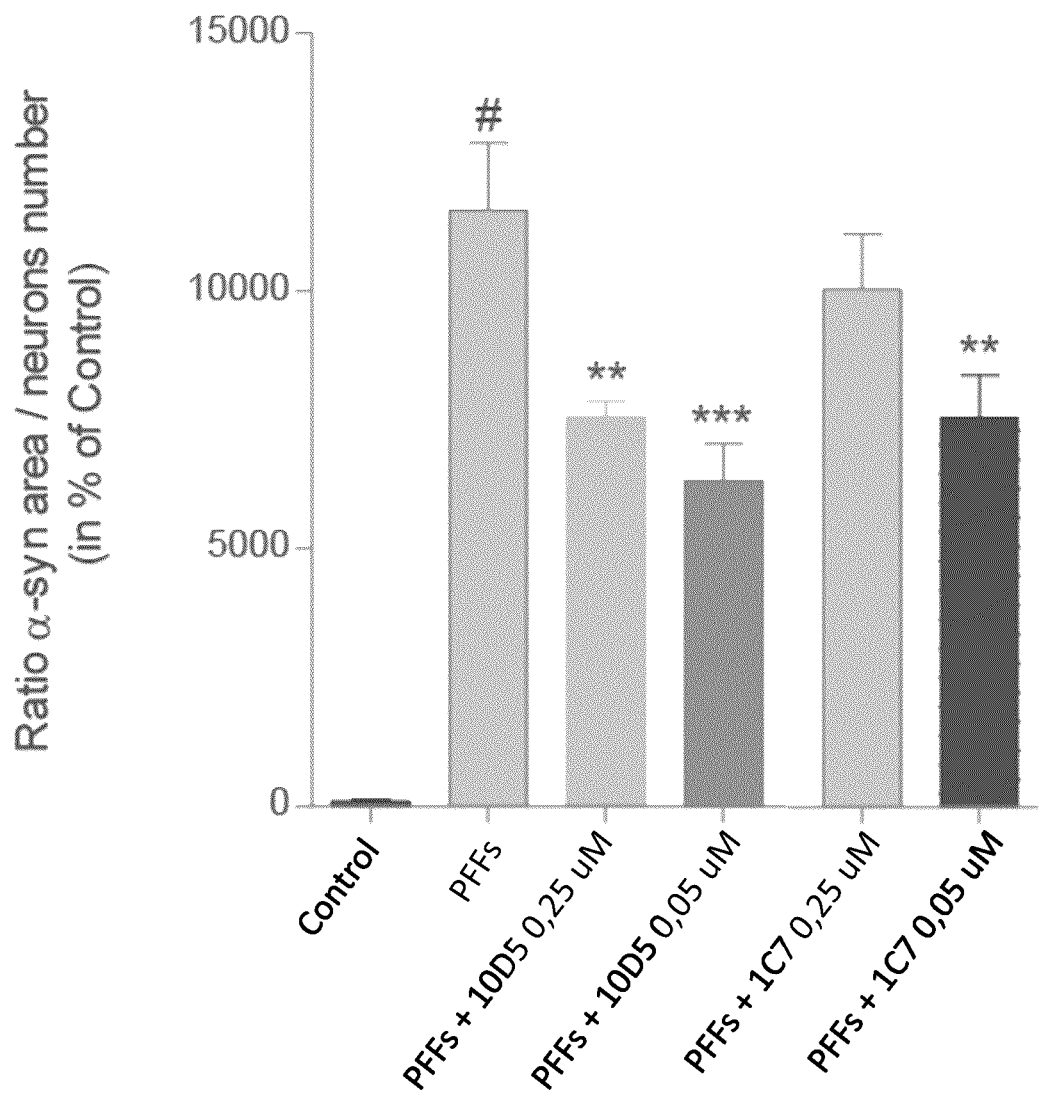

As shown in FIG. 14H, The effect of the 10D5 and 1C7 antibodies on recruitment of endogenous α-Syn to a pathological phosphorylated form was tested according to the protocol described in this Example. Both antibodies significantly decreased PFF uptake and induction of aggregation. For mean+SEM,  denotes p<0.01, * denotes p<0.001, and #denotes PFFs alone.

Exemplary images are shown in FIGS. 14C-G. FIG. 14C shows control cells. FIG. 14D shows PFF treated cells showing extensive phosphorylated α-syn aggregate staining. Examples of phosphorylated aggregates inside the neurons are identified by arrows. FIGS. 14E-G show that pre-incubation of PFFs with test antibodies dramatically decreases endogenous phosphorylated α-syn aggregate staining.

Tested antibodies 2E9, 12G1, 12B12, 3C11 and 11B6 are able to reduce endogenous phosphorylated α-syn aggregates in a statistically significant manner.

Example 12

Immunohistochemistry (IHC) Staining and Immunofluorescence of LBD Brain and Bormal Brain Frozen sections from the brain frontal cortex of a patient with Lewy body dementia (LBD) were exposed to the test antibodies (2E9, 12B12 or 3C11) or control antibodies at a concentration of 4 µg/ml. Similarly, frozen sections from the brain frontal cortex of a normal individual were exposed to the test antibodies (12B12, 12G1, 3C11, 2E9, 11B6 and 9D8) at a concentration of 10 µg/ml. Bound antibody was detected by the addition of horseradish peroxidase-conjugated sheep anti-mouse IgG (ECL, 1:1000 dilution) or rabbit anti-human IgG (Abcam, 1:5000 dilution). Diaminobezidine (DAB) chromogen reagent, the HRP enzyme substrate (Vector Laboratories), was then added to the sections to produce a brown color. The sections were counterstained with hematoxylin to visualize the cells and cell nuclei (bluish purple staining). For immunofluorescence, detection of bound antibody was performed using Alexa fluor 568-conjugated goat anti-mouse IgG (Invitrogen) at a 1:1000 working concentration with DAPI counterstaining.

Results

Figure 10A:
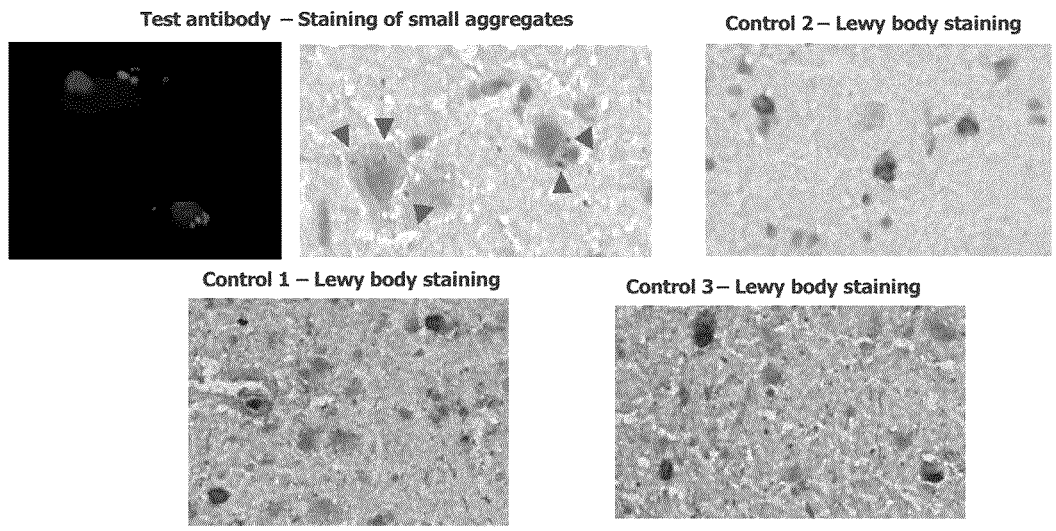
FIGS. 10A to E are images showing that alpha-syn test antibodies prefentially stain small aggregates of alpha-syn over dense Lewy bodies by IHC and immunofluorescent staining.
Figure 10B:
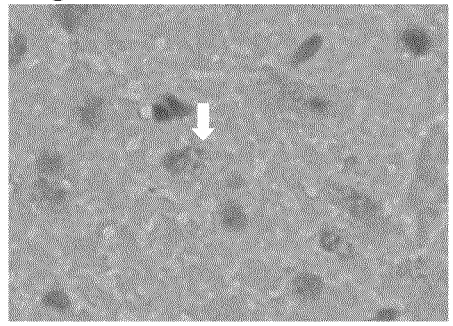
Figure 10C:
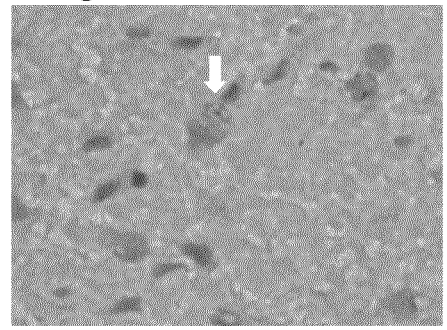
Figure 10D:
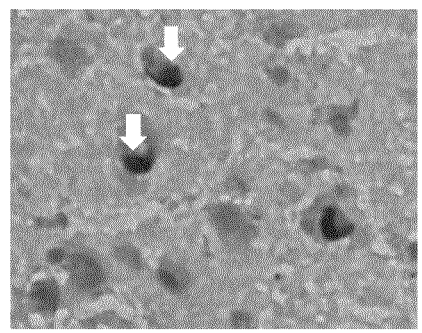
Figure 10E:
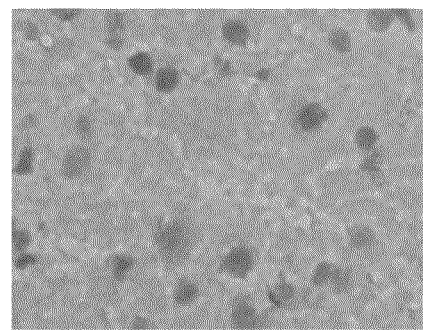

IHC staining demonstrates that alpha-syn antibodies according to the present disclosure preferentially bind to small aggregates over dense Lewy bodies (insoluble fibril deposits), as shown in FIG. 10A (2E9) and FIG. 10B (12612) and FIG. 10C (3C11). FIG. 10D shows pan alpha-syn 4D6 antibody staining of Lewy bodies and FIG. 10E shows mouse IgG1 control. The arrows in FIGS. 10A, B and C point to staining of small aggregates with test antibodies whereas in FIG. 10D the arrows identify that Lewy Bodies are stained by the pan alpha syn antibody. The test antibodies show greater selectivity for small disease promoting aggregates over Lewy Bodies. Immunofluorescense staining for the test antibody was also performed (FIG. 10A left top panel) consistent with the results seen with IHC.

Figure 10F:
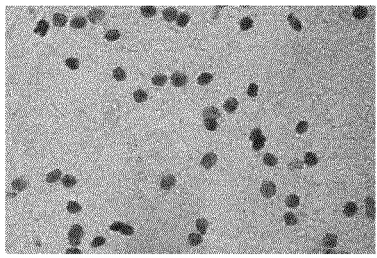
FIGS. 10F to K are images showing that alpha-syn test antibodies do not give rise to detectable staining of normal brain by IHC.
Figure 10G:
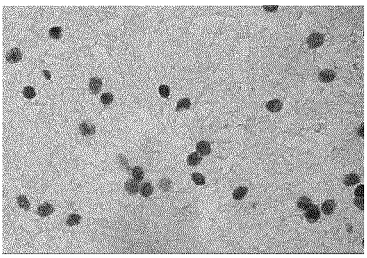
Figure 10H:
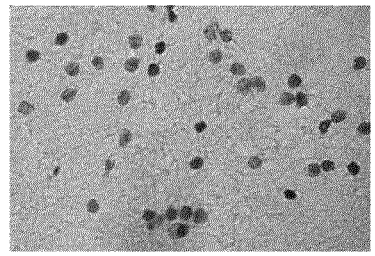
Figure 10I:
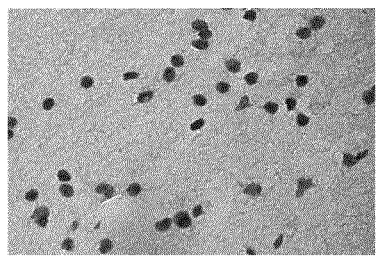
Figure 10J:
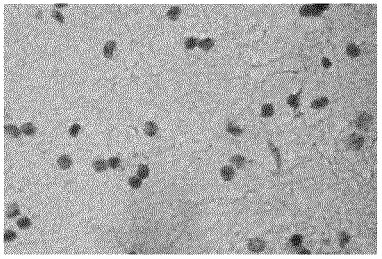
Figure 10K:
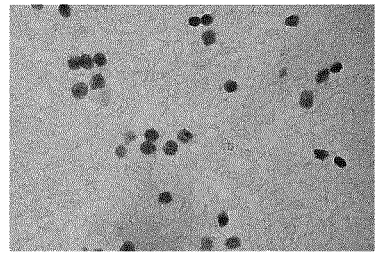

IHC staining also demonstrates that none the test antibodies 12B12, 12G1, 3C11, 2E9, 11B6 and 9D8 gave rise to detectable staining of normal brain (100× magnification) as shown in FIG. 10F (12B12), FIG. 10G (12G1), FIG. 10H (3C11), FIG. 10I (2E9), FIG. 10J (11B6) and FIG. 10K (9D8).

Example 13

Specificity—Ligand Blocking

Figure 12A:
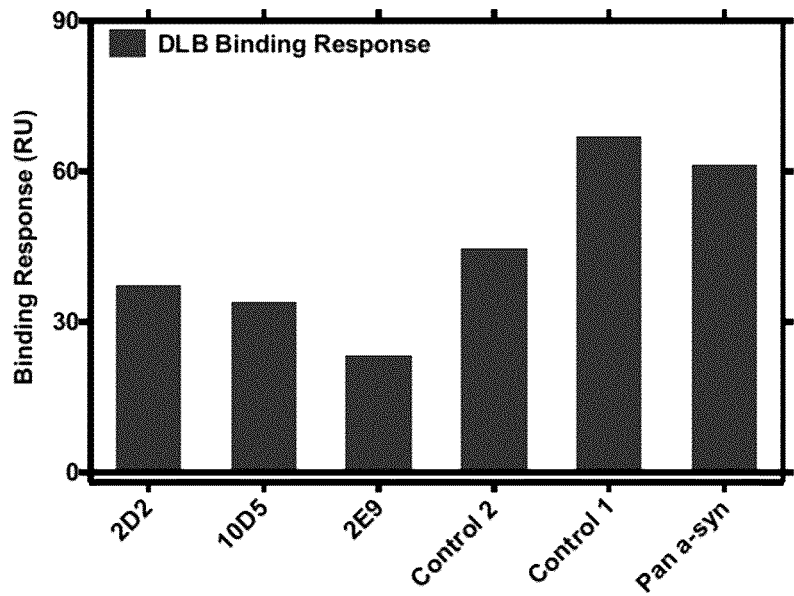
FIG. 12A-B are a series of graphs.
Figure 12B:
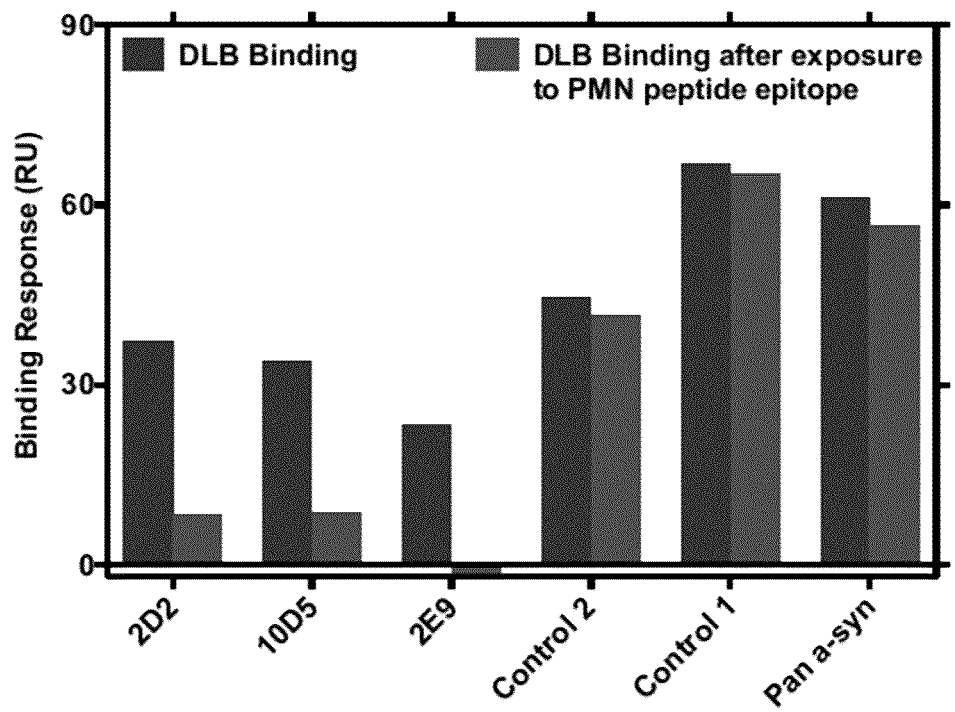

The binding specificity of test antibodies to alpha-syn in soluble DLB brain extract was also tested in a ligand blocking assay. As shown in FIG. 12A, test antibodies bound to DLB brain extract. As shown in FIG. 12B, the binding of test antibodies to DLB extract is epitope-specific, i.e., it is inhibited by exposure to a peptide comprising the epitope sequence used to raise the antibody. Pan alpha-syn 4D6, control 1 (Human IgG, Prasinezumab, PRX002/RG7935, Creative Labs) and control 2 (Mouse IgG, BAN0805, mAb49/G, Creative Labs) antibodies recognize a different epitope so their binding to DLB extract is not blocked by the test antibody peptide comprising epitope sequence.

Example 14

Prion-like propagation of aggregated alpha-synuclein (α-Syn) underlies the progression of Parkinson's disease (PD), Lewy-body dementia (LBD), and multiple systems atrophy (MSA). α-Syn oligomers and small soluble fibrils have been implicated in the neurotoxicity and propagation of α-Syn, respectively (Fusco 2017 Science; Choi 2018 Cell Reports). Epitopes were identified that would allow for targeting of these pathogenic species while sparing normal α-Syn monomers and physiological tetramers (Nuber 2018 Neuron).

Methods: Using Collective Coordinates (described in described in WO/2017/079836 and Peng et al 2018), conformational epitopes were identified which were predicted to be exposed on α-Syn oligomers, and to a lesser extent fibril fragments/protofibrils, but not on large fibrils, physiological tetramers, or α-Syn monomers. Cyclic peptide scaffolds reproducing the conformational epitopes were used to generate mouse monoclonal antibodies which were then screened for selectivity of binding and biological activity in vitro.

Results: Using surface plasmon resonance (SPR), antibody candidates were identified that showed selective binding to synthetic α-Syn oligomers and soluble sonicated fibrils, with little or no binding to monomers or physiological tetramers. Recognition of native α-Syn aggregates in LBD brain extracts was confirmed by SPR and dot blot. Immunohistochemistry confirmed minimal binding to Lewy bodies. In vitro, the antibodies protected primary rodent neurons against the toxicity of α-Syn oligomers and inhibited mechanisms involved in α-Syn propagation i.e. uptake of sonicated preformed fibrils and induction of phosphorylated α-Syn aggregates.

Conclusions: The "tuning" of epitopes with Collective Coordinates allowed for the generation of selective antibodies with protective activity against pathogenic α-Syn.

Example 15

Antibody Sequencing

Variable regions of the heavy and light chain immunoglobulin gene for mouse hybridoma clones 2E9, 9D8, 12G1, 3C11, 12B12, 10D5 and 11B6 were identified and sequenced.

Method

Total RNA was isolated from the hybridoma cells and reverse-transcribed into cDNA using either isotype-specific anti-sense primers or universal primers. Antibody fragments of heavy chain and light chain were amplified by rapid amplification of cDNA ends (RACE). Amplified antibody fragments were cloned into a standard cloning vector separately. Colony PCR was performed to screen for clones with inserts of correct sizes. Per hybridoma cell line, 5 clones were selected and sequenced for both heavy and light chains. Sequence alignment was performed with the 5 clones to confidently determine the heavy and light chain sequences for each monoclonal antibody.

Analysis of Amino Acid and Nucleic Acid Sequences

Tables 13 and 14 below set out the nucleic acid and amino acid sequences of complementarity determining regions (CDRs) and of the heavy and light chains, respectively, of each of the antibody clones 2E9, 9D8, 12G1, 3C11, 12B12, 10D5 and 11B6, as determined according to IgBLAST. CDRs of heavy and light chains in Table 14 are shown in bold.

TABLE 13

| | | | | CDR sequences | | | |
|---|---|---|---|---|---|---|---|
| Peptide Scaffold | Clone | Chain | CDR | Amino Acid Sequence | SEQ ID NO | Nucleic Acid Sequence | SEQ ID NO |
| 1, 4 | 2E9 | Heavy IgG1 | CDR1 | GFDFSRYW | 61 | GGATTCGATTTTAGTAGATACTGG | 97 |
| | | | CDR2 | INPHSSTI | 62 | ATTAATCCACATAGCAGTACGATA | 98 |
| | | | CDR3 | GRGDYVDY | 63 | GGAAGAGGAGACTACGTTGACTAC | 99 |
| | | Light Kappa | CDR1 | QSLLYSRNQKNY | 64 | CAGAGCCTTTTATATAGTAGAAATCAAAAGAACTAC | 100 |
| | | | CDR2 | WAS | 65 | TGGGCATCC | 101 |
| | | | CDR3 | QQYYSYPRT | 66 | CAGCAATATTATAGCTATCCTCGGACG | 102 |
| | 10D5 | Heavy IgG1 | CDR1 | GFNIKDYY | 180 | GGCTTCAACATTAAAGACTACTAT | 185 |
| | | | CDR2 | IDPENDNT | 181 | ATTGATCCTGAGAATGATAATACT | 186 |
| | | | CDR3 | AMGGFTY | 182 | GCTATGGGGGGTTTTACTTAC | 187 |
| | | Light kappa | CDR1 | QSLLHSDGKTY | 183 | CAGAGCCTCTTACATAGTGATGGAAAGACATAT | 188 |
| | | | CDR2 | LVS | 77 | CTGGTGTCT | 113 |
| | | | CDR3 | WQGTHFPRT | 184 | TGGCAAGGTACACATTTTCCTCGGACG | 189 |
| 2, 4 | 9D8 | Heavy IgG1 | CDR1 | GFSLSTSGMG | 67 | GGGTTTTCACTGAGCACTTCTGGTATGGGT | 103 |
| | | | CDR2 | IWWDGDK | 68 | ATTTGGTGGGATGGTGACAAG | 104 |
| | | | CDR3 | TRIWPNFLFTY | 69 | ACTCGAATAGTAGTTCCTAACTTCCTGTTTACTTAC | 105 |
| | | Light Kappa | CDR1 | QSIVQSNGNTY | 70 | CAGAGCATTGTACAAAGTAATGGAAACACCTAT | 106 |
| | | | CDR2 | KVS | 71 | AAAGTTTCC | 107 |
| | | | CDR3 | FQGSHVPFT | 72 | TTTCAAGGTTCACATGTTCCATTCACG | 108 |
| | 12G1 | Heavy IgG1 | CDR1 | GYTFTTAG | 73 | GGGTATACCTTCACAACTGCTGGA | 109 |
| | | | CDR2 | INTHSGVP | 74 | ATAAATACCCACTCTGGAGTGCCA | 110 |
| | | | CDR3 | ARTSWAPY | 75 | GCGAGAACTTCCTGGGCTCCTTAC | 111 |
| | | Light Kappa | CDR1 | QSLLDSDGKTY | 76 | CAGAGCCTCTTAGATAGTGATGGAAAGACATAT | 112 |
| | | | CDR2 | LVS | 77 | CTGGTGTCT | 113 |
| | | | CDR3 | WQGTHFPQT | 78 | TGGCAAGGTACACATTTTCCTCAGACG | 114 |

TABLE 13-continued

CDR sequences

| Peptide Scaffold | Clone | Chain | CDR | Amino Acid Sequence | SEQ ID NO | Nucleic Acid Sequence | SEQ ID NO |
|---|---|---|---|---|---|---|---|
| 3, 2 | 3C11 | Heavy IgG1 | CDR1 | GFNIKDTY | 79 | GGCTTCAACATTAAAGACACCTAT | 115 |
| | | | CDR2 | IDPANGNT | 80 | ATTGATCCTGCGAATGGTAATACT | 116 |
| | | | CDR3 | SNWDYFDY | 81 | TCTAACTGGGATTACTTTGACTAC | 117 |
| | | Light Kappa | CDR1 | QSLLDSDGKTY | 76 | CAGAGCCTCTTAGATAGTGATGGAAAGACATAT | 112 |
| | | | CDR2 | LVS | 77 | CTGGTGTCT | 113 |
| | | | CDR3 | SQGTHFPRT | 84 | TCGCAAGGTACACATTTTCCTCGGACG | 120 |
| | 12B12 | Heavy IgG1 | CDR1 | GFNIKDTY | 79 | GGCTTCAACATTAAAGACACCTAT | 115 |
| | | | CDR2 | IDPANGNT | 80 | ATTGATCCTGCGAATGGTAATACT | 116 |
| | | | CDR3 | SNWDYFDY | 81 | TCGAACTGGGATTACTTTGACTAC | 123 |
| | | Light Kappa | CDR1 | QSLLDSDGKTY | 76 | CAGAGCCTCTTAGATAGTGATGGAAAGACATAT | 112 |
| | | | CDR2 | LVS | 77 | CTGGTGTCT | 113 |
| | | | CDR3 | SQGTHFPRT | 84 | TCGCAAGGTACACATTTTCCTCGGACG | 120 |
| 4, 2 | 11B6 | Heavy IgG1 | CDR1 | GYTFSSYW | 91 | GGCTACACATTCAGTAGTTACTGG | 127 |
| | | | CDR2 | IFPGSGSA | 92 | ATTTTCCCTGGAAGTGGTAGTGCT | 128 |
| | | | CDR3 | TSRWYPDYFEY | 93 | ACAAGTAGATGGTATCCTGACTACTTTGAATAT | 129 |
| | | Light Kappa | CDR1 | QSLVHSNGNTY | 94 | CAGAGCCTTGTACACAGTAATGGAAACACCTAT | 130 |
| | | | CDR2 | KVS | 71 | AAAGTTTCC | 107 |
| | | | CDR3 | SQSTHVPYT | 96 | TCTCAAAGTACACATGTTCCGTACACG | 132 |

TABLE 14

Sequences of variable heavy and light chains

| Peptide Scaffold | Clone | Chain | Amino acid sequence | SEQ ID NO | Nucleic acid sequence | SEQ ID NO |
|---|---|---|---|---|---|---|
| 1, 4 | 2E9 | Heavy IgG1 | EVKLLESGGGLVQPGGSLKLSCAASGFDFSRYWMNWVRQAPGKGLEWIGEINPHSSTINYAPSLKDKFIISRDNAKNTLYLQMSKVRSEDTALYYCGRGDYVDYWGLGTTLTVSS | 133 | GAGGTGAAGCTTCTCGAGTCTGGAGGTGGCCTGGTGCAGCCTGGAGGATCCCTGAAACTCTCCTGTGCAGCCTCAGGATTCGATTTTAGTAGATACTGGATGAATTGGGTCCGGCAGGCTCCAGGGAAAGGGCTAGAATGGATTGGAGAAATTAATCCACATAGCAGTACGATAAACTATGCGCCATCTCTAAAGGATAAATTCATCATCTCCAGAGACAACGCCAAAAATACGCTGTACCTGCAAATGAGCAAAGTGAGATCTGAGGACACAGCCCTTTATTACTGTGGAAGAGGAGACTACGTTGACTACTGGGGCCTAGGCACCACTCTCACAGTCTCCTCA | 145 |
| | | Light Kappa | DIVMSQSPSSLAVSVGEKVTMSCKSSQSLLYSRNQKNYLAWYQQKPGQSPKLLIYWASTRESGVPDRFTGSGSGTDFTLTISSVKADDLAVYYCQQYYSYPRTFGGGTKLEIK | 134 | GACATTGTGATGTCACAGTCTCCATCCTCCCTAGCTGTGTCAGTTGGAGAGAAGGTTACTATGAGCTGCAAGTCCAGTCAGAGCCTTTTATATAGTAGAAATCAAAAGAACTACTTGGCCTGGTACCAGCAGAAACCAGGGCAGTCTCCTAAACTGCTGATTTACTGGGCATCCACTAGGGAATCTGGGGTCCCTGATCGCTTCACAGGCAGTGGATCTGGGACAGATTTCACTCTCACCATCAGCAGTGTGAAGGCTGATGACCTGGCAGTTTATTACTGTCAGCAATATTATAGCTATCCTCGGACGTTCGGTGGAGGCACCAAGCTGGAAATCAAA | 146 |
| | 10D5 | Heavy IgG1 | EVQLQQSGAELVRPGALVKLSCKGSGFNIKDYYMSWVKQRPEQGLEWIGWIDPENDNTIYDSKFQGKASITADTSSNTAYLQFSSLTPEDTAVYYCAMGGFTYWGQGTLVTVSA | 190 | GAGGTTCAGCTGCAGCAGTCTGGGGCTGAGCTTGTGAGGCCAGGGGCCTTAGTCAAGTTGTCCTGCAAAGGTTCTGGCTTCAACATTAAAGACTACTATATGAGTTGGGTGAAGCAGAGGCCTGAACAGGGCCTGGAATGGATTGGATGGATTGATCCTGAGAATGATAATACTATATATGACTCGAAGTTCCAGGGCAAGGCCAGTATAACAGCAGACACTTCCTCCAACACAGCCTACCTGCAGTTCAGCAGCCTGACACCTGAGGACACTGCCGTCTATTACTGTGCTATGGGGGGTTTTACTTACTGGGGCCAAGGGACTCTGGTCACTGTCTCTGCA | 192 |
| | | Light Kappa | DVVMTQTPLTLSVTIGQPASISCKSSQSLLHSDGKTYLNWLLQRPGQSPKRLIYLVSKLDSGVPDRFTGSGSGTDFTLKISRVEAEDLGVYYCWQGTHFPRTFGGGTKLEIK | 191 | GATGTTGTGATGACCCAGACTCCACTCACTTTGTCGGTTACCATTGGACAACCAGCCTCCATCTCTTGCAAGTCAAGTCAGAGCCTTCTTACATAGTGATGGAAAGACATATTTGAATTGGTTGTTACAGAGGCCAGGCCAGTCTCCAAAGCGCCTAATCTATCTGGTGTCTAAACTGGACTCTGGAGTCCCTGACAGGTTCACTGGCAGTGGATCAGGGACAGATTTCACACTGAAAATCAGCAGAGTGGAGGCTGAGGATTTGGGAGTTTATTATTGCTGGCAAGGTACACATTTTCCTCGGACGTTCGGTGGAGGCACCAAGCTGGAAATCAAA | 193 |
| 2, 4 | 9D8 | Heavy IgG1 | QVTLKESGPGILQPSQTLSLTCSFSGFSLSTSGMGVGWIRQPSGKGLEWLAHIWWDGDKRYNPALRSRLTISKDTSSN | 135 | CAGGTTACTCTGAAAGAGTCTGGCCCTGGGATATTGCAGCCCTCCCAGACCCTCAGTCTGACTTGTTCTTTCTCTGGGTTTTCACTGAGCACTTCTGGTATGGGTGTAGGCTGGATTCGTCAGCCTTCAGGGAAGGGTCTGGAGTGGCTGGCACACATTTGGTGGGATGGTGACAAGCGCTATAACCCAGCCCTGAGGAGCCGACTGACAATCTCCAAGGATACCTCCAGCAAC | 147 |

TABLE 14-continued

Sequences of variable heavy and light chains

| Peptide Scaffold | Clone | Chain | Amino acid sequence | SEQ ID NO | Nucleic acid sequence | SEQ ID NO |
|---|---|---|---|---|---|---|
| | | | QVFLKIASVDTADTATYYCTRIVVPNFLFTYWGQGTLVTVSA | | CAGGTTTTCCTCAAGATCGCCAGTGTGGACACTGCAGATACTGCCACATACTACTGTACTCGAATAGTAGTTCCTAACTTCCTGTTTACTTACTGGGGCCAAGGGACTCTGGTCACTGTCTCTGCA | |
| | | Light Kappa | DVLMTQTPLSLPVSLGDQASISCRSSQSIVQSNGNTYLEWYLQKPGQSPNLLIYKVSNRFSGVPDRFSGSGSGTDFTLKISRVEAEDLGVYYCFQGSHVPFTFGSGTKLEIK | 136 | GATGTTTTGATGACCCAAACTCCACTCTCCCTGCCTGTCAGTCTTGGAGATCAAGCCTCCATCTCTTGCAGATCTAGTCAGAGCATTGTACAAAGTAATGGAAACACCTATTTAGAATGGTACCTTGCAGAAACCAGGCCAGTCTCCAAACCTCCTGATCTACAAAGTTTCCAACCGATTTTCTGGGGTCCCAGACAGGTTCAGTGGCAGTGGATCAGGGACAGATTTCACACTCAAGATCAGCAGAGTGGAGGCTGAGGATCTGGGAGTTTATTACTGCTTTCAAGGTTCACATGTTCCATTCACGTTCGGCTCGGGGACAAAGTTGGAAATAAAA | 148 |
| | 12G1 | Heavy IgG1 | QIQLVQSGPELRKPGETVRISCKASGYTFTTAGMQWVQKMPGKGLKWIGWINTHSGVPKYAEDFKGRFAFSLETSASTAYLQISNLKNEDTATYFCARTSWAPYWGQGTLVTVSA | 137 | CAGATCCAGTTGGTGCAGTCTGGACCTGAGCTGAGGAAGCCTGGAGAGACAGTCAGGATCTCCTGCAAGGCTTCTGGGTATACCTTCACAACTGCTGGAATGCAGTGGGTGCAAAAGATGCCAGGAAAGGGTTTGAAGTGGATTGGCTGGATAAATACCCACTCTGGAGTGCCAAATATGCAGAAGACTTCAAGGGACGGTTTGCCTTCTCTTTGGAAACCTCCGCCAGCACTGCATATTTACAGATAAGCAACCTCAAAAATGAGGACACGGCTACGTATTTCTGTGCGAGAACTTCCTGGGCTCCTTACTGGGGCCAAGGGACTCTGGTCACTGTCTCTGCA | 149 |
| | | Light Kappa | DVVMTQTPLTLSVTIGQPASISCKSSQSLLDSDGKTYLNWLLQRPGQSPKRLIYLVSKLDSGVPDRFTGSGSGTDFTLKISRVEAEDLGVYYCWQGTHFPQTFGGGTKLEIK | 138 | GATGTTGTGATGACCCAGACTCCACTCACTTTGTCGGTTACCATTGGACAACCAGCCTCCATCTCTTGCAAGTCAAGTCAGAGCCTCTTAGATAGTGATGGAAAGACATATTTGAATTGGTTGTTACAGAGGCCAGGCCAGTCTCCAAAGCGCCTAATCTATCTGGTGTCTAAACTGGACTCTGGAGTCCCTGACAGGTTCACTGGCAGTGGATCAGGGACAGACTTCACACTGAAAATCAGCAGAGTGGAGGCTGAGGATTTGGGAGTTTATTATTGCTGGCAAGGTACACATTTTCCTCAGACGTTCGGTGGAGGCACCAAGCTGGAAATCAAA | 150 |
| 3, 2 | 3C11 | Heavy IgG1 | SEVQLQQSGAELVKPGASVKLSCTASGFNIKDTYIHWMKQRPEQGLEWIGRIDPANGNTKYDPEFQDKATIAADTSSNTAYLQLSSLTSEDTAVYYCSNWDYFDYWGQGTALTVSS | 139 | GAGGTTCAGCTGCAGCAGTCTGGGGCAGAACTTGTGAAGCCAGGGGCCTCAGTCAAGTTGTCCTGCACAGCTTCTGGCTTCAACATTAAAGACACCTATATACACTGGATGAAGCAGAGGCCTGAACAGGGCCTGGAGTGGATTGGAGGGATTGATCCTGCGAATGGTAATACTAAATATGACCCGGAGTTCCAGGACAAGGCCACTATAGCAGCAGACACATCCTCCAACACAGCCTACCTGCAGCTCAGCAGCCTGACATCTGAGGACACTGCCGTCTATTACTGTTCTAACTGGGATTACTTTGACTACTGGGGCCAAGGCACCGCTCTCACAGTCTCCTCA | 151 |
| | | Light Kappa | DVVMTQTPLTLSVTIGQPASISCKSSQSLLDSDGKTYLNWLLQRPGQSPKRLIYLVSKLDSGVPDRFTGSGSGTDFTLKISRVEAEDLGVYYCSQGTHFPRTFGGGTKLEIK | 140 | GATGTTGTGATGACCCAGACTCCACTCACTTTGTCGGTTACCATTGGACAGCCAGCCTCCATCTCTTGCAAGTCAAGTCAGAGCCTCTTAGATAGTGATGGAAAGACATATTTGAATTGGTTGTTACAGAGGCCAGGCCAGTCTCCAAAGCGCCTAATCTATCTGGTGTCTAAACTGGACTCTGGAGTCCCTGACAGGTTCACTGGCAGTGGATCAGGGACAGATTTCACACTGAAAATCAGCAGAGTGGAGGCTGAGGATTTGGGAGTTTATTATTGCTCGCAAGGTACACATTTTCCTCGGACGTTCGGTGGAGGCACCAAGCTGGAAATCAAA | 152 |
| | 12B12 | Heavy IgG1 | EVQLQQSGAELVKPGASVKLSCTASGFNIKDTYIHWVKQRPEQGLEWIGRIDPANGNTNYDPKFQDKATITADTSSNTAYLQFSSLTSEDTAVYYCSNWDYFDYWGQGTTLTVSS | 141 | GAGGTTCAGCTGCAGCAGTCTGGGGCAGAACTTGTGAAGCCAGGGGCCTCAGTCAAGTTGTCCTGCACAGCTTCTGGCTTCAACATTAAAGACACCTATATACACTGGGTGAAGCAGAGGCCTGAACAGGGCCTGGAGTGGATTGGAGGGATTGATCCTGCGAATGGTAATACTAATTATGACCCGAAGTTCCAGGACAAGGCCACTATAACAGCAGACACATCCTCCAACACAGCCTACCTGCAGTTCAGCAGCCTGACATCTGAGGACACTGCCGTCTATTACTGTTCGAACTGGGATTACTTTGACTACTGGGGCCAAGGCACCACTCTCACAGTCTCCTCA | 153 |
| | | Light Kappa | DVVLTQTPLTLSVTIGQPASIPCKSSQSLLDSDGKTYLNWLLQRPGQSPKRLIYLVSKLDSGVPDRFTGSGSGTDFTLKISRVEAEDLGVYYCSQGTHFPRTFGGGTKLEIK | 142 | GATGTTGTGCTGACCCAGACTCCACTCACTTTGTCGGTTACCATTGGACAGCCAGCCTCCATCCCTTGCAAGTCAAGTCAGAGCCTCTTAGATAGTGATGGAAAGACATATTTGAATTGGTTGTTACAGAGGCCAGGCCAGTCTCCAAAGCGCCTAATCTATCTGGTGTCTAAACTGGACTCTGGAGTCCCTGACAGGTTCACTGGCAGTGGATCAGGGACAGATTTCACACTGAAAATCAGCAGAGTGGAGGCTGAGGATTTGGGAGTTTATTATTGCTCGCAAGGTACACATTTTCCTCGGACGTTCGGTGGAGGCACCAAGCTGGAAATCAAA | 154 |
| 4, 2 | 11B6 | Heavy IgG1 | QVQLQQSGAELMKPGASVKISCKATGYTFSSYWVEWVKLRPGHGLEWIGEIF | 143 | CAGGTTCAGCTGCAGCAGTCTGGAGCTGAGCTGATGAAGCCTGGGGCCTCAGTGAAGATATCCTGCAAGGCTACTGGCTACACATTCAGTAGTTACTGGGTAGAGTGGGTAAAGCTGAGGCCTGGACATGGCCTTGAGTGGATTGGAGAGAT | 155 |

TABLE 14-continued

Sequences of variable heavy and light chains

| Peptide Scaffold | Clone | Chain | Amino acid sequence | SEQ ID NO | Nucleic acid sequence | SEQ ID NO |
|---|---|---|---|---|---|---|
| | | | PGSGSANYNEKFK<br>GKATFTADTSSNT<br>AYMQLSSLTSEDS<br>AVYYCTSRWYPDY<br>FEYWGQGTTLTVS<br>S | | TTTCCCTGGAAGTGGTAGTGCTAATTACAATGAGAAGT<br>TCAAGGGCAAGGCCACATTCACTGCAGATACATCCTCC<br>AACACAGCCTACATGCAACTCAGCAGCCTGACATCTGA<br>GGATTCTGCCGTCTATTACTGTACAAGTAGATGGTATC<br>CTGACTACTTTGAATATTGGGGCCAAGGCACCACTCTC<br>ACAGTCTCCTCA | |
| | | Light Kappa | DVVMTQTPLSLPV<br>SLGDQASISCRSS<br>QSLVHSNGNTYLH<br>WYLQKPGQSPKLL<br>IYKVSNRFSGVPD<br>RFSGSGSGTDFTL<br>KISRVEAEDLGVY<br>FCSQSTHVPYTFG<br>GGTKLEIR | 144 | GATGTTGTGATGACCCAAACTCCACTCTCCCTGCCTGT<br>CAGTCTTGGAGATCAAGCCTCCATCTCTTGCAGATCTA<br>GTCAGAGCCTTGTACACAGTAATGGAAACACCTATTTA<br>CATTGGTACCTGCAGAAGCCAGGCCAGTCTCCAAAGCT<br>CCTGATCTACAAAGTTCCAACCGATTTTCTGGGGTCC<br>CAGACAGGTTCAGTGGCAGTGGATCAGGGACAGATTTC<br>ACACTCAAGATCAGCAGAGTGGAGGCTGAGGATCTGGG<br>AGTTTATTTCTGCTCTCAAAGTACACATGTTCCGTACA<br>CGTTCGGAGGGGGGACCAAGCTGGAAATAAGA | 156 |

Table 15 below shows signal sequences that may be linked to the antibody chain, optionally at the amino terminus.

TABLE 15

Signal sequences

| Amino acid | SEQ ID NO | Nucleic acid | SEQ ID NO |
|---|---|---|---|
| MDFGLIFFIVALLKGVQC | 157 | ATGGATTTTGGGCTGATTTTTTTTATTGTTGCTCTTT TAAAAGGGGTCCAGTGT | 169 |
| MDSQAQVLMLLLLWVSGTCG | 158 | ATGGATTCACAGGCCCAGGTTCTTATGTTACTGCTGC TATGGGTATCTGGTACCTGTGGG | 170 |
| MGRLTSSFLLLIVPAYVLS | 159 | ATGGGCAGGCTTACTTCTTCATTCTTGCTACTGATTG TCCCTGCATATGTCCTGTCC | 171 |
| MKLPVRLLVLMFWIPASSS | 160 | ATGAAGTTGCCTGTTAGGCTGTTGGTGCTGATGTTCT GGATTCCTGCTTCCAGCAGT | 172 |
| MEWLWNLLFLMAAAQSIQA | 161 | ATGGAATGGCTGTGGAACTTGCTATTTCTCATGGCAG CAGCTCAAAGTATCCAAGCA | 173 |
| MSPAQFLFLLVFWIRETNG | 162 | ATGAGTCCTGCCCAGTTCCTGTTTCTGTTAGTGTTCT GGATTCGGGAAACCAACGGT | 174 |
| MKCSWVIFFLMAWTGVN | 163 | ATGAAATGCAGCTGGGTTATCTTCTTCCTGATGGCAG TGGTTACAGGGGTCAATTCA | 175 |
| MSPAQFLFLLVLWIRETNG | 164 | ATGAGTCCTGCCCAGTTCCTGTTTCTGTTAGTGCTCT GGATTCGGGAAACCAACGGT | 176 |
| MKCSWVIFFLMAWTGVNS | 165 | ATGAAATGCAGCTGGGTTATCTTCTTCCTGATGGCAG TGGTTACAGGGGTCAATTCG | 177 |
| MSPAQFLFLLVLWIRETNG | 164 | ATGAGTCCTGCCCAGTTCCTGTTTCTGTTAGTGCTCT GGATTCGGGAAACCAACGGT | 176 |
| MEWTWVFLFLLSVTAGGHS | 157 | ATGGAATGGACCTGGGTCTTTCTCTTCCTCCTGTCAG TAACTGCAGGTGGCCACTCC | 179 |
| MKLPVRLLVLMFWIPASSS | 160 | ATGAAGTTGCCTGTTAGGCTGTTGGTGCTGATGTTCT GGATTCCTGCTTCCAGCAGT | 172 |

Assessment of CDR and Antibody Sequencing Consensus

VH and VL sequences were confirmed through sequencing of 5 cloning vectors containing amplified antibody fragments for the variable IgG1 heavy chain and variable kappa light chain. For antibodies 2E9, 9D8, 12G1, 3C11, 12B12, 10D5 and 11B6, 100% alignment was obtained across the 5 sequencing traces, providing confident assurance of the reported framework and CDR1, CDR2 and CDR3 regions of both heavy and light chains. No alternate nucleotides and/or amino acids were identified for the reported heavy and light chain sequences.

Example 16

Relative Binding of alpha-Syn Species

Purified antibodies 2E9, 12B12 and 12G1 and 3 alpha-syn comparator antibodies purchased from Creative Biolabs) were immobilized onto a sensorchip surface for SPR analysis. Appoximately 5000 RUs of each antibody was immobilized. Serial dilutions of alpha-syn monomers, tetramers or sonicated preformed fibrils (soluble fibrils) were injected over the antibodies. Binding interactions were measured and relative binding of soluble fibrils :monomers and tetramer forms computed.

The ratio of antibody binding to soluble fibril versus native monomer and tetramer of the test antibodies are presented below.

TABLE 16

Test antibody binding affinity to monomer versus tetramer

| Antibody | Soluble fibril:monomer | Soluble fibril:tetramer |
| --- | --- | --- |
| 2E9 | More than 10 fold greater binding affinity for soluble fibril relative to monomer | No binding to tetramer under study conditions, ratio could not be calculated |
| 12B12 | More than 10 fold greater binding affinity for soluble fibril relative to monomer | More than 20 fold greater binding affinity for soluble fibril relative to tetramer |
| 12G1 | More than 50 fold greater binding affinity for soluble fibril relative to monomer | No binding to tetramer under study conditions, ratio could not be calculated |

The test antibodies unlike the three comparator antibodies, exhibited more than 10 fold greater binding for the soluble fibril alpha-syn relative to either the monomer or tetramer species.

Example 17

In Vitro Propagation of Alpha-Synuclein Aggregation

Alpha-synuclein monomers (100 uM) were incubated with 10 nM soluble human pre-formed fibrils (huPFF) that act as a seed to trigger aggregation.

As shown in FIG. 15A, monomers incubated alone did not aggregate under the conditions tested. Aggregation gives rise to the formation of beta-sheets which are bound by Thioflavin-T (25 uM), giving rise to a fluorescence signal proportional to the amount of aggregation. The 2E9 antibody added at 0.1 nM (1:100 molar ratio of 2E9:huPFF) inhibited the propagation of aggregation.

Seeding by Cyclic Peptide and Inhibition by 2E9

Sonicated, pre-formed fibrils of α-Syn (PFFs) are known to act as a seed to trigger aggregation. The ability of cyclic peptide (CGTKEQGGGG) (SEQ ID NO: 7) alone to replicate the seeding activity of PFFs was tested using the Thioflavin-T assay described in this Example. Aggregation gives rise to the formation of beta-sheets which are bound by Thioflavin-T (25 uM), producing a fluorescence signal proportional to the amount of aggregation.

α-Syn monomers (100 uM) were incubated with 100 nM of the BSA-conjugated cyclic peptide (SEQ ID NO: 7; the cyclic peptide used to raise antibody 2E9) as a seed, or BSA-conjugated corresponding linear peptide as a control.

As shown in FIG. 15B, monomers incubated alone or in the presence of linear peptide did not aggregate. In contrast, the cyclic peptide possessed a conformation capable of acting as a seed and inducing progressive aggregation of α-Syn over time. The 2E9 antibody added at 0.1 nM inhibited the propagation of aggregation (FIG. 15B).

Example 18

Binding of Antibodies to Brain Extract from Multiple System Atrophy (MSA) Patient Antibodies were immobilized directly onto sensor chips via amine coupling. A pan alpha-synuclein antibody (4D6) was used as a positive control and murine IgG1 (m IgG1) was used as a negative isotype control. Soluble brain extract from the cerebellum of a 50 year old female MSA patient (200 ug/ml) was injected over the immobilized antibodies for 8 min, followed by a 5 min dissociation. Binding responses (in terms of response units, RU) at 30s into the dissociation phase are shown in FIG. 16A. As can be seen, the test antibodies 2E9, 12G1, 11B6, 12B12, 3C11, 9D8 and 10D5 showed binding response above the background binding response obtained with m IgG1, and the binding response was greater than that seen with the control pan alpha-syn (4D6) antibody.

SPR Analysis of Binding to Unfractionated Human Soluble MSA Brain Extract

SPR analysis of unfractionated human soluble MSA brain extract from the cerebellum of a 50-year-old female with multiple system atrophy (MSA) was conducted as described in this Example. Test antibodies, positive control antibody (pan α-Syn 4D6), comparator anti-α-Syn antibodies from Creative Biolabs (mAb49/G, NI-202.12F4, PRX002) and murine IgG isotype control (mIgG1) were immobilized at high densities (approximately 12,000 to 20,000 RUs) on flow cells of a sensor chip. Brain soluble extract diluted to 200 ug/ml was injected over the surfaces for approximately 8 minutes at 10 ul/min, followed by a 5-minute dissociation (quadruplicate measurements). As shown in FIG. 16B, all test antibodies and the comparators showed a binding response above the background binding response obtained with m IgG1. The binding responses of the test antibodies were also greater than that seen with the control pan alpha-syn (4D6) antibody. The NI-202.12F4 antibody binds N-terminal residues 1-10, the PRX002 antibody binds residues 118-126.

SPR Analysis of Binding to a "Prion-Enriched" Fraction from Human MSA Brain Extract A brain sample from the cerebellum of a 50-year-old female with MSA was homogenized as described above (Example 7). The homogenate was then processed as described by Aoyagi et al (Science Translational Medicine, eaat8462, 2019) to isolate a "prion-enriched fraction" containing self-propagating species of α-Syn. Briefly, 2% sarkosyl and 0.5% benzonase were added to the homogenate and incubated at 37° C. for 2 hrs with shaking. Phosphotungstic acid (PTA) was then added at a final concentration of 2% and the mixture was incubated at 37° C. overnight with shaking. The material was then centrifuged for 30 min at 16,100×g and the resulting pellet was resuspended in 2% sarkosyl and 2% PTA and incubated at 37° C. for 1 hour with shaking (to wash off residual sarkosyl-soluble proteins). The mixture was then centrifuged for 30 min at 16,100×g and the final pellet was resuspended in PBS for SPR analysis.

Test antibodies, positive control antibody (pan α-Syn 4D6) and murine IgG isotype control (mIgG1) were immobilized at high densities (approximately 18,000 to 24,000 RUs) on flow cells of a sensor chip. The re-suspended pellet material (estimated protein concentration of 250-375 ug/ml) was injected over the surfaces for approximately 8 minutes at 10 ul/min, followed by a dissociation period of approximately 200s (duplicate measurements). Binding responses were double-referenced by subtraction of IgG reference surface binding and normalized with assay buffer. Results are shown in FIG. 16C. All test antibodies showed a binding response above the background binding response obtained with mIgG1. The binding responses of the test antibodies were comparable or greater than that seen with the control pan alpha-syn (4D6) antibody which is expected to bind both the prions and any remaining contaminating α-Syn species remaining in the prion-enriched prep.

Example 19

Measurement of Misfolded α-SynOligomers in Biosamples

Figure 20:
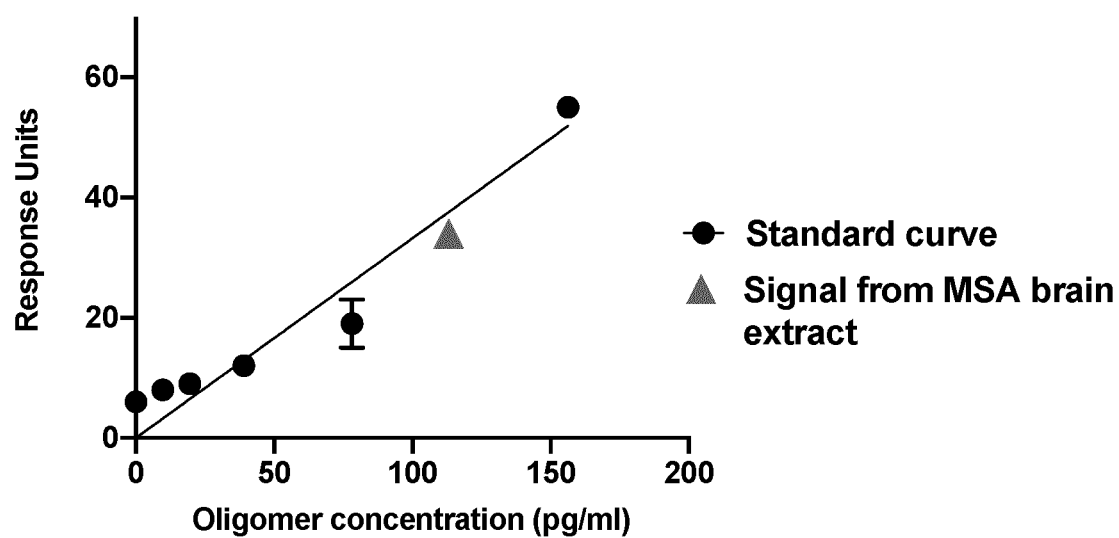
FIG. 20 is graph showing the quantitation of misfolded oligomeric α-syn in a biosample.

The 12G1 antibody was used in the EMD Millipore SMC™ platform. To generate a standard curve, magnetic particles were coated with 12.5 ug/ml of 12G1 antibody and exposed to various concentrations of α-syn oligomers ranging from 0-156 pg/ml. Captured α-Syn was then detected using a labeled pan α-Syn antibody (4D6) at a concentration of 1,500 ng/ml. The standard curve shows the signal (Response Units) from the eluted detector antibody at the different α-Syn concentrations. 12G1-coated magnetic particles were then exposed to MSA brain extract (1,277 ug/ml total protein) following the same protocol. The signal obtained was used to derive the amount of α-Syn oligomers present in the sample using the standard curve. The amount was estimated to be approximately 113 pg/ml (FIG. 20).

Example 20

Analysis of Selectivity Using the Millipore "Single Molecule Counting" (SMC™) Platform The binding of test antibodies 12G1 (FIG. 17A-C), 9D8 (FIG. 18A-C), and 10D5 (FIG. 19A-C) to α-Syn monomers vs oligomers vs sonicated fibrils was evaluated on the Millipore SMC™ platform to determine the lower limit of quantitation (LLoQ) and relative selectivity of the antibodies for these species. Briefly, magnetic particles were coated with the test antibody at 12.5 ug/ml (12G1, 10D5) or 25 ug/ml (9D8). The coated particles were exposed to a wide range of α-Syn concentrations going up to 1400 ng/ml for monomers, 10,000 pg/ml for oligomers and up to 1,000 pg/ml for soluble, sonicated fibrils. Captured α-Syn was then detected using a labeled pan α-Syn antibody (4D6) at a concentration of 1,500 ng/ml. The binding curves show the signal (Response Units) from the eluted detector antibody for the different α-Syn concentrations. The LLoQ is defined as the interpolated value at which the signal is 2.5× background.

All 3 antibodies tested showed much greater reactivity with α-Syn oligomers and fibrils (the pathogenic species of α-Syn) compared to monomers. Based on the LLoQ values, the fold selectivity for oligomers vs monomers ranged from 9,300-35,000×, and the fold selectivity for soluble fibrils vs monomers ranged from 11,200-175,000×. Specifically, 12G1 fold selectivity for oligomers versus monomers was 35,000×, and for fibrils versus monomers was 175,0000× (FIGS. 17A-C). 9D8 fold selectivity for oligomers versus monomers was 9,300×, and for fibrils versus monomers was 93,300× (FIGS. 18A-C). 10D5 fold selectivity for oligomers versus monomers was 9,300×, and for fibrils was 11,200× FIGS. 19A-C).

Example 21

SPR Affinity Measurements

For SPR analysis of the binding parameters of antibodies to various α-Syn species (monomers, physiologic tetramers, oligomers and soluble fibrils), the antibodies were immobilized at approximately 2,000-4,500 RUs on flow cells of a sensor chip. The α-Syn analytes diluted 2-fold from 1,000-0.5 nM (12-point dilution series) were injected sequentially over the surfaces for approximately 4 minutes followed by approximately 5 min of dissociation in buffer and surface regeneration. Binding parameters were calculated using steady state (monomers, physiologic tetramers) or kinetic (oligomers, sonicated fibrils) curve fitting and a Langmuir 1:1 binding model. Results are summarized in Table 17.

Compared to other α-Syn antibodies obtained commercially (Creative Biolabs, clones PRX002 and NI-202.12F4), the antibodies tested (2E9, 12G1, 12B12) showed greater selectivity for pathogenic α-Syn species, with negligible binding to monomers and physiologic tetramers, but strong affinity for oligomers and sonicated fibrils.

TABLE 17

SPR affinity measurements - Quantitative values supporting the selectivity for oligomers and soluble fibrils

| Antibody | Monomers* KD (uM) | Physiologic Tetramers* KD (uM) | Oligomers[#] $k_A$ [1/(M·s)] | $k_D$ [1/s] | KD (uM) | Sonicated Fibrils[#] $k_A$ [1/(M·s)] | $k_D$ [1/s] | KD (uM) |
|---|---|---|---|---|---|---|---|---|
| 2E9 | — | — | 2.01E+03 | 8.65E−04 | 0.431 | 6.67E+03 | 6.29E−05 | 0.009 |
| 12G1 | — | — | 9.66E+02 | 1.55E−03 | 1.608 | 2.82E+03 | 5.62E−05 | 0.020 |
| 12B12 | — | — | 1.32E+03 | 1.30E−03 | 0.985 | 2.53E+03 | 2.09E−05 | 0.008 |
| PRX002 | 0.10 | 0.05 | 2.51E+04 | 1.81E−03 | 0.072 | 1.95E+04 | 2.09E−04 | 0.011 |
| NI-202.12F4 | 8.6 | 14.00 | 7.64E+03 | 1.00E−03 | 0.131 | 3.10E+03 | 3.75E−05 | 0.012 |

TABLE 17-continued

SPR affinity measurements - Quantitative values supporting the selectivity for oligomers and soluble fibrils

| Antibody | Monomers* KD (uM) | Physiologic Tetramers* KD (uM) | Oligomers# | | | Sonicated Fibrils# | | |
|---|---|---|---|---|---|---|---|---|
| | | | $k_A$ [1/(M·s)] | $k_D$ [1/s] | KD (uM) | $k_A$ [1/(M·s)] | $k_D$ [1/s] | KD (uM) |
| 2E9 | — | — | 2.01E+03 | 8.65E−04 | 0.431 | 6.67E+03 | 6.29E−05 | 0.009 |
| 12G1 | — | — | 9.66E+02 | 1.55E−03 | 1.608 | 2.82E+03 | 5.62E−05 | 0.020 |
| 12B12 | — | — | 1.32E+03 | 1.30E−03 | 0.985 | 2.53E+03 | 2.09E−05 | 0.008 |
| PRX002 | 0.10 | 0.05 | 2.51E+04 | 1.81E−03 | 0.072 | 1.95E+04 | 2.09E−04 | 0.011 |
| NI-202.12F4 | 8.6 | 14.00 | 7.64E+03 | 1.00E−03 | 0.131 | 3.10E+03 | 3.75E−05 | 0.012 |

*Steady state fitting,
Kinetic fitting
—: Binding too weak to measure KD

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

The scope of the claims should not be limited by the preferred embodiments and examples, but should be given the broadest interpretation consistent with the description as a whole.

REFERENCES

Aoyagi et al. (2019). Aβ and tau prion-like activities decline with longevity in the Alzheimer's disease human brain. Sci. Transl. Med., eaat8462.

Schinelli, S., Zuddas, A., Kopin, I. J., Barker, J. L., & D I Porzio, U. (1988). 1-Methyl-4-phenyl-1,2,3,6-tetrahydropyridine metabolism and 1-methyl-4-phenylpyridinium uptake in dissociated cell cultures from the embryonic mesencephalon. J Neurochem., 50, 1900-1907.

Costanzo, M., and Zurzolo, C. (2013). The cell biology of prion-like spread of protein aggregates: mechanisms and implication in neurodegeneration. Biochem. J. 452, 1-17.

Guo, J. L., and Lee, V. M. (2014). Cell-to-cell transmission of pathogenic proteins in neurodegenerative diseases. Nat. Med. 20, 130-138.

Harrison N L. (1990) On the presynaptic action of baclofen at inhibitory synapses between cultured rat hippocampalneurones. J Physiol. 1990 March; 422:433-46.

Jucker M and Walker L C. (2013) Self-propagation of pathogenic protein aggregates in neurodegenerative diseases. Nature. September 5; 501(7465):45-51.

Prusiner, S. B. (2012). Cell biology. A unifying role for prions in neurodegenerative diseases. Science 336, 1511-1513.

Volpicelli-Daley L., Luk K., Lee V. (2014) Addition of exogenous α-Synuclein Pre-formed fibrils to Primary Neuronal Cultures to seed recruitment of endogenous α-Synuclein to Lewy body and Lewy Neurite-like aggregates. Nat Protoc. 9(9): 2135-2146.

Nuber, Silke, Molly Rajsombath, Georgia Minakaki . . . Barbara Caldarone, Ulf Dettmer, and Dennis J. Selkoe. Abrogating Native α-Synuclein Tetramers in Mice Causes a LDOPA-Responsive Motor Syndrome Closely Resembling Parkinson's Disease. NEURON Oct. 10, 2018.

Peng 2018 Journal Physical Chemistry B. Prediction of Misfolding-Specific Epitopes in SOD1 Using Collective Coordinates Xubiao Peng, Neil R. Cashman, and Steven S. Plotkin, *The Journal of Physical Chemistry B* 2018 122 (49), 11662-11676.

The invention claimed is:

1. An antibody that binds an epitope in EKTKEQ (SEQ ID NO: 1), in misfolded oligomeric alpha-Syn polypeptide, wherein the antibody comprises a heavy chain variable region and a light chain variable region, the heavy chain variable region comprising complementarity determining regions CDR-H1, CDR-H2 and CDR-H3, and the light chain variable region comprising complementarity determining regions CDR-L1, CDR-L2 and CDR-L3, wherein the complementarity determining regions CDR-H1, CDR-H2, CDR-H3, CDR-L1, CDR-L2 and CDR-L3 have amino acid sequences of SEQ ID NOs: 61-66, respectively, SEQ ID NOs: 67-72, respectively, SEQ ID NOs: 73-78, respectively, SEQ ID NOs: 79-81, 76, 77, and 84, respectively, SEQ ID NOs: 91-94, 71, and 96, respectively, or amino acid sequences of SEQ ID NOs: 180, 181, 182, 183, 77, and 184 respectively.

2. The antibody of claim 1, wherein the antibody is raised using an immunogen comprising a cyclic compound comprising an α-Syn peptide comprising at least 3 residues of EKTKEQ (SEQ ID NO: 1), optionally EKT, KTK, KEQ, EKTK (SEQ ID NO: 2), KTKE (SEQ ID NO: 3), TKEQ (SEQ ID NO: 4), or TEQ, and a linker, wherein the linker is covalently coupled to the peptide N-terminus residue and the C-terminus residue, or a composition comprising said immunogen, optionally wherein the composition used to raise the antibody comprises an adjuvant, optionally aluminum phosphate or aluminum hydroxide.

3. The antibody of claim 1, wherein the antibody selectively binds the α-Syn peptide in misfolded oligomeric α-Syn compared to native α-Syn polypeptide; and/or selectively binds misfolded oligomeric α-Syn polypeptide compared to native α-Syn polypeptide, wherein the antibody is at least 2 fold, 3 fold, at least 5 fold, at least 10 fold, at least 20 fold, at least 30 fold, at least 40 fold, at least 50 fold, at least 100 fold, at least 500 fold, or at least 1000 fold more selective for a cyclic compound compared to a corresponding linear compound and/or to native α-Syn polypeptide, or for misfolded oligomeric α-Syn polypeptide compared to native α-Syn polypeptide.

4. The antibody of claim 1, wherein the heavy chain variable region and light chain variable region comprises an amino acid sequence of any one of the following:
- SEQ ID NOs: 133 and 134 or an amino acid sequence having at least 80%, 90%, 95% or 98% sequence identity SEQ ID NOs: 133 and 134, respectively;
- SEQ ID NOs: 135 and 136 or an amino acid sequence having at least 80%, 90%, 95% or 98% sequence identity SEQ ID NOs: 135 and 136, respectively;
- SEQ ID NOs: 137 and 138 or an amino acid sequence having at least 80%, 90%, 95% or 98% sequence identity SEQ ID NOs: 137 and 138, respectively;
- SEQ ID NOs: 139 and 140 or an amino acid sequence having at least 80%, 90%, 95% or 98% sequence identity SEQ ID NOs: 139 and 140, respectively;
- SEQ ID NOs: 141 and 142 or an amino acid sequence having at least 80%, 90%, 95% or 98% sequence identity SEQ ID NOs: 141 and 142, respectively;
- SEQ ID NOs: 143 and 144 or an amino acid sequence having at least 80%, 90%, 95% or 98% sequence identity SEQ ID NOs: 143 and 144, respectively; or
- SEQ ID NOs: 190 and 191 or an amino acid sequence having at least 80%, 90%, 95% or 98% sequence identity SEQ ID NOs: 190 and 191, respectively;
wherein the CDR sequences are maintained.

5. The antibody of claim 1, wherein the antibody is selected from the group consisting of a monoclonal antibody, an immunoglobulin molecule, a Fab, a Fab', a F(ab)2, a F(ab')2, a Fv, a disulfide linked Fv, a scFv, a disulfide linked scFv, a single chain antibody, a diabody, a dimer, a minibody, a bispecific antibody fragment, a chimeric antibody, and a humanized antibody.

6. An immunoconjugate comprising the antibody of claim 1 and a moiety, wherein the moiety is a detectable label or a particle, optionally a magnetic particle.

7. A nucleic acid molecule comprising a nucleic acid sequence encoding the antibody of claim 1 or an immunoconjugate comprising said antibody.

8. The nucleic acid of claim 7, wherein the nucleic acid comprises a nucleic acid encoding a heavy chain variable region, the heavy chain variable region comprising complementarity determining regions CDR-H1, CDR-H2 and CDR-H3
wherein the complementarity determining regions CDR-H1, CDR-H2 and CDR-H3 are encoded by nucleic acid sequences having SEQ ID Nos: 97-99, respectively, SEQ ID Nos: 103-105, respectively, SEQ ID Nos: 109-111, respectively, SEQ ID Nos: 115-117, respectively, SEQ ID Nos: 115, 116, and 123, respectively, SEQ ID Nos: 127-129, respectively, or SEQ ID Nos: 185, 186 and 187 respectively;
optionally wherein the heavy chain variable region is encoded by a nucleic acid sequence comprising any one of SEQ ID Nos: 145, 147, 149, 151, 153, 155 and 192; a sequence with at least 80%, 90%, 95%, 98% or 99% sequence identity to any of the foregoing wherein the amino acid sequence of the CDR regions are maintained; a sequence encoding any one of SEQ ID Nos: 133, 135, 137, 139, 141, 143 and 190; or encoding an amino acid sequence having at least 80%, 90%, 95% 98% or 99% sequence identity to any one of SEQ ID Nos: 133, 135, 137, 139, 141, 143 and 190, wherein the CDR amino acid sequences are maintained.

9. The nucleic acid of claim 7, wherein the nucleic acid sequence encodes a light chain variable region, the light chain variable region comprising complementarity determining regions CDR-L1, CDR-L2 and CDR-L3
wherein the complementarity determining regions CDR-L1, CDR-L2 and CDR-L3 are encoded by nucleic acid sequences of having SEQ ID Nos: 100-102, respectively, SEQ ID Nos: 106-108, respectively, SEQ ID Nos: 112-114, respectively, SEQ ID Nos: 112, 113, and 120, respectively, SEQ ID Nos: 130, 107, and 132, respectively, or SEQ ID Nos: 188,113, and 189 respectively;
optionally wherein the light chain variable region is encoded by a nucleic acid sequence comprising any one of SEQ ID Nos: 146, 148, 150, 152, 154 156 and 193; a sequence with at least 80%, 90%, 95%, 98% or 99% sequence identity to any of the foregoing wherein the amino acid sequence of the CDR regions are maintained; a sequence encoding any one of SEQ ID Nos: 134, 136, 138, 140, 142, 144 and 191; or encoding an amino acid sequence having at least 80%, 90%, 95% or 98% sequence identity to any one of SEQ ID Nos: 134, 136, 138, 140, 142, 144 and 191, wherein the CDR sequences are maintained.

10. The nucleic acid of claim 7, wherein the nucleic acid sequence encodes i) a heavy chain variable region, the heavy chain variable region comprising complementarity determining regions CDR-H1, CDR-H2 and CDR-H3 and ii) a light chain variable region comprising complementarity determining regions CDR-L1, CDR-L2 and CDR-L3,
wherein the complementarity determining regions CDR-H1, CDR-H2, CDR-H3, CDR-L1, CDR-L2 and CDR-L3 are encoded by nucleic acid sequences having SEQ ID Nos: 97-102, respectively, SEQ ID Nos: 103-108, respectively, SEQ ID Nos: 109-114, respectively, SEQ ID Nos: 115-117, 112, 113, and 120, respectively, SEQ ID Nos: 115, 116, 123, 112, 113, and 120, respectively, SEQ ID Nos: 127-130, 107, and 132, respectively, or SEQ ID Nos 185-188, 113, and 189 respectively;
optionally wherein the heavy chain variable region is encoded by a nucleic acid sequence comprising any one of SEQ ID Nos: 145, 147, 149, 151, 153, 155 and 192: a sequence with at least 80%, 90%, 95%, 98% or 99% sequence identity to any of the foregoing wherein the amino acid sequence of the CDR regions are maintained; a sequence encoding any one of SEQ ID Nos: 133, 135, 137, 139, 141, 143 and 190; or encoding an amino acid sequence having at least 80%, 90%, 95% 98% or 99% sequence identity to any one of SEQ ID Nos: 133, 135, 137, 139, 141, 143 and 190, wherein the CDR amino acid sequences are maintained, and/or
wherein the light chain variable region is encoded by a nucleic acid sequence comprising any one of SEQ ID Nos: 146, 148, 150, 152, 154 156 and 193; a sequence with at least 80%, 90%, 95%, 98% or 99% sequence identity to any of the foregoing wherein the amino acid sequence of the CDR regions are maintained; a sequence encoding any one of SEQ ID Nos: 134, 136, 138, 140, 142, 144 and 191; or encoding an amino acid sequence having at least 80%, 90%, 95% or 98% sequence identity to any one of SEQ ID Nos: 134, 136, 138, 140, 142, 144 and 191, wherein the CDR sequences are maintained.

11. A vector comprising the nucleic acid of claim 7, optionally further comprising a signal sequence, optionally selected from SEQ ID Nos: 157 to 164, 169-177, and 179.

12. A recombinant cell expressing the antibody of claim 1, optionally wherein the recombinant cell is a mammalian cell, optionally a hybridoma cell or a CHO cell.

13. A composition comprising the antibody of claim 1 or an immunoconjugate comprising said antibody, a nucleic acid encoding said antibody or immunoconjugate, a vector or recombinant cell expressing said antibody, optionally comprising one or more of the antibody, immunoconjugate, nucleic acid, vector or recombinant cell, optionally, 2 or more, or 3 or more.

14. A kit comprising the antibody of claim 1 or an immunoconjugate comprising said antibody, a nucleic acid comprising a nucleic acid sequence encoding said antibody or immunoconjugate, a vector or recombinant cell expressing said antibody, a composition comprising said antibody, immunoconjugate, nucleic acid, vector, or recombinant cell, optionally with one or more reagents, particles, or plates.

15. An assay for determining if a test sample contains misfolded α-Syn polypeptide the method comprising:
  a. contacting the test sample, optionally comprising blood, serum, plasma, brain tissue extract and/or CSF, with the antibody of claim 1 or an immunoconjugate comprising the antibody, under conditions permissive for forming an antibody: misfolded α-Syn polypeptide complex, optionally wherein the antibody is conjugated to a particle, optionally a magnetic bead; and
  b. detecting and/or quantitating the presence of any antibody: misfolded α-Syn polypeptide complex, optionally wherein the quantity of antibody: misfolded α-Syn polypeptide complex is quantitated and/or compared to a control and/or wherein detecting the complex comprises contacting the complex with a pan alpha-Syn antibody;
  wherein the presence of detectable complex is indicative that the test sample may contain misfolded α-Syn polypeptide,
  optionally, wherein the test sample is a human sample,
  optionally wherein the assay further comprises detecting and/or quantitating the presence of antibody: misfolded α-Syn polypeptide complex in a subsequent test sample and optionally comparing to the test sample, and/or detecting and/or quantitating the presence of antibody: misfolded α-Syn polypeptide complex in a subsequent test sample and optionally comparing to the test sample,
  optionally wherein detecting the complex or quantitating the complex comprises contacting the complex with a labelled pan alpha-syn antibody.

16. The assay of claim 15 for use in a method of diagnosing whether a subject has an α-synucleinopathy, optionally selected from Parkinson's disease (PD), Lewy body disease (LBD) or multiple system atrophy, comprising:
  C. detecting an amount of misfolded α-synuclein in the subject's test sample;
  d. comparing the amount of misfolded α-synuclein with a control, wherein the control is a cut-off or range found in a population of control samples;
  wherein the subject may have an α-synucleinopathy if the amount of misfolded α-synuclein is higher than a level or range found in normal control samples or within a range found in control samples from subjects with the synucleinopathy.

17. A method of inhibiting misfolded alpha-syn toxicity comprising administering to a cell population or a subject in need thereof an effective amount of the antibody of claim 1 or an immunoconjugate comprising said antibody or a composition comprising said antibody or immunoconjugate, wherein the antibody selectively binds misfolded oligomeric alpha-Syn compared to monomeric, native tetrameric and/or insoluble fibril α-synuclein species, optionally wherein the method is for treating a subject with an α-synucleinopathy, optionally Parkinson's disease (PD), Lewy body disease (LBD) or multiple system atrophy.

18. A composition comprising i) a first nucleic acid molecule encoding a heavy chain variable region, the heavy chain variable region comprising complementarity determining regions CDR-H1, CDR-H2 and CDR-H3 and ii) a second nucleic acid molecule encoding a light chain variable region comprising complementarity determining regions CDR-L1, CDR-L2 and CDR-L3,
  wherein the complementarity determining regions CDR-H1, CDR-H2, CDR-H3, CDR-L1, CDR-L2 and CDR-L3 are encoded by nucleic acid sequences having SEQ ID Nos: 97-102, respectively, SEQ ID Nos: 103-108, respectively, SEQ ID Nos: 109-114, respectively, SEQ ID Nos: 115-117, 112, 113, and 120, respectively, SEQ ID Nos: 115, 116, 123, 112, 113, and 120, respectively, SEQ ID Nos: 127-130, 107, and 132, respectively, or SEQ ID Nos 185-188, 113, and 189 respectively;
  optionally wherein the heavy chain variable region is encoded by a nucleic acid sequence comprising any one of SEQ ID Nos: 145, 147, 149, 151, 153, 155 and 192: a sequence with at least 80%, 90%, 95%, 98% or 99% sequence identity to any of the foregoing wherein the amino acid sequence of the CDR regions are maintained; a sequence encoding any one of SEQ ID Nos: 133, 135, 137, 139, 141, 143 and 190; or encoding an amino acid sequence having at least 80%, 90%, 95% 98% or 99% sequence identity to any one of SEQ ID Nos: 133, 135, 137, 139, 141, 143 and 190, wherein the CDR amino acid sequences are maintained, and/or
  wherein the light chain variable region is encoded by a nucleic acid sequence comprising any one of SEQ ID Nos: 146, 148, 150, 152, 154 156 and 193; a sequence with at least 80%, 90%, 95%, 98% or 99% sequence identity to any of the foregoing wherein the amino acid sequence of the CDR regions are maintained; a sequence encoding any one of SEQ ID Nos: 134, 136, 138, 140, 142, 144 and 191; or encoding an amino acid sequence having at least 80%, 90%, 95% or 98% sequence identity to any one of SEQ ID Nos: 134, 136, 138, 140, 142, 144 and 191, wherein the CDR sequences are maintained;
  wherein the first nucleic acid molecule and the second nucleic acid molecule encode the antibody of claim 1.

* * * * *